US008993577B2

(12) United States Patent
Griffin

(10) Patent No.: US 8,993,577 B2
(45) Date of Patent: *Mar. 31, 2015

(54) CYCLOPROPYL AMIDE DERIVATIVES

(75) Inventor: Andrew Griffin, Montreal (CA)

(73) Assignee: Astrazeneca AB, Sodertalje (SE)

(*) Notice: Subject to any disclaimer, the term of this patent is extended or adjusted under 35 U.S.C. 154(b) by 0 days.

This patent is subject to a terminal disclaimer.

(21) Appl. No.: 12/708,550

(22) Filed: Feb. 19, 2010

(65) Prior Publication Data

US 2010/0216812 A1 Aug. 26, 2010

Related U.S. Application Data

(60) Provisional application No. 61/154,067, filed on Feb. 20, 2009.

(51) Int. Cl.
A61K 31/495 (2006.01)
C07D 241/04 (2006.01)
C07D 295/00 (2006.01)

(52) U.S. Cl.
CPC ............ C07D 241/04 (2013.01); A61K 31/495 (2013.01)
USPC ...................... 514/255.01; 544/391

(58) Field of Classification Search
CPC ........................... C07D 241/04; A61K 31/495
USPC ...................... 514/255.01; 544/391
See application file for complete search history.

(56) References Cited

U.S. PATENT DOCUMENTS

| 3,331,830 | A | 7/1967 | Tomcufcik et al. |
| 3,449,427 | A | 6/1969 | Kaiser et al. |
| 3,686,335 | A | 8/1972 | Kaiser et al. |
| 3,697,506 | A | 10/1972 | Butler |
| 4,432,987 | A | 2/1984 | Barth et al. |
| 4,547,505 | A | 10/1985 | Oepen et al. |
| 5,112,818 | A | 5/1992 | Nakagawa et al. |
| 5,434,303 | A | 7/1995 | Boehm et al. |
| 5,721,359 | A | 2/1998 | Dunn et al. |
| 6,284,761 | B1 | 9/2001 | Zhang et al. |
| 6,383,520 | B1 | 5/2002 | Hirayama et al. |
| 6,521,619 | B2 | 2/2003 | Link et al. |
| 6,544,996 | B2 | 4/2003 | Zhang et al. |
| 6,861,432 | B2 | 3/2005 | Cleve et al. |
| 7,053,089 | B2 | 5/2006 | Claiborne et al. |
| 7,145,002 | B2 | 12/2006 | Brands et al. |
| 7,217,716 | B2 | 5/2007 | Claiborne et al. |
| 7,446,199 | B2 | 11/2008 | Aronov et al. |
| 7,612,987 | B2 | 11/2009 | Kurita et al. |
| 8,063,215 | B2 | 11/2011 | Arnold et al. |
| 2004/0077618 | A1 | 4/2004 | Bennani et al. |
| 2004/0209858 | A1 | 10/2004 | Bennani et al. |
| 2005/0113309 | A1 | 5/2005 | Kim et al. |
| 2005/0143372 | A1 | 6/2005 | Ghosh et al. |
| 2007/0054917 | A1 | 3/2007 | Bruton et al. |
| 2007/0066821 | A1 | 3/2007 | Allison et al. |
| 2007/0167436 | A1 | 7/2007 | Nettekoven et al. |
| 2008/0021081 | A1 | 1/2008 | Liu et al. |
| 2008/0242653 | A1 | 10/2008 | Liu et al. |
| 2009/0076020 | A1* | 3/2009 | Arnold et al. ............ 514/252.14 |
| 2009/0093525 | A1 | 4/2009 | Du Bois et al. |
| 2009/0181981 | A1 | 7/2009 | Dunlap et al. |
| 2011/0201622 | A1* | 8/2011 | Collins ..................... 514/255.01 |
| 2011/0201623 | A1 | 8/2011 | Uczynski |
| 2012/0065193 | A1* | 3/2012 | Arnold et al. ................ 514/218 |
| 2013/0172560 | A1 | 7/2013 | Stranne |

FOREIGN PATENT DOCUMENTS

| CA | 2374627 | 12/2000 |
| CN | 1341111 | 3/2002 |
| CN | 101384581 | 3/2009 |
| CN | 101462980 | 6/2009 |
| DE | 3418167 | 11/1985 |
| DE | 3600288 | 7/1987 |
| DE | 3618004 | 12/1987 |
| EP | 0120465 | 3/1984 |
| EP | 0234036 | 9/1987 |
| EP | 0129207 B1 | 3/1988 |
| EP | 1849773 A1 | 10/2007 |
| EP | 2039689 | 3/2009 |
| GB | 1086192 | 10/1967 |
| JP | 2002534421 | 10/2002 |
| RU | 2006125441 | 1/2008 |
| SU | 1297727 | 3/1987 |
| SU | 1542415 A3 | 2/1990 |
| UZ | 3306 | 3/2007 |
| WO | 9109594 | 7/1991 |
| WO | 9303615 | 3/1993 |
| WO | 9616040 | 5/1996 |
| WO | 9637469 | 11/1996 |

(Continued)

OTHER PUBLICATIONS

Berlin et al., "Recent advances in the development of histamine H3 antagonists," Expert Opin. Ther. Patents, 2007, vol. 17(6), pp. 675-687.

De Esch et al., "Development of a pharmacophore model for histamine H3 receptor antagonists, using the newly developed molecular modeling program SLATE," J. Med. Chem., 2001, vol. 44, pp. 1666-1674.

Letavic et al., "Recent medicinal chemistry of the histamine H3 receptor," Progress in Medicinal Chemistry, 2006, vol. 44, pp. 181-206.

Mills et al., "SLATE: A method for the superposition of flexible ligands," Journal of Computer-Aided Molecular Design, 2001, vol. 15, pp. 81-96.

Sander et al., "Histamine H3 Receptor Antagonists to Clinics," Biol. Pharm. Bull., 2008, vol. 31(12), pp. 2163-2181.

(Continued)

Primary Examiner — Erich A Leeser
(74) Attorney, Agent, or Firm — Ropes & Gray LLP

(57) ABSTRACT

Disclosed herein is at least one cyclopropyl amide derivative, at least one pharmaceutical composition comprising at least one cyclopropyl amide derivative disclosed herein, and at least one method of using at least one cyclopropyl amide derivative disclosed herein for treating at least one histamine H3 receptor associated condition therewith.

4 Claims, 1 Drawing Sheet

(56) References Cited

FOREIGN PATENT DOCUMENTS

| WO | 9833784 | 8/1998 |
|---|---|---|
| WO | 9837077 | 8/1998 |
| WO | 9937304 | 7/1999 |
| WO | 9942107 | 8/1999 |
| WO | 0040572 | 7/2000 |
| WO | WO0076993 | 12/2000 |
| WO | 0122963 | 4/2001 |
| WO | WO0151919 | 7/2001 |
| WO | 0202522 | 1/2002 |
| WO | 0208221 | 1/2002 |
| WO | WO02051781 | 7/2002 |
| WO | 02068409 | 9/2002 |
| WO | 03004480 | 1/2003 |
| WO | WO03014110 | 2/2003 |
| WO | 03103666 | 12/2003 |
| WO | 2004037769 | 5/2004 |
| WO | 2004046110 | 6/2004 |
| WO | 2004055010 | 7/2004 |
| WO | 2004099156 | 11/2004 |
| WO | 2005028475 | 3/2005 |
| WO | 2005058884 A2 | 6/2005 |
| WO | 2006014168 | 2/2006 |
| WO | WO2006028290 | 3/2006 |
| WO | 2006040192 | 4/2006 |
| WO | WO2006036015 | 4/2006 |
| WO | 2006071730 | 7/2006 |
| WO | 2006079916 | 8/2006 |
| WO | 2006088075 | 8/2006 |
| WO | WO2006087169 | 8/2006 |
| WO | 2006100591 | 9/2006 |
| WO | 2006103544 | 10/2006 |
| WO | 2006103545 | 10/2006 |
| WO | 2006103555 | 10/2006 |
| WO | 2007011623 | 1/2007 |
| WO | WO2007011065 | 1/2007 |
| WO | 2007016496 | 2/2007 |
| WO | WO2007035425 | 3/2007 |
| WO | 2007049123 | 5/2007 |
| WO | 2007053386 | 5/2007 |
| WO | 2007075895 | 7/2007 |
| WO | 2007076140 | 7/2007 |
| WO | 2007098536 | 9/2007 |
| WO | WO2007105729 | 9/2007 |
| WO | 2007111921 | 10/2007 |
| WO | 2007150010 | 12/2007 |
| WO | 2008003702 | 1/2008 |
| WO | 2008024284 | 2/2008 |
| WO | WO2008064817 | 6/2008 |
| WO | WO2008075068 | 6/2008 |
| WO | 2008147864 | 12/2008 |
| WO | 2008150364 | 12/2008 |
| WO | WO2008151957 | 12/2008 |
| WO | 2009024823 | 2/2009 |
| WO | WO2009109594 | 9/2009 |
| WO | WO2009135842 | 11/2009 |
| WO | WO2010012650 | 2/2010 |
| WO | WO2010096011 | 8/2010 |
| WO | 2011102793 | 8/2011 |
| WO | 2011102794 | 8/2011 |
| WO | 2011102795 | 8/2011 |

OTHER PUBLICATIONS

Watanabe, Mizuki et al., Poster "Development of potent histamine H3/H4 receptor ligands by the stereochemical diversity-oriented chiral cyclopropane-based conformational restriction strategy," Presented at 234th ACS National Meeting held in Boston Aug. 19-23, 2007.

Watanabe et al., "Investigation of the Bioactive Conformation of Histamine H3 Receptor Antagonists by the Cyclopropylic Strain-Based Conformational Restriction Strategy," J. Med. Chem. 2010, vol. 53, pp. 3585-3593.

Wijtmans et al., "Histamine H3 receptor ligands break ground in a remarkable plethora of therapeutic areas," Expert Opin. Investig. Drugs, 2007, vol. 16(7), pp. 967-985.

Yamaguchi et al., "Construction of a cis-Cyclopropane via Reductive Radical Decarboxylation. Enantioselective Synthesis of cis- and trans-1-Arylpiperazyl-2-phenylcyclopropanes Designed as Antidopaminergic Agents," J. Org. Chem., 2003, vol. 68, No. 24, pp. 9255-9262.

Zhang et al., "trans-1-[(2-Phenylcyclopropyl)methyl]-4-arylpiperazines: Mixed Dopamine D2/D4 Receptor Antagonists as Potential Antipsychotic Agents," J. Med. Chem., 2000, vol. 43, pp. 3923-3932.

English abstract of SU 1297727, (1985).

English abstract of UZ 3306, (Mar. 31, 2007).

International Search Report issued for PCT/SE20101050191 on May 5, 2010.

Notice of Allowance issued for U.S. Appl. No. 12/195,454 on May 27, 2010.

Notice of Allowance issued for U.S. Appl. No. 12/195,454 on Jul. 15, 2011.

API form screening and selection in drug discovery stage, Pharm Stage, v. 6, No. 10, 2007, pp. 20-25.

Armarego et al. "Purification of Laboratory Chemicals", 5th Ed., Chapter 1, pp. 1-30, © 2003, Elsevier, Cornwall, GB.

Becke, "Density-functional thermochemistry. III. The role of exact exchange," J. Chem. Phys. 1993, 98(7), pp. 5648-5652.

Brittain et al., "Polymorphism in pharmaceutical solids," (1999) chapter 6, p. 236.

Byrn et al., "Pharmaceutical Solids: A Strategic Approach to Regulatory Considerations," Pharmaceutical Research, (1995), vol. 12, No. 7, pp. 945-954.

Caira, "Crystalline Polymorphism of Organic Compounds," Topics in Current Chemistry, Springer, Berlin, DE, vol. 198, Jan. 1, 1998, pp. 163-208.

Cho et al., "Convenient synthesis of optically active 1,2-diol monosulfonates and terminal epoxides via oxazaborolidine-catalyzed asymmetric borane reduction of α-sulfonyloxy ketones," J. Chem. Soc., Perkin Trans. 1, 2001, pp. 1204-1211.

Crystallization of Polymorphs and Pseudo-polymorphs and Its Control, Pharm Stage, v. 6, No. 10, 2007 pp. 48-53.

Gennaro, "Remimgton Farmacia", Tome 2, Edition 19, Editorial Médica Panamericana, 1998, p. 2226, col. right and p. 2228, col. Left and right.

Gillaspy et. al., "A Simple Method for the Formation of Cyclopropylamines: The First Synthesis of Tricyclopropylamine," Tetrahedron Lett. 1995, 36 (41), pp. 7399-7402.

Halebian et al., "Pharmaceutical Applications of Polymorphism," J. Pharm. Sci. 1969, vol. 58, pp. 911-929, esp. p. 913.

Hamada et al., "A practical synthesis of optically active aromatic epoxides via asymmetric transfer hydrogenation of α-chlorinated ketones with chiral rhodium-diamine catalyst," Tetrahedron (2004), 60(34), pp. 7411-7417.

Hamada et al., "Practical Synthesis of Optically Active Styrene Oxides via Reductive Transformation of 2-Chloroacetophenones with Chiral Rhodium Catalysts," Organic Letters (2002), 4(24), pp. 4373-4376.

Hariharan et al., "The Influence of Polarization Functions on Molecular Orbital Hydrogenation Energies," Theor. Chim. Acta, 1973, 28, pp. 213-222.

Hickey et al, "Hydrates and Solid-State Reactivity: A Survey of β-Lactam Antibiotics," Journal Of Pharmaceutical Sciences, vol. 96, No. 5, May 2007, pp. 1090-1099.

Jain et al., "Polymorphism in Pharmacy," Indian Drugs, (1986), vol. 23(6), pp. 315-329.

Ji, "The Histamine H3-receptor Ligands: Potential Therapeutic Uses," Pharm Care & Res, Sep. 2004, 4(3), pp. 183-187 (with English abstract).

Kawaguchi et al., "Drug and Crystal Polymorphism," Life Engineering, 2002, v. 4, pp. 310-317.

Lee et al., "Development of the Colle-Salvetti correlation-energy formula into a functional of the electron density," Phys. Rev. B, 1988, 37(2), pp. 785-789.

Luo et al, "Research Progress of Histamine H3 Receptor and Its Relationship with Neurological Diseases," Acta Academiae Medicinae Zunyi, vol. 28, No. 6, Dec. 2005, pp. 569-571.

(56) References Cited

OTHER PUBLICATIONS

Newman et al., "Solid-state analysis of the active pharmaceutical ingredient in drug product," Drug discovery today, (2003), vol. 8, No. 19, pp. 898-905.
Ohkuma et al., "Asymmetric Hydrogenation of α-Chloro Aromatic Ketones Catalyzed by η6-Arene/TsDPEN-Ruthenium(II) Complexes," Organic Letters (2007), 9(2), pp. 255-257.
Pierson et al., "4-Hydroxyindole-2-carboxylic Acid Amides: Novel Histamine-3 Receptor Inverse Agonists for the Treatment of Obesity," J. Med. Chem. 2009, 52, pp. 3855-3868.
Pikal et al, "The Stability of Insulin in Crystalline and Amorphous Solids: Observation of Greater Stability for the Amorphous Form," Pharm. Res. 1997, vol. 14, pp. 1379-1387, esp. p. 1379.
Polymorphism in pharmaceutical solids, edited by H. G. Brittain, Marcel Dekker, D.J.W. (1999), Grant (chapter 1) p. 1-10; and Guillory (chapter 5) p. 183-226.
Report by the Council on Medical Service Facilities No. 568, 2001.
Singh et al., "Development of a Practical, Safe, and High-Yielding Process for the Preparation of Enantiomerically Pure trans-Cyclopropane Carboxylic Acid," Organic Process Research & Development 2002, 6, pp. 618-620.
Singhal et al., "Drug Polymorphism and Dosage Form Design: A Practical Perspective," Advanced Drug Delivery Review, vol. 56, pp. 335-347, 2004.
Wisdom et al., "Enzymatic synthesis of carbo-and heterocyclic aryl oxiranes," Speciality Chemicals Magazine, 27(8), 32-33(2007).
Wu et al., "Research Progress of Histamine H3 Receptor Ligands," Chin Pharm J. Mar. 2007, vol. 42, No. 6, pp. 404-409.
Yamano, "Approach to Crystal Polymorph in Process Research of New Drug," J. Synth. Org. Chem., Jpn. v. 65, No. 9, 2007, pp. 907-913.
Zaragoza et al., "1-Alkyl-4-acylpiperazines as a New Class of Imidazole-Free Histamine H3 Receptor Antagonists," J. Med. Chem. 2004, 47, pp. 2833-2838.

\* cited by examiner

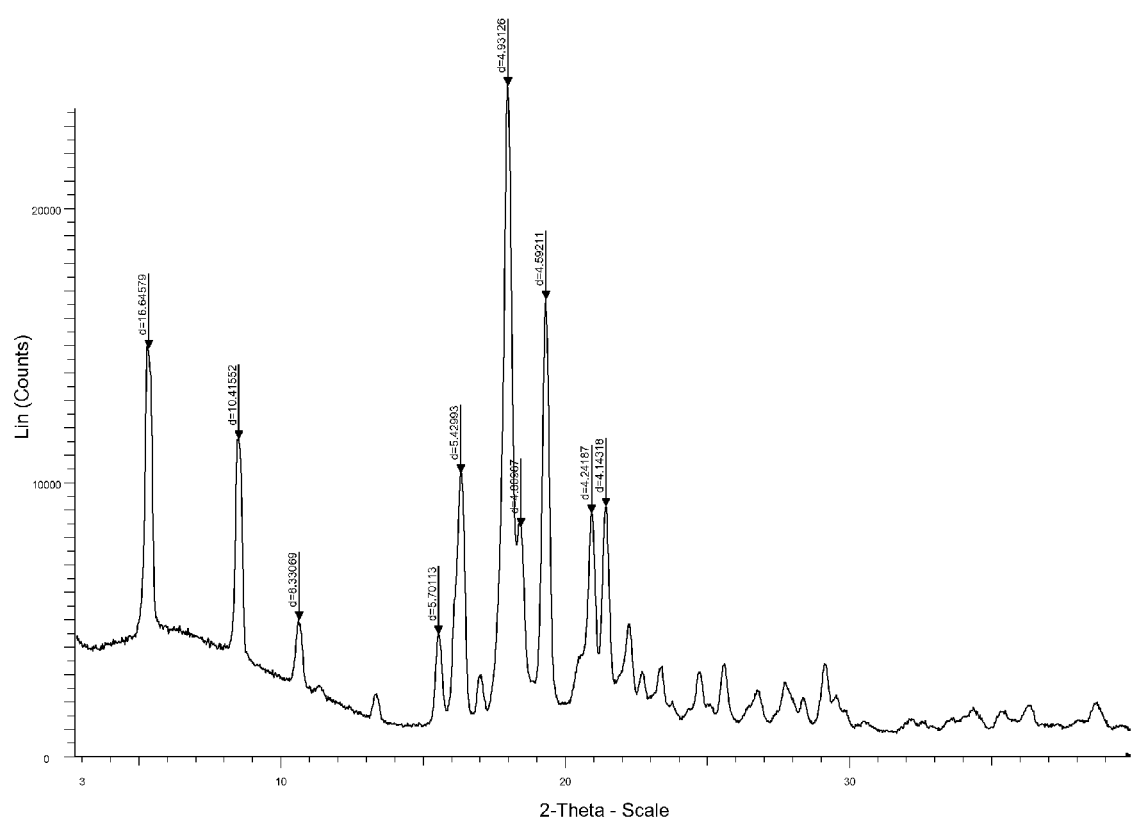

CYCLOPROPYL AMIDE DERIVATIVES

CROSS-REFERENCE TO RELATED APPLICATIONS

This application claims the benefit under 35 U.S.C. §119 (e) to U.S. Application No. 61/154,067, filed 20 Feb. 2009.

Disclosed herein is at least one cyclopropyl amide derivative, at least one pharmaceutical composition comprising at least one cyclopropyl amide derivative disclosed herein, and at least one method of using at least one cyclopropyl amide derivative disclosed herein for treating at least one histamine H3 receptor associated condition therewith.

The histamine H3 receptor is of current interest in developing new medicaments. The H3 receptor is a presynaptic autoreceptor located both in the central and peripheral nervous systems, the skin, and in organs, such as, for example, the lung, the intestine, probably the spleen, and the gastrointestinal tract. Recent evidence suggests the H3 receptor has intrinsic, constitutive activity in vitro as well as in vivo (i.e., it is active in the absence of an agonist). Compounds acting as inverse agonists can inhibit this activity. The histamine H3 receptor has been shown to regulate the release of histamine and also of other neurotransmitters, such as, for example, serotonin and acetylcholine. Some histamine H3 ligands, such as, for example, a histamine H3 receptor antagonist or inverse agonist may increase the release of neurotransmitters in the brain, whereas other histamine H3 ligands, such as, for example, histamine H3 receptor agonists may inhibit the biosynthesis of histamine, as well as, inhibit the release of neurotransmitters. This suggests that histamine H3 receptor agonists, inverse agonists, and antagonists could mediate neuronal activity. As a result, efforts have been undertaken to develop new therapeutics that target the histamine H3 receptor.

BRIEF DESCRIPTION OF DRAWINGS

FIG. 1 shows an X-ray powder diffraction (XRPD) pattern for Example 35 (Crystalline Form I).

Described herein are compounds of formula I, or enantiomers or diastereomers thereof, or pharmaceutically acceptable salts of formula I or enantiomers or diastereomers thereof, or mixtures thereof:

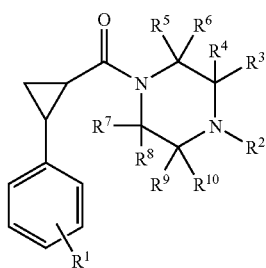

I wherein:

$R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2NR^{11}R^{12}$, heterocycle, cyano, haloalkyl, —C(=O)$NR^{11}R^{12}$, alkoxy, or halogen;

$R^2$ is $C_1$-$C_6$alkyl or $C_3$-$C_6$cycloalkyl;

$R^3$, $R^4$, $R^5$, $R^6$, $R^7$, $R^8$, $R^9$, and $R^{10}$ are each independently selected from H and $C_{1-3}$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —($C_1$-$C_3$alkyl)-(5-membered heteroaryl containing at least one heteroatom selected from O and N), —($C_1$-$C_3$alkyl)-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and provided:
i) at least one of $R^3$, $R^4$, $R^5$, $R^6$, $R^7$, $R^8$, $R^9$, and $R^{10}$ is a $C_1$-$C_3$alkyl;
ii) formula I is not

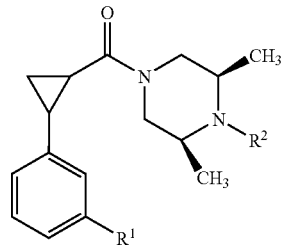

when $R^1$ is a —C(=O)$NR^{11}R^{12}$ group meta attached to the phenyl, $R^2$ is isopropyl, and $R^{11}$ and $R^{12}$ are H; and
iii) formula I is not in the cis configuration at the cyclopropane.

Further described herein are compounds according to formula I, or diastereomers or enantiomers thereof, or pharmaceutically acceptable salts of formula I or diastereomers or enantiomers thereof, or mixtures thereof for use as a medicament.

Even further described herein is the use of compounds of formula I, or diastereomers or enantiomers thereof, or pharmaceutically acceptable salts of formula I or diastereomers or enantiomers thereof, or mixtures thereof in the manufacture of a medicament for the therapy of at least one disorder selected from cognitive deficit in schizophrenia, narcolepsy, obesity, attention deficit hyperactivity disorder, pain, and Alzheimer's disease.

Still further described herein is the use of compounds of formula I, or diastereomers or enantiomers thereof, or pharmaceutically acceptable salts of formula I or diastereomers or enantiomers thereof, or mixtures thereof in the manufacture of a medicament for the therapy of at least one disorder selected from cognitive deficit in schizophrenia, narcolepsy, obesity, attention deficit hyperactivity disorder, pain, and Alzheimer's disease.

Yet even further described herein is a pharmaceutical composition comprising at least one compound according to formula I, or diastereomers or enantiomers thereof, or pharmaceutically acceptable salts of formula I or diastereomers or enantiomers thereof, or mixtures thereof and a pharmaceutically acceptable carrier and/or diluent.

Still even further described herein is a method for treating at least one disorder selected from cognitive deficit in schizophrenia, narcolepsy, obesity, attention deficit hyperactivity disorder, pain, and Alzheimer's disease in a warm-blooded animal, comprising administering to said animal in need of such treatment a therapeutically effective amount of at least one compound according to formula I, or diastereomers or enantiomers thereof, or pharmaceutically acceptable salts of formula I or diastereomers or enantiomers thereof, or mixtures thereof.

Still yet even further described herein is a method for treating a disorder in which modulating the histamine H3 receptor is beneficial comprising administering to a warm-blooded animal in need of such treatment a therapeutically effective amount of at least one compound according to formula I, or diastereomers or enantiomers thereof, or pharmaceutically acceptable salts of formula I or diastereomers or enantiomers thereof, or mixtures thereof.

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

Unless specifically stated otherwise herein, references made in the singular may also include the plural. For example, "a" and "an" may refer to either one, or one or more.

Embodiments identified herein as exemplary are intended to be illustrative and not limiting.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Definitions of terms used in describing the invention are set forth hereinbelow. Unless otherwise indicated, the initial definition provided for a group or term applies each time such group or term is used individually or as part of another group.

Throughout the specification, groups and substituents thereof may be chosen by one skilled in the field to provide stable moieties and compounds.

The term "$C_m$-$C_n$" or "$C_m$-$C_n$ group" used alone or as a prefix, refers to any group having m to n carbon atoms. For example, the term "$C_1$-$C_4$alkyl" refers to an alkyl group containing 1, 2, 3, or 4 carbon atoms.

The terms "alkyl" and "alk" refer to a straight or branched chain alkane (hydrocarbon) radical containing from 1 to 12 carbon atoms. Exemplary "alkyl" and "alk" groups include, but are not limited to, for example, methyl; ethyl; propyl; isopropyl; 1-methylpropyl; n-butyl, t-butyl; isobutyl; pentyl; hexyl; isohexyl; heptyl; 4,4-dimethylpentyl; diethylpentyl; octyl; 2,2,4-trimethylpentyl; nonyl; decyl; undecyl; and dodecyl.

The term "hydrocarbon" refers to a chemical structure comprising only carbon and hydrogen atoms.

The term "hydrocarbon radical" refers to a hydrocarbon that has had at least one hydrogen removed therefrom.

The term "aryl" refers to monocyclic or bicyclic aromatic hydrocarbon rings having from 6 to 12 carbon atoms in the ring portion. Exemplary aryl groups include but are not limited to, for example, phenyl; phen-1-yl-2-yl; phen-1-yl-3-yl; phen-1-yl-4-yl; phen-1-yl-5-yl; phen-1-yl-6-yl; naphthalenyl; naphthalen-1-yl-2-yl; naphthalen-1-yl-3-yl; naphthalen-1-yl-4-yl; naphthalen-1-yl-5-yl; naphthalen-1-yl-6-yl; naphthalen-1-yl-7-yl; naphthalen-1-yl-8-yl; naphthalen-2-yl-3-yl; naphthalen-2-yl-4-yl; naphthalen-2-yl-5-yl; naphthalen-2-yl-6-yl; naphthalen-2-yl-7-yl; naphthalen-2-yl-8-yl; naphthalen-3-yl-4-yl; naphthalen-3-yl-5-yl; naphthalen-3-yl-6-yl; naphthalen-3-yl-7-yl; naphthalen-3-yl-8-yl; naphthalen-4-yl-5-yl; naphthalen-4-yl-6-yl; naphthalen-4-yl-7-yl; naphthalen-4-yl-8-yl; naphthalen-5-yl-6-yl; naphthalen-5-yl-7-yl; naphthalen-5-yl-8-yl; naphthalen-6-yl-7-yl; naphthalen-6-yl-8-yl; naphthalen-7-yl-8-yl; biphenyl; biphenyl-2-yl; biphenyl-3-yl; biphenyl-4-yl; biphenyl-5-yl; biphenyl-6-yl; and diphenyl. When two aromatic rings are present, the aromatic rings of the aryl group may either be joined at a single point (e.g., biphenyl), or be fused (e.g., naphthalenyl). Unless reference is made to a specific point of attachment, e.g., as in phen-1-yl-2-yl, naphthalen-1-yl-6-yl, and biphenyl-3-yl, it is intended that such aryl groups can be bonded to at least one other moiety at any available point of attachment.

The term "heteroaryl" refers to aromatic cyclic groups, such as, for example, 5- to 6-membered monocyclic ring systems having at least one heteroatom selected from O, N and S in at least one carbon atom-containing ring. The carbon atom-containing ring may contain 1, 2, 3, or 4 heteroatom(s) selected from nitrogen, oxygen, and sulfur. The heteroaryl group may be attached to another moiety at any available point of attachment.

Exemplary monocyclic heteroaryl groups include, but are not limited to, for example, pyrazolyl; pyrazol-1-yl; pyrazol-2-yl; pyrazol-3-yl; pyrazol-4-yl; pyrazol-5-yl; pyrazolylyl; pyrazol-1-yl-2-yl; pyrazol-1-yl-3-yl; pyrazol-1-yl-4-yl; pyrazol-1-yl-5-yl; pyrazol-2-yl-3-yl; pyrazol-2-yl-4-yl; pyrazol-2-yl-5-yl; pyrazol-3-yl-4-yl; pyrazol-3-yl-5-yl; pyrazol-4-yl-5-yl; imidazolyl; imidazol-1-yl; imidazol-2-yl; imidazol-3-yl; imidazol-4-yl; imidazol-5-yl; imidazolylyl; imidazol-1-yl-2-yl; imidazol-1-yl-3-yl; imidazol-1-yl-4-yl; imidazol-1-yl-5-yl; imidazol-2-yl-3-yl; imidazol-2-yl-4-yl; imidazol-2-yl-5-yl; imidazol-3-yl-4-yl; imidazol-3-yl-5-yl; imidazol-4-yl-5-yl; triazolyl; triazol-1-yl; triazol-2-yl; triazol-3-yl; triazol-4-yl; triazol-5-yl; triazolylyl; triazol-1-yl-2-yl; triazol-1-yl-3-yl; triazol-1-yl-4-yl; triazol-2-yl-3-yl; triazol-2-yl-4-yl; triazol-2-yl-5-yl; triazol-3-yl-4-yl; triazol-3-yl-5-yl; triazol-4-yl-5-yl; oxazolyl; oxazol-2-yl; oxazol-3-yl; oxazol-4-yl; oxazol-5-yl; oxazolylyl; oxazol-2-yl-3-yl; oxazol-2-yl-4-yl; oxazol-2-yl-5-yl; oxazol-3-yl-4-yl; oxazol-3-yl-5-yl; oxazol-4-yl-5-yl; furyl; fur-2-yl; fur-3-yl; fur-4-yl; fur-5-yl; furylyl; fur-2-yl-3-yl; fur-2-yl-4-yl; fur-2-yl-5-yl; fur-3-yl-4-yl; fur-3-yl-5-yl; fur-4-yl-5-yl; thiazolyl; thiazol-1-yl; thiazol-2-yl; thiazol-3-yl; thiazol-4-yl; thiazol-5-yl; thiazolylyl; thiazol-1-yl-2-yl; thiazol-1-yl-3-yl; thiazol-1-yl-4-yl; thiazol-1-yl-5-yl; thiazol-2-yl-3-yl; thiazol-2-yl-4-yl; thiazol-2-yl-5-yl; thiazol-3-yl-4-yl; thiazol-3-yl-5-yl; thiazol-4-yl-5-yl; isoxazolyl; isoxazol-2-yl; isoxazol-3-yl; isoxazol-4-yl; isoxazol-5-yl; isoxazol-2-yl-3-yl; isoxazol-2-yl-4-yl; isoxazol-2-yl-5-yl; isoxazol-3-yl-4-yl; isoxazol-3-yl-5-yl; isoxazol-4-yl-5-yl; pyridyl; pyrid-1-yl; pyrid-2-yl; pyrid-3-yl; pyrid-4-yl; pyrid-5-yl; pyrid-6-yl; pyridylyl; pyrid-1-yl-2-yl; pyrid-1-yl-3-yl; pyrid-1-yl-4-yl; pyrid-1-yl-5-yl; pyrid-1-yl-6-yl; pyrid-2-yl-3-yl; pyrid-2-yl-4-yl; pyrid-2-yl-5-yl; pyrid-2-yl-6-yl; pyrid-3-yl-4-yl; pyrid-3-yl-5-yl; pyrid-3-yl-6-yl; pyrid-4-yl-5-yl; pyrid-4-yl-6-yl; pyrid-5-yl-6-yl; pyridazinyl; pyridazin-1-yl; pyridazin-2-yl; pyridazin-3-yl; pyridazin-4-yl; pyridazin-5-yl; pyridazin-6-yl; pyridazinylyl; pyridazin-1-yl-2-yl; pyridazin-1-yl-3-yl; pyridazin-1-yl-4-yl; pyridazin-1-yl-5-yl; pyridazin-1-yl-6-yl; pyridazin-2-yl-3-yl; pyridazin-2-yl-4-yl; pyridazin-2-yl-5-yl; pyridazin-2-yl-6-yl; pyridazin-3-yl-4-yl; pyridazin-3-yl-5-yl; pyridazin-3-yl-6-yl; pyridazin-4-yl-5-yl; pyridazin-4-yl-6-yl; pyridazin-5-yl-6-yl; pyrimidinyl; pyrimidin-1-yl; pyrimidin- 2-yl; pyrimidin-3-yl; pyrimidin-4-yl; pyrimidin-5-yl; pyrimidin-6-yl; pyrimidinylyl; pyrimidin-1-yl-2-yl; pyrimidin-1-yl-3-yl; pyrimidin-1-yl-4-yl; pyrimidin-1-yl-5-yl; pyrimidin-1-yl-6-yl; pyrimidin-2-yl-3-yl; pyrimidin-2-yl-4-yl; pyrimidin-2-yl-5-yl; pyrimidin-2-yl-6-yl; pyrimidin-3-yl-4-yl; pyrimidin-3-yl-5-yl; pyrimidin-3-yl-6-yl; pyrimidin-4-yl-5-yl; pyrimidin-4-yl-6-yl; pyrimidin-5-yl-6-yl; pyrazinyl; pyrazin-1-yl; pyrazin-2-yl; pyrazin-3-yl; pyrazin-4-yl; pyrazin-5-yl; pyrazin-6-yl; pyrazinylyl; pyrazin-1-yl-2-yl; pyrazin-1-yl-3-yl; pyrazin-1-yl-4-yl; pyrazin-1-yl-5-yl; pyrazin-1-yl-6-yl; pyrazin-2-yl-3-yl; pyrazin-2-yl-4-yl; pyrazin-2-yl-5-yl; pyrazin-2-yl-6-yl; pyrazin-3-yl-4-yl; pyrazin-3-yl-5-yl; pyrazin-3-yl-6-yl; pyrazin-4-yl-5-yl; pyrazin-4-yl-6-yl; pyrazin-5-yl-6-yl; triazinyl; triazin-1-yl; triazin-2-yl; triazin-3-yl; triazin-4-yl; triazin-5-yl; triazin-6-yl; triazinylyl; triazin-1-yl-2-yl; triazin-1-yl-3-yl; triazin-1-yl-4-yl; triazin-1-yl-5-yl; triazin-1-yl-6-yl; triazin-2-yl-3-yl; triazin-2-yl-4-yl; triazin-2-yl-5-yl; triazin-2-yl-6-yl; triazin-3-yl-4-yl; triazin-3-yl-5-yl; triazin-3-yl-6-yl; triazin-4-yl-5-yl; triazin-4-yl-6-yl; and triazin-5-yl-6-yl. Unless reference is made to a specific point of attachment, e.g., as in pyrid-2-yl, pyridazin-3-yl, it is intended that such heteroaryl groups can be bonded to at least one other moiety at any available point of attachment.

The term "cycloalkyl" refers to a fully saturated and partially unsaturated cyclic hydrocarbon group containing from 3 to 8 carbons. Exemplary cycloalkyls include, but are not limited to, for example, cyclopropyl; cyclopropylyl; cycloprop-1-yl-2-yl; cyclobutyl; cyclobutylyl; cyclobut-1-yl-2-yl; cyclobut-1-yl-3-yl; cyclopentyl; cyclopentylyl; cyclopent-1-yl-2-yl; cyclopent-1-yl-3-yl; cyclohexyl; cyclohexylyl; cyclohex-1-yl-2-yl; cyclohex-1-yl-3-yl; cyclohex-1-yl-4-yl; cycloheptyl; cycloheptylyl; cyclohept-1-yl-2-yl; cyclohept-1-yl-3-yl; cyclohept-1-yl-4-yl; cyclooctyl; cyclooct-1-yl-2-yl; cyclooct-1-yl-3-yl; cyclooct-1-yl-4-yl; cyclooct-1-yl-5-yl; cyclobutenyl; cyclobuten-1-yl; cyclobuten-2-yl; cyclobuten-3-yl; cyclobuten-4-yl; cyclobutenylyl; cyclobuten-1-yl-2-yl; cyclobuten-1-yl-3-yl; cyclobuten-1-yl-4-yl; cyclobuten-2-yl-3-yl; cyclobuten-2-yl-4-yl; cyclobuten-3-yl-4-yl; cyclopentenyl; cyclopenten-1-yl; cyclopenten-2-yl; cyclopenten-3-yl; cyclopenten-4-yl; cyclopenten-5-yl; cyclopentenylyl; cyclopenten-1-yl-2-yl; cyclopenten-1-yl-3-yl; cyclopenten-1-yl-4-yl; cyclopenten-1-yl-5-yl; cyclopenten-2-yl-3-yl; cyclopenten-2-yl-4-yl; cyclopenten-2-yl-5-yl; cyclopenten-3-yl-4-yl; cyclopenten-3-yl-5-yl; cyclopenten-4-yl-5-yl; cyclohexenyl; cyclohexen-1-yl; cyclohexen-2-yl; cyclohexen-3-yl; cyclohexen-4-yl; cyclohexen-5-yl; cyclohexen-6-yl; cyclohexenylyl; cyclohexen-1-yl-2-yl; cyclohexen-1-yl-3-yl; cyclohexen-1-yl-4-yl; cyclohexen-1-yl-5-yl; cyclohexen-1-yl-6-yl; cyclohexen-2-yl-3-yl; cyclohexen-2-yl-4-yl; cyclohexen-2-yl-5-yl; cyclohexen-2-yl-6-yl; cyclohexen-3-yl-4-yl; cyclohexen-3-yl-5-yl; cyclohexen-3-yl-6-yl; cyclohexen-4-yl-5-yl; cyclohexen-4-yl-6-yl; and cyclohexen-5-yl-6-yl. A cycloalkyl ring may have a carbon ring atom replaced with a carbonyl group (C=O). Unless reference is made to a specific point of attachment, e.g. as in cyclohexen-3-yl-6-yl, cycloprop-1-yl-2-yl, and cyclobuten-4-yl, it is intended that such cycloalkyl groups can be bonded to at least one other moiety at any available point of attachment.

The term "heterocycle" or "heterocyclic" refers to an optionally substituted, fully saturated or unsaturated, aromatic or nonaromatic cyclic group, which is, for example, a 4 to 7 membered monocyclic ring system containing at least one heteroatom. The heterocycle may contain 1, 2 or 3 heteroatoms selected from N, O, and S, where the N and S heteroatoms may optionally be oxidized and the N heteroatom may optionally be quaternized. The heterocycle may be attached via any heteroatom or carbon atom of the ring.

Exemplary monocyclic heterocycles/heterocyclics include, but are not limited to, for example, pyrrolidinyl; pyrrolidinylyl; pyrrolyl; pyrrolylyl; indolyl; indolylyl; pyrazolyl; pyrazolylyl; oxetanyl; oxetanylyl; pyrazolinyl; pyrazolinylyl; imidazolyl; imidazolylyl; imidazolinyl; imidazolinylyl; imidazolidinyl; imidazolidinylyl; oxazolyl; oxazolylyl; oxazolidinyl; oxazolidinylyl; isoxazolinyl; isoxazolinylyl; isoxazolyl; isoxazolylyl; thiazolyl; thiazolylyl; thiadiazolyl; thiadiazolylyl; thiazolidinyl; thiazolidinylyl; isothiazolyl; isothiazolylyl; isothiazolidinyl; isothiazolidinylyl; furyl; furylyl; tetrahydrofuryl; tetrahydrofurylyl; thienyl; thienylyl; oxadiazolyl; oxadiazolylyl; piperidinyl; piperidinylyl; piperazinyl; piperazinylyl; 2-oxopiperazinyl; 2-oxopiperazinylyl; 2-oxopiperidinyl; 2-oxopiperidinylyl; homopiperazinyl; homopiperazinylyl; 2-oxohomopiperazinyl; 2-oxohomopiperazinylyl; 2-oxopyrrolidinyl; 2-oxopyrrolidinylyl; 2-oxazepinyl; 2-oxazepinylyl; azepinyl; azepinylyl; 4-piperidinyl; 4-piperidinylyl; pyridyl; pyridylyl; N-oxo-pyridyl; N-oxo-pyridylyl; pyrazinyl; pyrazinylyl; pyrimidinyl; pyrimidinylyl; pyridazinyl; pyridazinylyl; tetrahydropyranyl; tetrahydropyranylyl; morpholinyl; morpholinylyl; thiamorpholinyl; thiamorpholinylyl; 1,3-dioxolanyl; 1,3-dioxolanylyl; tetrahydro-1,1-dioxothienyl; tetrahydro-1,1-dioxothienylyl; dioxanyl; dioxanylyl; isothiazolidinyl; isothiazolidinylyl; thietanyl; thietanylyl; thiiranyl; thiiranylyl; triazinyl; triazinylyl; triazolyl; and triazolylyl.

The term "heterocycloalkyl" refers to a saturated or unsaturated cycloalkyl in which at least one ring carbon (and any associated hydrogen atoms) are independently replaced with at least one heteroatom selected from O and N.

The terms "halogen" and "halo" refer to chlorine, bromine, fluorine, and iodine.

The term "haloalkyl" refers to a $C_1$-$C_3$alkyl bonded to a single halogen or multiple halogens. Exemplary haloalkyls containing multiple halogens include, but are not limited to, for example, —$CHCl_2$, —$CH_2$—$CHF_2$, and —$CF_3$.

The term "alkoxy" used alone or as a suffix or prefix, refers to radicals of the general formula —$OR^a$, wherein $R^a$ is selected from a hydrocarbon radical. Exemplary alkoxys include, but are not limited to, for example, methoxy, ethoxy, propoxy, isopropoxy, butoxy, t-butoxy, isobutoxy, cyclopropylmethoxy, allyloxy, and propargyloxy.

The term "cyano" refers to CN.

The phrase "optionally substituted" refers to groups, structures, or molecules that are substituted with at least one substituent at any available and substitutable position and groups, structures, or molecules that are not substituted.

The phrase "a compound of formula [insert formula number used in connection with a specific formula described herein], or enantiomers or diastereomers thereof, or pharmaceutically acceptable salts of formula [insert formula number used in connection with a specific formula described herein] or enantiomers or diastereomers thereof, or mixtures thereof" refers to the free base of formula [insert formula number used in connection with a specific formula described herein], enantiomers of the free base of formula [insert formula number used in connection with a specific formula described herein], diastereomers of the free base of formula [insert formula number used in connection with a specific formula described herein], pharmaceutically acceptable salts of formula [insert formula number used in connection with a specific formula described herein], pharmaceutically acceptable salts of the enantiomers of formula [insert formula number used in connection with a specific formula described herein], pharmaceutically acceptable salts of the diastereomers of formula [insert formula number used in connection with a specific formula described herein], and/or mixtures of any of the foregoing. The formula number inserted where says "[insert formula number used in connection with a specific formula described herein]" is selected from the formula numbers described herein and once selected is inserted into each bracket such that is consistent throughout the phrase and explanation provided therefore. For example, if formula I is selected for insertion into the bracket, the phrase reads "a compound of formula [I], or enantiomers or diastereomers thereof, or pharmaceutically acceptable salts of formula [I] or enantiomers or diastereomers thereof, or mixtures thereof", and the explanation provided therefor reads: "refers to the free base of formula [I], enantiomers of the free base of formula [I], diastereomers of the free base of formula [I], pharmaceutically acceptable salts of formula [I], pharmaceutically acceptable salts of the enantiomers of formula [I], pharmaceutically acceptable salts of the diastereomers of formula [I], and/or mixtures of any of the foregoing."

The phrase "a compound of formula [insert formula number used in connection with a specific formula described herein], or enantiomers thereof, or pharmaceutically acceptable salts of formula [insert formula number used in connection with a specific formula described herein] or enantiomers thereof, or mixtures thereof" refers to the free base of formula [insert formula number used in connection with a specific formula described herein], enantiomers of the free base of formula [insert formula number used in connection with a specific formula described herein], pharmaceutically acceptable salts of formula [insert formula number used in connection with a specific formula described herein], pharmaceutically acceptable salts of the enantiomers of formula [insert formula number used in connection with a specific formula described herein], and/or mixtures of any of the foregoing. The formula number inserted where says "[insert formula number used in connection with a specific formula described herein]" is selected from the formula numbers described herein and once selected is inserted into each bracket such that is consistent throughout the phrase and explanation provided therefore. For example, if formula I is selected for insertion into the bracket, the phrase reads "a compound of formula [I], or enantiomers thereof, or pharmaceutically acceptable salts of formula [I] or enantiomers thereof, or mixtures thereof", and the explanation provided therefor reads: "refers to the free base of formula [I], enantiomers of the free base of formula [I], pharmaceutically acceptable salts of formula [I], pharmaceutically acceptable salts of the enantiomers of formula [I], and/or mixtures of any of the foregoing."

In one aspect, the disclosure provides a compound of formula I, or enantiomers or diastereomers thereof, or pharmaceutically acceptable salts of formula I or enantiomers or diastereomers thereof, or mixtures thereof:

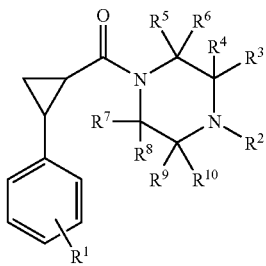

I wherein:
$R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2NR^{11}R^{12}$, heterocycle, cyano, haloalkyl, —C(=O)$NR^{11}R^{12}$, alkoxy, or halogen;
$R^2$ is $C_1$-$C_6$alkyl or $C_3$-$C_6$cycloalkyl;
$R^3$, $R^4$, $R^5$, $R^6$, $R^7$, $R^8$, $R^9$, and $R^{10}$ are each independently selected from H and $C_1$-$C_3$alkyl; and
$R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —($C_1$-$C_3$alkyl)-(5-membered heteroaryl containing at least one heteroatom selected from O and N), —($C_1$-$C_3$alkyl)-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and provided:
i) at least one of $R^3$, $R^4$, $R^5$, $R^6$, $R^7$, $R^8$, $R^9$, and $R^{10}$ is a $C_1$-$C_3$alkyl;
ii) formula I is not

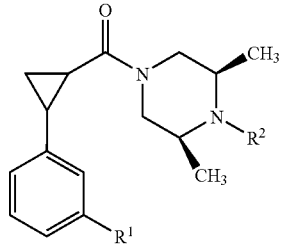

when $R^1$ is a —C(=O)$NR^{11}R^{12}$ group meta attached to the phenyl, $R^2$ is isopropyl, and $R^{11}$ and $R^{12}$ are H; and
iii) formula I is not in the cis configuration at the cyclopropane.

In another aspect, the disclosure provides a compound of formula Ia, or enantiomers or diastereomers thereof, or pharmaceutically acceptable salts of formula Ia or enantiomers or diastereomers thereof, or mixtures thereof:

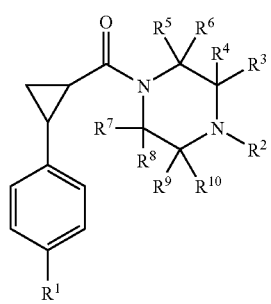

Ia wherein:
$R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)$_2NR^{11}R^{12}$, —S(=O)$_2NR^{11}R^{12}$, heterocycle, cyano, haloalkyl, —C(=O)$NR^{11}R^{12}$, alkoxy, or halogen;
$R^2$ is $C_1$-$C_6$alkyl or $C_3$-$C_6$cycloalkyl;

$R^3$, $R^4$, $R^5$, $R^6$, $R^7$, $R^8$, $R^9$, and $R^{10}$ are each independently selected from H and $C_1$-$C_3$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —($C_1$-$C_3$alkyl)-(5-membered heteroaryl containing at least one heteroatom selected from O and N), —($C_1$-$C_3$alkyl)-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and provided:
i) at least one of $R^3$, $R^4$, $R^5$, $R^6$, $R^7$, $R^8$, $R^9$, and $R^{10}$ is a $C_1$-$C_3$alkyl; and
ii) formula Ia is not in the cis configuration at the cyclopropane.

In still another aspect, the disclosure provides a compound of formula Ib, or enantiomers or diastereomers thereof, or pharmaceutically acceptable salts of formula Ib or enantiomers or diastereomers thereof, or mixtures thereof:

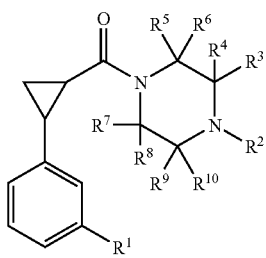

Ib wherein:
$R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2NR^{11}R^{12}$, heterocycle, cyano, haloalkyl, —C(=O)$NR^{11}R^{12}$, alkoxy, or halogen;

$R^2$ is $C_1$-$C_6$alkyl or $C_3$-$C_6$cycloalkyl;

$R^3$, $R^4$, $R^5$, $R^6$, $R^7$, $R^8$, $R^9$, and $R^{10}$ are each independently selected from H and $C_1$-$C_3$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —($C_1$-$C_3$alkyl)-(5-membered heteroaryl containing at least one heteroatom selected from O and N), —($C_1$-$C_3$alkyl)-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and provided:
i) at least one of $R^3$, $R^4$, $R^5$, $R^6$, $R^7$, $R^8$, $R^9$, and $R^{10}$ is a $C_1$-$C_3$alkyl;
ii) formula Ib is not

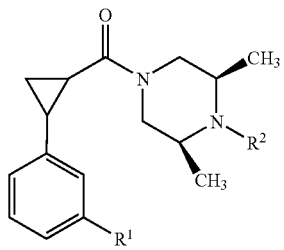

when $R^1$ is —C(=O)$NR^{11}R^{12}$, $R^2$ is isopropyl, and $R^{11}$ and $R^{12}$ are H; and iii) formula Ib is not in the cis configuration at the cyclopropane.

In yet another aspect, the disclosure provides a compound of formula II, or enantiomers or diastereomers thereof, or pharmaceutically acceptable salts of formula II or enantiomers or diastereomers thereof, or mixtures thereof:

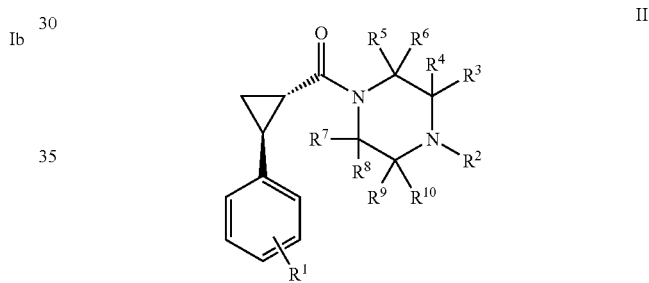

II wherein:
$R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2NR^{11}R^{12}$, heterocycle, cyano, haloalkyl, —C(=O)$NR^{11}R^{12}$, alkoxy, or halogen;

$R^2$ is $C_1$-$C_6$alkyl or $C_3$-$C_6$cycloalkyl;

$R^3$, $R^4$, $R^5$, $R^6$, $R^7$, $R^8$, $R^9$, and $R^{10}$ are each independently selected from H and $C_1$-$C_3$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —($C_1$-$C_3$alkyl)-(5-membered heteroaryl containing at least one heteroatom selected from O and N), —($C_1$-$C_3$alkyl)-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and provided:
i) at least one of $R^3$, $R^4$, $R^5$, $R^6$, $R^7$, $R^8$, $R^9$, and $R^{10}$ is a $C_1$-$C_3$alkyl; and
ii) formula II is not

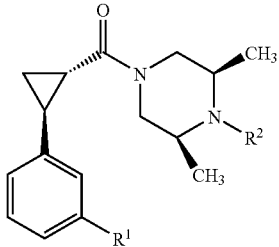

when $R^1$ is —C(=O)$NR^{11}R^{12}$, $R^2$ is isopropyl, and $R^{11}$ and $R^{12}$ are H.

In another aspect, the disclosure provides a compound of formula II, or enantiomers or diastereomers thereof, or pharmaceutically acceptable salts of formula IIa or enantiomers or diastereomers thereof, or mixtures thereof:

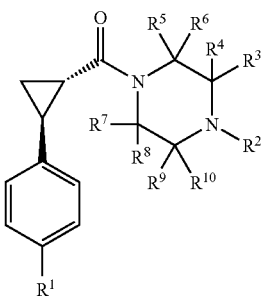

IIa wherein:
$R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2NR^{11}R^{12}$, heterocycle, cyano, haloalkyl, —C(=O)$NR^{11}R^{12}$, alkoxy, and halogen;

$R^2$ is $C_1$-$C_6$alkyl or $C_3$-$C_6$cycloalkyl;

$R^3$, $R^4$, $R^5$, $R^6$, $R^7$, $R^8$, $R^9$, and $R^{10}$ are each independently selected from H and $C_1$-$C_3$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —($C_1$-$C_3$alkyl)-(5-membered heteroaryl containing at least one heteroatom selected from O and N), —($C_1$-$C_3$alkyl)-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$ alkyl and —$C_1$-$C_6$alkyl-$C_1$-$C_3$alkoxy; and provided:
i) at least one of $R^3$, $R^4$, $R^5$, $R^6$, $R^7$, $R^8$, $R^9$, and $R^{10}$ is a $C_1$-$C_3$alkyl.

In yet still another aspect, the disclosure provides a compound of formula IIb, or enantiomers or diastereomers thereof, or pharmaceutically acceptable salts of formula IIb or enantiomers or diastereomers thereof, or mixtures thereof:

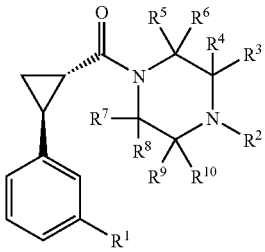

IIb wherein:
$R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2NR^{11}R^{12}$, heterocycle, cyano, haloalkyl, —C(=O)$NR^{11}R^{12}$, alkoxy, or halogen;

$R^2$ is $C_1$-$C_6$alkyl or $C_3$-$C_6$cycloalkyl;

$R^3$, $R^4$, $R^5$, $R^6$, $R^7$, $R^8$, $R^9$, and $R^{10}$ are each independently selected from H and $C_1$-$C_3$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —($C_1$-$C_3$alkyl)-(5-membered heteroaryl containing at least one heteroatom selected from O and N), —($C_1$-$C_3$alkyl)-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and provided:
i) at least one of $R^3$, $R^4$, $R^5$, $R^6$, $R^7$, $R^8$, $R^9$, and $R^{10}$ is a $C_1$-$C_3$alkyl; and
ii) formula IIb is not

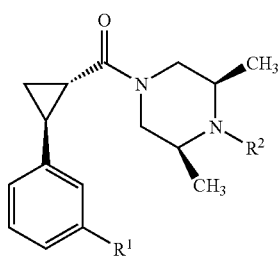

when $R^1$ is —C(=O)$NR^{11}R^{12}$, $R^2$ is isopropyl, and $R^{11}$ and $R^{12}$ are H.

In even yet another aspect, the disclosure provides a compound of formula III, or enantiomers or diastereomers thereof, or pharmaceutically acceptable salts of formula III or enantiomers or diastereomers thereof, or mixtures thereof:

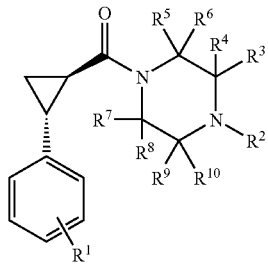

III wherein:

R¹ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2$$NR^{11}R^{12}$, heterocycle, cyano, haloalkyl, —C(=O)$NR^{11}R^{12}$, alkoxy, or halogen;

R² is $C_1$-$C_6$alkyl or $C_3$-$C_6$cycloalkyl;

R³, R⁴, R⁵, R⁶, R⁷, R⁸, R⁹, and R¹⁰ are each independently selected from H and $C_1$-$C_3$alkyl; and R¹¹ and R¹² are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —($C_1$-$C_3$alkyl)-(5-membered heteroaryl containing at least one heteroatom selected from O and N), —($C_1$-$C_3$alkyl)-(6-membered heteroaryl containing at least one heteroatom selected from O and N), haloalkyl, or R¹¹, R¹² and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and provided:

i) at least one of R³, R⁴, R⁵, R⁶, R⁷, R⁸, R⁹, and R¹⁰ is a $C_1$-$C_3$alkyl; and ii) formula III is not

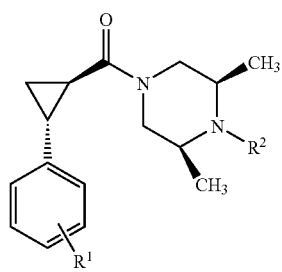

when R¹ is a —C(=O)$NR^{11}R^{12}$, R² is isopropyl, and R¹¹ and R¹² are H.

In still yet another aspect, the disclosure provides a compound of formula IIIa, or enantiomers or diastereomers thereof, or pharmaceutically acceptable salts of formula IIIa or enantiomers or diastereomers thereof, or mixtures thereof:

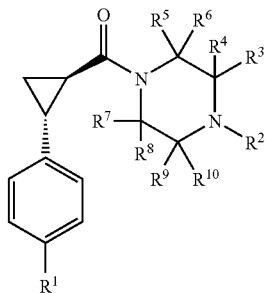

IIIa wherein:

R¹ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2$$NR^{11}R^{12}$, heterocycle, cyano, haloalkyl, —C(=O)$NR^{11}R^{12}$, alkoxy, or halogen;

R² is $C_1$-$C_6$alkyl or $C_3$-$C_6$cycloalkyl;

R³, R⁴, R⁵, R⁶, R⁷, R⁸, R⁹, and R¹⁰ are each independently selected from H and $C_1$-$C_3$alkyl; and R¹¹ and R¹² are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —($C_1$-$C_3$alkyl)-(5-membered heteroaryl containing at least one heteroatom selected from O and N), —($C_1$-$C_3$alkyl)-(6-membered heteroaryl containing at least one heteroatom selected from O and N), haloalkyl, or R¹¹, R¹² and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and provided:

i) at least one of R³, R⁴, R⁵, R⁶, R⁷, R⁸, R⁹, and R¹⁰ is a $C_1$-$C_3$alkyl.

In even still yet another aspect, the disclosure provides a compound of formula IIIb, or enantiomers or diastereomers thereof, or pharmaceutically acceptable salts of formula IIIb or enantiomers or diastereomers thereof, or mixtures thereof:

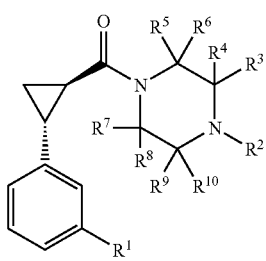

IIIb wherein:

R¹ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2$$NR^{11}R^{12}$, heterocycle, cyano, haloalkyl, —C(=O)$NR^{11}R^{12}$, alkoxy, or halogen;

R² is $C_1$-$C_6$alkyl or $C_3$-$C_6$cycloalkyl;

R³, R⁴, R⁵, R⁶, R⁷, R⁸, R⁹, and R¹⁰ are each independently selected from H and $C_1$-$C_3$alkyl; and R¹¹ and R¹² are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —(C$_1$-C$_3$alkyl)-(5-membered heteroaryl containing at least one heteroatom selected from O and N), —(C$_1$-C$_3$alkyl)-(6-membered heteroaryl containing at least one heteroatom selected from O and N), haloalkyl, or R$^{11}$, R$^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C$_1$-C$_3$alkyl and —C$_1$-C$_6$alkyl-C$_1$-C$_3$alkoxy; and provided:
i) at least one of R$^3$, R$^4$, R$^5$, R$^6$, R$^7$, R$^8$, R$^9$, and R$^{10}$ is a C$_1$-C$_3$alkyl; and
ii) formula IIIb is not

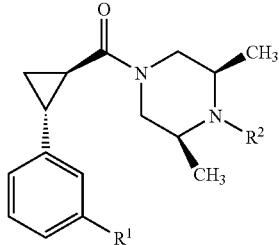

when R$^1$ is —C(=O)NR$^{11}$R$^{12}$, R$^2$ is isopropyl, and R$^{11}$ and R$^{12}$ are H.

In yet another aspect, the disclosure provides a compound of formula IV, or enantiomers or diastereomers thereof, or pharmaceutically acceptable salts of formula IV or enantiomers or diastereomers thereof, or mixtures thereof:

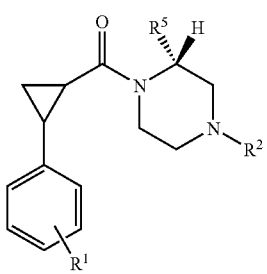

IV wherein:
R$^1$ is aryl, heteroaryl, —C$_1$-C$_6$alkyl-C$_1$-C$_3$alkoxy, —C$_1$-C$_6$alkyl-hydroxy, —C$_1$-C$_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;
R$^2$ is C$_1$-C$_6$alkyl or C$_3$-C$_6$cycloalkyl;
R$^5$ is C$_1$-C$_3$alkyl; and
R$^{11}$ and R$^{12}$ are each independently selected from H, —C$_1$-C$_6$alkyl, —C$_1$-C$_3$alkyl-C$_1$-C$_3$alkoxy, 5-membered heterocycloalkyl containing at least one heteroatom selected from O and N, 6-membered heterocycloalkyl containing at least one heteroatom selected from O and N, —C$_1$-C$_3$alkyl-(5-membered heteroaryl containing at least one heteroatom selected from O and N), —C$_1$-C$_3$alkyl-(6-membered heteroaryl containing at least one heteroatom selected from O and N), haloalkyl, or R$^{11}$, R$^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C$_1$-C$_3$alkyl and —C$_1$-C$_6$alkyl-C$_1$-C$_3$alkoxy; and provided:
i) formula IV is not in the cis configuration at the cyclopropane.

In still yet another aspect, the disclosure provides a compound of formula IVa, or enantiomers or diastereomers thereof, or pharmaceutically acceptable salts of formula IVa or enantiomers or diastereomers thereof, or mixtures thereof:

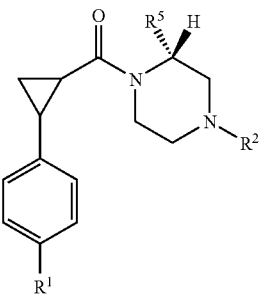

IVa wherein:
R$^1$ is aryl, heteroaryl, —C$_1$-C$_6$alkyl-C$_1$-C$_3$alkoxy, —C$_1$-C$_6$alkyl-hydroxy, —C$_1$-C$_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;
R$^2$ is C$_1$-C$_6$alkyl or C$_3$-C$_6$cycloalkyl;
R$^5$ is C$_1$-C$_3$alkyl; and
R$^{11}$ and R$^{12}$ are each independently selected from H, —C$_1$-C$_6$alkyl, —C$_1$-C$_3$alkyl-C$_1$-C$_3$alkoxy, 5-membered heterocycloalkyl containing at least one heteroatom selected from O and N, 6-membered heterocycloalkyl containing at least one heteroatom selected from O and N, —C$_1$-C$_3$alkyl-(5-membered heteroaryl containing at least one heteroatom selected from O and N), —C$_1$-C$_3$alkyl-(6-membered heteroaryl containing at least one heteroatom selected from O and N), haloalkyl, or R$^{11}$, R$^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C$_1$-C$_3$alkyl and —C$_1$-C$_6$alkyl-C$_1$-C$_3$alkoxy; and provided:
i) formula IVa is not in the cis configuration at the cyclopropane.

In even still yet another aspect, the disclosure provides a compound of formula IVb, or enantiomers or diastereomers thereof, or pharmaceutically acceptable salts of formula IVb or enantiomers or diastereomers thereof, or mixtures thereof:

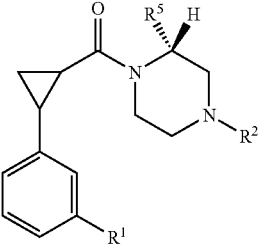

IVb wherein:
R$^1$ is aryl, heteroaryl, —C$_1$-C$_6$alkyl-C$_1$-C$_3$alkoxy, —C$_1$-C$_6$alkyl-hydroxy, —C$_1$-C$_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;

$R^2$ is $C_1$-$C_6$alkyl or $C_3$-$C_6$cycloalkyl;

$R^5$ is $C_1$-$C_3$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and provided:

i) formula IVb is not in the cis configuration at the cyclopropane.

In a further aspect, the disclosure provides a compound of formula V, or pharmaceutically acceptable salts thereof, or mixtures thereof:

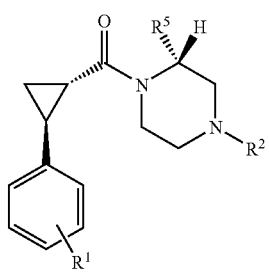

V wherein:

$R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;

$R^2$ is $C_1$-$C_6$alkyl or $C_3$-$C_6$cycloalkyl;

$R^5$ is $C_1$-$C_3$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In a still further aspect, the disclosure provides a compound of formula Va, or pharmaceutically acceptable salts thereof, or mixtures thereof:

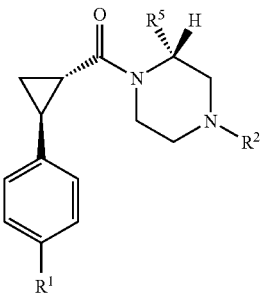

Va wherein:

$R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;

$R^2$ is $C_1$-$C_6$alkyl or $C_3$-$C_6$cycloalkyl;

$R^5$ is $C_1$-$C_3$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In yet a further aspect, the disclosure provides a compound of formula Vb, or pharmaceutically acceptable salts thereof, or mixtures thereof:

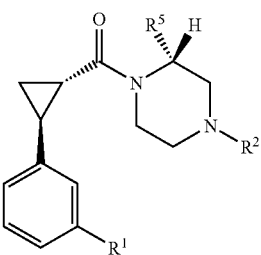

Vb wherein:

$R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;

$R^2$ is $C_1$-$C_6$alkyl or $C_3$-$C_6$cycloalkyl;

$R^5$ is $C_1$-$C_3$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or R¹¹, R¹² and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In an even further aspect, the disclosure provides a compound of formula VI, or enantiomers or diastereomers thereof, or pharmaceutically acceptable salts of formula VI or enantiomers or diastereomers thereof, or mixtures thereof:

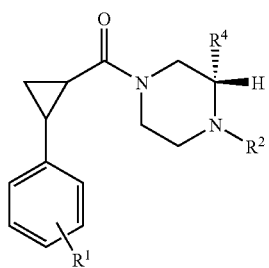

VI wherein:

R¹ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—NR¹¹R¹², —S(=O)$_2$NR¹¹R¹², heterocycle, cyano, haloalkyl, —C(=O)NR¹¹R¹², alkoxy, or halogen;

R² is $C_1$-$C_6$alkyl or $C_3$-$C_6$cycloalkyl;

R⁴ is $C_1$-$C_3$alkyl; and

R¹¹ and R¹² are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or R¹¹, R¹² and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and provided:
i) formula VI is not in the cis configuration at the cyclopropane.

In a still even further aspect, the disclosure provides a compound of formula VIa, or enantiomers or diastereomers thereof, or pharmaceutically acceptable salts of formula VIa or enantiomers or diastereomers thereof, or mixtures thereof:

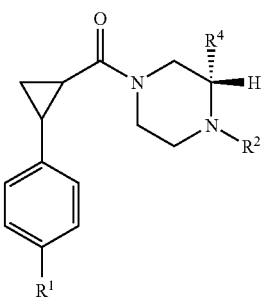

VIa wherein:

R¹ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—NR¹¹R¹², —S(=O)$_2$NR¹¹R¹², heterocycle, cyano, haloalkyl, —C(=O)NR¹¹R¹², alkoxy, or halogen;

R² is $C_1$-$C_6$alkyl or $C_3$-$C_6$cycloalkyl;

R⁴ is $C_1$-$C_3$alkyl; and

R¹¹ and R¹² are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or R¹¹, R¹² and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and provided:
i) formula VIa is not in the cis configuration at the cyclopropane.

In yet a still even further aspect, the disclosure provides a compound of formula VIb, or enantiomers or diastereomers thereof, or pharmaceutically acceptable salts of formula VIb or enantiomers or diastereomers thereof, or mixtures thereof:

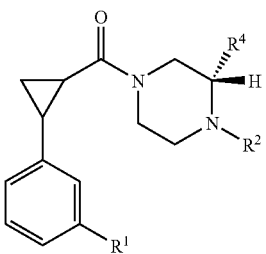

VIb wherein:

R¹ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—NR¹¹R¹², —S(=O)$_2$NR¹¹R¹², heterocycle, cyano, haloalkyl, —C(=O)NR¹¹R¹², alkoxy, or halogen;

R² is $C_1$-$C_6$alkyl or $C_3$-$C_6$cycloalkyl;

R⁴ is $C_1$-$C_3$alkyl; and

R¹¹ and R¹² are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or R¹¹, R¹² and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and provided:

i) formula VIb is not in the cis configuration at the cyclopropane.

In another aspect, the disclosure provides a compound of formula VII, or pharmaceutically acceptable salts thereof, or mixtures thereof:

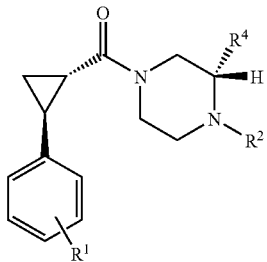

VII wherein:

$R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2NR^{11}R^{12}$, heterocycle, cyano, haloalkyl, —C(=O)$NR^{11}R^{12}$, alkoxy, or halogen;

$R^2$ is $C_1$-$C_6$alkyl or $C_3$-$C_6$cycloalkyl;

$R^4$ is $C_1$-$C_3$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In still another aspect, the disclosure provides a compound of formula VIIa, or pharmaceutically acceptable salts thereof, or mixtures thereof:

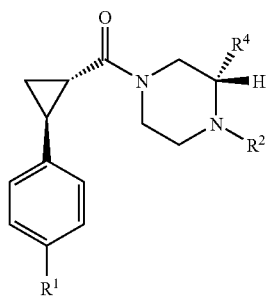

VIIa wherein:

$R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2NR^{11}R^{12}$, heterocycle, cyano, haloalkyl, —C(=O)$NR^{11}R^{12}$, alkoxy, or halogen;

$R^2$ is $C_1$-$C_6$alkyl or $C_3$-$C_6$cycloalkyl;

$R^4$ is $C_1$-$C_3$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In yet still another aspect, the disclosure provides a compound of formula VIIb, or pharmaceutically acceptable salts thereof, or mixtures thereof:

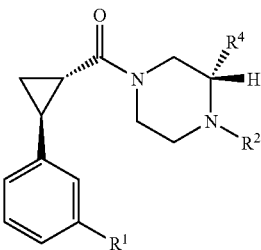

VIIb wherein:

$R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2NR^{11}R^{12}$, heterocycle, cyano, haloalkyl, —C(=O)$NR^{11}R^{12}$, alkoxy, or halogen;

$R^2$ is $C_1$-$C_6$alkyl or $C_3$-$C_6$cycloalkyl;

$R^4$ is $C_1$-$C_3$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In yet another aspect, the disclosure provides a compound of formula VIII, or pharmaceutically acceptable salts thereof, or mixtures thereof:

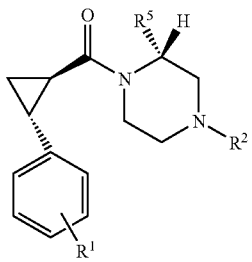

VIII wherein:
R[1] is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—NR[11]R[12], —S(=O)$_2$NR[11]R[12], heterocycle, cyano, haloalkyl, —C(=O)NR[11]R[12], alkoxy, or halogen;
R[2] is $C_1$-$C_6$alkyl or $C_3$-$C_6$cycloalkyl;
R[5] is $C_1$-$C_3$alkyl; and
R[11] and R[12] are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or R[11], R[12] and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In yet still an even further aspect, the disclosure provides a compound of formula VIIIa or pharmaceutically acceptable salts thereof, or mixtures thereof:

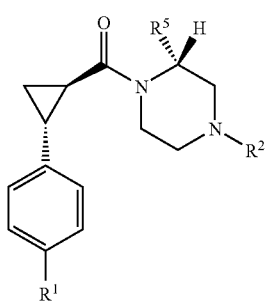

VIIIa wherein:
R[1] is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—NR[11]R[12], —S(=O)$_2$NR[11]R[12], heterocycle, cyano, haloalkyl, —C(=O)NR[11]R[12], alkoxy, or halogen;
R[2] is $C_1$-$C_6$alkyl or $C_3$-$C_6$cycloalkyl;
R[5] is $C_1$-$C_3$alkyl; and
R[11] and R[12] are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or R[11], R[12] and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In even still another aspect, the disclosure provides a compound of formula VIIIb or pharmaceutically acceptable salts thereof, or mixtures thereof:

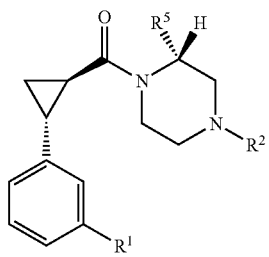

VIIIb wherein:
R[1] is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)$_2$NR[11]R[12], —S(=O)$_2$NR[11]R[12], heterocycle, cyano, haloalkyl, —C(=O)NR[11]R[12], alkoxy, or halogen;
R[2] is $C_1$-$C_6$alkyl or $C_3$-$C_6$cycloalkyl;
R[5] is $C_1$-$C_3$alkyl; and
R[11] and R[12] are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or R[11], R[12] and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In an even still further aspect, the disclosure provides a compound of formula IX, or pharmaceutically acceptable salts thereof, or mixtures thereof:

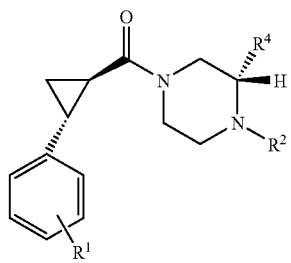

IX wherein:
R[1] is aryl, heteroaryl, —$C_1$-$C_6$alkyl-$C_1$-$C_3$alkoxy, —$C_1$-$C_6$alkyl-hydroxy, —$C_1$-$C_6$alkyl, C(=O)—NR[11]R[12], —S(=O)$_2$NR[11]R[12], heterocycle, cyano, haloalkyl, —C(=O)NR[11]R[12], alkoxy, or halogen;

R² is C₁-C₆alkyl or C₃-C₆cycloalkyl;

R⁴ is C₁-C₃alkyl; and

R¹¹ and R¹² are each independently selected from H, —C₁-C₆alkyl, —C₁-C₃alkyl-C₁-C₃alkoxy, 5-membered heterocycloalkyl containing at least one heteroatom selected from O and N, 6-membered heterocycloalkyl containing at least one heteroatom selected from O and N, —C₁-C₃alkyl-(5-membered heteroaryl containing at least one heteroatom selected from O and N), —C₁-C₃alkyl-(6-membered heteroaryl containing at least one heteroatom selected from O and N), haloalkyl, or R¹¹, R¹² and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C₁-C₃alkyl and —C₁-C₆alkyl-C₁-C₃alkoxy.

In still another aspect, the disclosure provides a compound of formula IXa, or pharmaceutically acceptable salts thereof, or mixtures thereof:

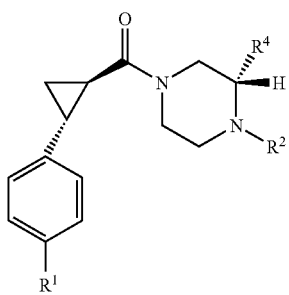

IX wherein:

R¹ is aryl, heteroaryl, —C₁-C₆alkyl-C₁-C₃alkoxy, —C₁-C₆alkyl-hydroxy, —C₁-C₆alkyl-C(=O)—NR¹¹R¹², —S(O)₂NR¹¹R¹², heterocycle, cyano, haloalkyl, —C(=O)NR¹¹R¹², alkoxy, or halogen;

R² is C₁-C₆alkyl or C₃-C₆cycloalkyl;

R⁴ is C₁-C₃alkyl; and

R¹¹ and R¹² are each independently selected from H, —C₁-C₆alkyl, —C₁-C₃alkyl-C₁-C₃alkoxy, 5-membered heterocycloalkyl containing at least one heteroatom selected from O and N, 6-membered heterocycloalkyl containing at least one heteroatom selected from O and N, —C₁-C₃alkyl-(5-membered heteroaryl containing at least one heteroatom selected from O and N), —C₁-C₃alkyl-(6-membered heteroaryl containing at least one heteroatom selected from O and N), haloalkyl, or R¹¹, R¹² and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C₁-C₃alkyl and —C₁-C₆alkyl-C₁-C₃alkoxy.

In a still further aspect, the disclosure provides a compound of formula IXb, or pharmaceutically acceptable salts thereof, or mixtures thereof:

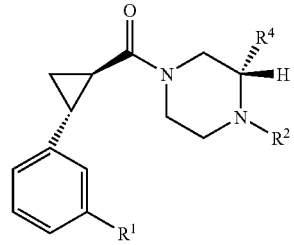

IXb wherein:

R¹ is aryl, heteroaryl, —C₁-C₆alkyl-C₁-C₃alkoxy, —C₁-C₆alkyl-hydroxy, —C₁-C₆alkyl-C(=O)—NR¹¹R¹², —S(=O)₂NR¹¹R¹², heterocycle, cyano, haloalkyl, —C(=O)NR¹¹R¹², alkoxy, or halogen;

R² is C₁-C₆alkyl or C₃-C₆cycloalkyl;

R⁴ is C₁-C₃alkyl; and

R¹¹ and R¹² are each independently selected from H, —C₁-C₆alkyl, —C₁-C₃alkyl-C₁-C₃alkoxy, 5-membered heterocycloalkyl containing at least one heteroatom selected from O and N, 6-membered heterocycloalkyl containing at least one heteroatom selected from O and N, —C₁-C₃alkyl-(5-membered heteroaryl containing at least one heteroatom selected from O and N), —C₁-C₃alkyl-(6-membered heteroaryl containing at least one heteroatom selected from O and N), haloalkyl, or R¹¹, R¹² and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C₁-C₃alkyl and —C₁-C₆alkyl-C₁-C₃alkoxy.

In yet another aspect, the disclosure provides a compound of formula X, or enantiomers or diastereomers thereof, or pharmaceutically acceptable salts of formula X or enantiomers or diastereomers thereof, or mixtures thereof:

X wherein:

R¹ is aryl, heteroaryl, —C₁-C₆alkyl-C₁-C₃alkoxy, —C₁-C₆alkyl-hydroxy, —C₁-C₆alkyl-C(=O)—NR¹¹R¹², —S(=O)₂NR¹¹R¹², heterocycle, cyano, haloalkyl, —C(=O)NR¹¹R¹², alkoxy, or halogen;

R² is C₁-C₆alkyl or C₃-C₆cycloalkyl;

R⁵ is C₁-C₃alkyl; and

R¹¹ and R¹² are each independently selected from H, —C₁-C₆alkyl, —C₁-C₃alkyl-C₁-C₃alkoxy, 5-membered heterocycloalkyl containing at least one heteroatom selected from O and N, 6-membered heterocycloalkyl containing at least one heteroatom selected from O and N, —C₁-C₃alkyl-(5-membered heteroaryl containing at least one heteroatom selected from O and N), —C₁-C₃alkyl-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and provided:
  i) formula X is not in the cis configuration at the cyclopropane.

In still yet another aspect, the disclosure provides a compound of formula Xa, or enantiomers or diastereomers thereof, or pharmaceutically acceptable salts of formula Xa or enantiomers or diastereomers thereof, or mixtures thereof:

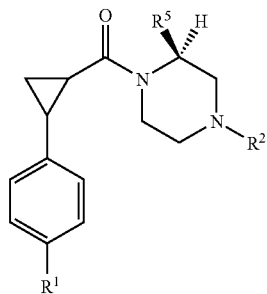

Xa wherein:
  $R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2$$NR^{11}R^{12}$, heterocycle, cyano, haloalkyl, —C(=O)$NR^{11}R^{12}$, alkoxy, or halogen;
  $R^2$ is $C_1$-$C_6$alkyl or $C_3$-$C_6$cycloalkyl;
  $R^5$ is $C_1$-$C_3$alkyl; and
  $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and
  provided:
    i) formula Xa is not in the cis configuration at the cyclopropane.

In even still yet another aspect, the disclosure provides a compound of formula Xb, or enantiomers or diastereomers thereof, or pharmaceutically acceptable salts of formula Xb or enantiomers or diastereomers thereof, or mixtures thereof:

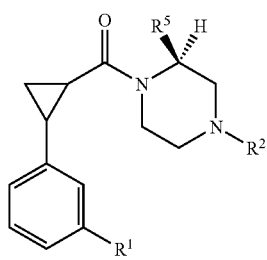

Xb wherein:
  $R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2$$NR^{11}R^{12}$, heterocycle, cyano, haloalkyl, —C(=O)$NR^{11}R^{12}$, alkoxy, or halogen;
  $R^2$ is $C_1$-$C_6$alkyl or $C_3$-$C_6$cycloalkyl;
  $R^5$ is $C_1$-$C_3$alkyl; and
  $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy; and
  provided:
    i) formula Xb is not in the cis configuration at the cyclopropane.

In a further aspect, the disclosure provides a compound of formula XI, or pharmaceutically acceptable salts thereof, or mixtures thereof:

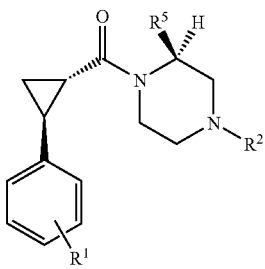

XI wherein:
  $R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2$$NR^{11}R^{13}$, heterocycle, cyano, haloalkyl, —C(=O)$NR^{11}R^{12}$, alkoxy, or halogen;
  $R^2$ is $C_1$-$C_6$alkyl or $C_3$-$C_6$cycloalkyl;
  $R^5$ is $C_1$-$C_3$alkyl; and
  $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In a still further aspect, the disclosure provides a compound of formula XIa, or pharmaceutically acceptable salts thereof, or mixtures thereof:

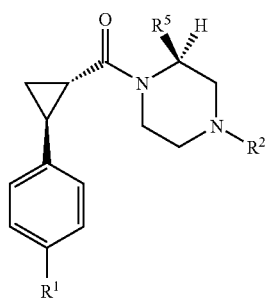

XIa wherein:
R$^1$ is aryl, heteroaryl, —C$_1$-C$_6$alkyl-C$_1$-C$_3$alkoxy, —C$_1$-C$_6$alkyl-hydroxy, —C$_1$-C$_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;
R$^2$ is C$_1$-C$_6$alkyl or C$_3$-C$_6$cycloalkyl;
R$^5$ is C$_1$-C$_3$alkyl; and
R$^{11}$ and R$^{12}$ are each independently selected from H, —C$_1$-C$_6$alkyl, —C$_1$-C$_3$alkyl-C$_1$-C$_3$alkoxy, 5-membered heterocycloalkyl containing at least one heteroatom selected from O and N, 6-membered heterocycloalkyl containing at least one heteroatom selected from O and N, —C$_1$-C$_3$alkyl-(5-membered heteroaryl containing at least one heteroatom selected from O and N), —C$_1$-C$_3$alkyl-(6-membered heteroaryl containing at least one heteroatom selected from O and N), haloalkyl, or R$^{11}$, R$^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C$_1$-C$_3$alkyl and —C$_1$-C$_6$alkyl-C$_1$-C$_3$alkoxy.

In yet a further aspect, the disclosure provides a compound of formula XIb, or pharmaceutically acceptable salts thereof, or mixtures thereof:

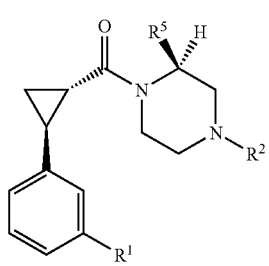

XIb wherein:
R$^1$ is aryl, heteroaryl, —C$_1$-C$_6$alkyl-C$_1$-C$_3$alkoxy, —C$_1$-C$_6$alkyl-hydroxy, —C$_1$-C$_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;
R$^2$ is C$_1$-C$_6$alkyl or C$_3$-C$_6$cycloalkyl;
R$^5$ is C$_1$-C$_3$alkyl; and
R$^{11}$ and R$^{12}$ are each independently selected from H, —C$_1$-C$_6$alkyl, —C$_1$-C$_3$alkyl-C$_1$-C$_3$alkoxy, 5-membered heterocycloalkyl containing at least one heteroatom selected from O and N, 6-membered heterocycloalkyl containing at least one heteroatom selected from O and N, —C$_1$-C$_3$alkyl-(5-membered heteroaryl containing at least one heteroatom selected from O and N), —C$_1$-C$_3$alkyl-(6-membered heteroaryl containing at least one heteroatom selected from O and N), haloalkyl, or R$^{11}$, R$^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C$_1$-C$_3$alkyl and —C$_1$-C$_6$alkyl-C$_1$-C$_3$alkoxy.

In an even further aspect, the disclosure provides a compound of formula XII, or enantiomers or diastereomers thereof, or pharmaceutically acceptable salts of formula XII or enantiomers or diastereomers thereof, or mixtures thereof:

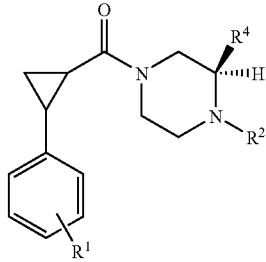

XII wherein:
R$^1$ is aryl, heteroaryl, —C$_1$-C$_6$alkyl-C$_1$-C$_3$alkoxy, —C$_1$-C$_6$alkyl-hydroxy, —C$_1$-C$_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;
R$^2$ is C$_1$-C$_6$alkyl or C$_3$-C$_6$cycloalkyl;
R$^4$ is C$_1$-C$_3$alkyl; and
R$^{11}$ and R$^{12}$ are each independently selected from H, —C$_1$-C$_6$alkyl, —C$_1$-C$_3$alkyl-C$_1$-C$_3$alkoxy, 5-membered heterocycloalkyl containing at least one heteroatom selected from O and N, 6-membered heterocycloalkyl containing at least one heteroatom selected from O and N, —C$_1$-C$_3$alkyl-(5-membered heteroaryl containing at least one heteroatom selected from O and N), —C$_1$-C$_3$alkyl-(6-membered heteroaryl containing at least one heteroatom selected from O and N), haloalkyl, or R$^{11}$, R$^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C$_1$-C$_3$alkyl and —C$_1$-C$_6$alkyl-C$_1$-C$_3$alkoxy; and
provided:
i) formula XII is not in the cis configuration at the cyclopropane.

In a still even further aspect, the disclosure provides a compound of formula XIIa, or enantiomers or diastereomers thereof, or pharmaceutically acceptable salts of formula XIIa or enantiomers or diastereomers thereof, or mixtures thereof:

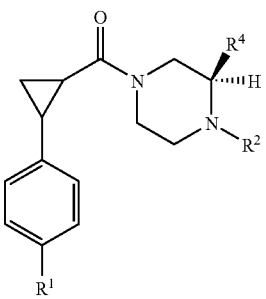

XIIa wherein:
R$^1$ is aryl, heteroaryl, —C$_1$-C$_6$alkyl-C$_1$-C$_3$alkoxy, —C$_1$-C$_6$alkyl-hydroxy, —C$_1$-C$_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;
R$^2$ is C$_1$-C$_6$alkyl or C$_3$-C$_6$cycloalkyl;
R$^4$ is C$_1$-C$_3$alkyl; and
R$^{11}$ and R$^{12}$ are each independently selected from H, —C$_1$-C$_6$alkyl, —C$_1$-C$_3$alkyl-C$_1$-C$_3$alkoxy, 5-membered heterocycloalkyl containing at least one heteroatom selected from O and N, 6-membered heterocycloalkyl containing at least one heteroatom selected from O and N, —C$_1$-C$_3$alkyl-(5-membered heteroaryl containing at least one heteroatom selected from O and N), —C$_1$-C$_3$alkyl-(6-membered heteroaryl containing at least one heteroatom selected from O and N), haloalkyl, or R$^{11}$, R$^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C$_1$-C$_3$alkyl and —C$_1$-C$_6$alkyl-C$_1$-C$_3$alkoxy; and
provided:
i) formula XIIa is not in the cis configuration at the cyclopropane.

In yet a still even further aspect, the disclosure provides a compound of formula XIIb, or enantiomers or diastereomers thereof, or pharmaceutically acceptable salts of formula XIIb or enantiomers or diastereomers thereof, or mixtures thereof:

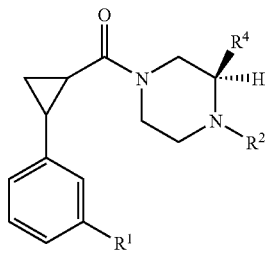

XIIb wherein:
R$^1$ is aryl, heteroaryl, —C$_1$-C$_6$alkyl-C$_1$-C$_3$alkoxy, —C$_1$-C$_6$alkyl-hydroxy, —C$_1$-C$_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;
R$^2$ is C$_1$-C$_6$alkyl or C$_3$-C$_6$cycloalkyl;
R$^4$ is C$_1$-C$_3$alkyl; and
R$^{11}$ and R$^{12}$ are each independently selected from H, —C$_1$-C$_6$alkyl, —C$_1$-C$_3$alkyl-C$_1$-C$_3$alkoxy, 5-membered heterocycloalkyl containing at least one heteroatom selected from O and N, 6-membered heterocycloalkyl containing at least one heteroatom selected from O and N, —C$_1$-C$_3$alkyl-(5-membered heteroaryl containing at least one heteroatom selected from O and N), —C$_1$-C$_3$alkyl-(6-membered heteroaryl containing at least one heteroatom selected from O and N), haloalkyl, or R$^{11}$, R$^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C$_1$-C$_3$alkyl and —C$_1$-C$_6$alkyl-C$_1$-C$_3$alkoxy; and
provided:
i) formula XIIb is not in the cis configuration at the cyclopropane.

In another aspect, the disclosure provides a compound of formula XIII, or pharmaceutically acceptable salts thereof, or mixtures thereof:

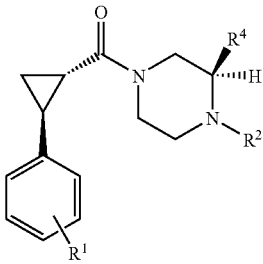

XIII wherein:
R$^1$ is aryl, heteroaryl, —C$_1$-C$_6$alkyl-C$_1$-C$_3$alkoxy, —C$_1$-C$_6$alkyl-hydroxy, —C$_1$-C$_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;
R$^2$ is C$_1$-C$_6$alkyl or C$_3$-C$_6$cycloalkyl;
R$^4$ is C$_1$-C$_3$alkyl; and
R$^{11}$ and R$^{12}$ are each independently selected from H, —C$_1$-C$_6$alkyl, —C$_1$-C$_3$alkyl-C$_1$-C$_3$alkoxy, 5-membered heterocycloalkyl containing at least one heteroatom selected from O and N, 6-membered heterocycloalkyl containing at least one heteroatom selected from O and N, —C$_1$-C$_3$alkyl-(5-membered heteroaryl containing at least one heteroatom selected from O and N), —C$_1$-C$_3$alkyl-(6-membered heteroaryl containing at least one heteroatom selected from O and N), haloalkyl, or R$^{11}$, R$^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C$_1$-C$_3$alkyl and —C$_1$-C$_6$alkyl-C$_1$-C$_3$alkoxy.

In still another aspect, the disclosure provides a compound of formula XIIIa, or pharmaceutically acceptable salts thereof, or mixtures thereof:

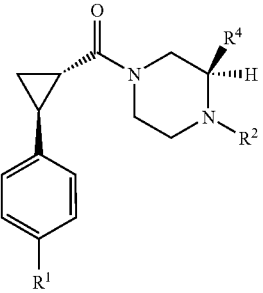

XIIIa wherein:
R$^1$ is aryl, heteroaryl, —C$_1$-C$_6$alkyl-C$_1$-C$_3$alkoxy, —C$_1$-C$_6$alkyl-hydroxy, —C$_1$-C$_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;
R$^2$ is C$_1$-C$_6$alkyl or C$_3$-C$_6$cycloalkyl;
R$^4$ is C$_1$-C$_3$alkyl; and
R$^{11}$ and R$^{12}$ are each independently selected from H, —C$_1$-C$_6$alkyl, —C$_1$-C$_3$alkyl-C$_1$-C$_3$alkoxy, 5-membered heterocycloalkyl containing at least one heteroatom selected from O and N, 6-membered heterocycloalkyl containing at least one heteroatom selected from O and N, —C$_1$-C$_3$alkyl-(5-membered heteroaryl containing at least one heteroatom selected from O and N), —C$_1$-C$_3$alkyl-(6-membered heteroaryl containing at least one heteroatom selected from O and N), haloalkyl, or R$^{11}$, R$^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C$_1$-C$_3$alkyl and —C$_1$-C$_6$alkyl-C$_1$-C$_3$alkoxy.

In yet still another aspect, the disclosure provides a compound of formula XIIIb, or pharmaceutically acceptable salts thereof, or mixtures thereof:

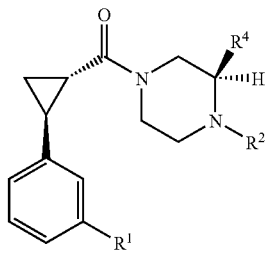

XIIIb wherein:
R$^1$ is aryl, heteroaryl, —C$_1$-C$_6$alkyl-C$_1$-C$_3$alkoxy, —C$_1$-C$_6$alkyl-hydroxy, —C$_1$-C$_6$alkyl-C(=O)$_2$NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;
R$^2$ is C$_1$-C$_6$alkyl or C$_3$-C$_6$cycloalkyl;
R$^4$ is C$_1$-C$_3$alkyl; and
R$^{11}$ and R$^{12}$ are each independently selected from H, —C$_1$-C$_6$alkyl, —C$_1$-C$_3$alkyl-C$_1$-C$_3$alkoxy, 5-membered heterocycloalkyl containing at least one heteroatom selected from O and N, 6-membered heterocycloalkyl containing at least one heteroatom selected from O and N, —C$_1$-C$_3$alkyl-(5-membered heteroaryl containing at least one heteroatom selected from O and N), —C$_1$-C$_3$alkyl-(6-membered heteroaryl containing at least one heteroatom selected from O and N), haloalkyl, or R$^{11}$, R$^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C$_1$-C$_3$alkyl and —C$_1$-C$_6$alkyl-C$_1$-C$_3$alkoxy.

In yet another aspect, the disclosure provides a compound of formula XIV, or pharmaceutically acceptable salts thereof, or mixtures thereof:

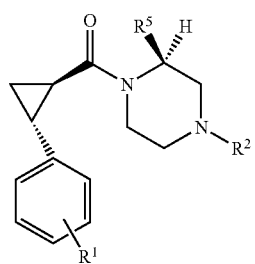

XIV wherein:
R$^1$ is aryl, heteroaryl, —C$_1$-C$_6$alkyl-C$_1$-C$_3$alkoxy, —C$_1$-C$_6$alkyl-hydroxy, —C$_1$-C$_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;
R$^2$ is C$_1$-C$_6$alkyl or C$_3$-C$_6$cycloalkyl;
R$^5$ is C$_1$-C$_3$alkyl; and
R$^{11}$ and R$^{12}$ are each independently selected from H, —C$_1$-C$_6$alkyl, —C$_1$-C$_3$alkyl-C$_1$-C$_3$alkoxy, 5-membered heterocycloalkyl containing at least one heteroatom selected from O and N, 6-membered heterocycloalkyl containing at least one heteroatom selected from O and N, —C$_1$-C$_3$alkyl-(5-membered heteroaryl containing at least one heteroatom selected from O and N), —C$_1$-C$_3$alkyl-(6-membered heteroaryl containing at least one heteroatom selected from O and N), haloalkyl, or R$^{11}$, R$^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C$_1$-C$_3$alkyl and —C$_1$-C$_6$alkyl-C$_1$-C$_3$alkoxy.

In yet still an even further aspect, the disclosure provides a compound of formula XIVa or pharmaceutically acceptable salts thereof, or mixtures thereof:

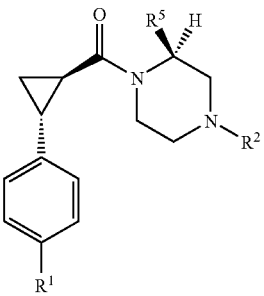

XIVa wherein:
R$^1$ is aryl, heteroaryl, —C$_1$-C$_6$alkyl-C$_1$-C$_3$alkoxy, —C$_1$-C$_6$alkyl-hydroxy, —C$_1$-C$_6$alkyl-C(=O)—NR$^{11}$R$^{12}$, —S(=O)$_2$NR$^{11}$R$^{12}$, heterocycle, cyano, haloalkyl, —C(=O)NR$^{11}$R$^{12}$, alkoxy, or halogen;
R$^2$ is C$_1$-C$_6$alkyl or C$_3$-C$_6$cycloalkyl;
R$^5$ is C$_1$-C$_3$alkyl; and
R$^{11}$ and R$^{12}$ are each independently selected from H, —C$_1$-C$_6$alkyl, —C$_1$-C$_3$alkyl-C$_1$-C$_3$alkoxy, 5-membered heterocycloalkyl containing at least one heteroatom selected from O and N, 6-membered heterocycloalkyl containing at least one heteroatom selected from O and N, —C$_1$-C$_3$alkyl-(5-membered heteroaryl containing at least one heteroatom selected from O and N), —C$_1$-C$_3$alkyl-(6-membered heteroaryl containing at least one heteroatom selected from O and N), haloalkyl, or R$^{11}$, R$^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —C$_1$-C$_3$alkyl and —C$_1$-C$_6$alkyl-C$_1$-C$_3$alkoxy.

In even still another aspect, the disclosure provides a compound of formula XIVb or pharmaceutically acceptable salts thereof, or mixtures thereof:

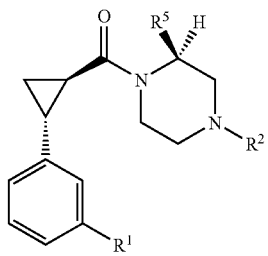

wherein:

R[1] is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—NR[11]R[12], —S(=O)$_2$NR[11]R[12], heterocycle, cyano, haloalkyl, —C(=O)NR[11]R[12], alkoxy, or halogen;

R[2] is $C_1$-$C_6$alkyl or $C_3$-$C_6$cycloalkyl;

R[5] is $C_1$-$C_3$alkyl; and

R[11] and R[12] are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or R[11], R[12] and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In an even still further aspect, the disclosure provides a compound of formula XV, or pharmaceutically acceptable salts thereof, or mixtures thereof:

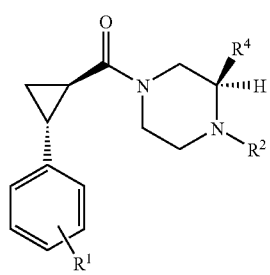

wherein:

R[1] is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—NR[11]R[12], —S(=O)$_2$NR[11]R[12], heterocycle, cyano, haloalkyl, —C(=O)NR[11]R[12], alkoxy, or halogen;

R[2] is $C_1$-$C_6$alkyl or $C_3$-$C_6$cycloalkyl;

R[4] is $C_1$-$C_3$alkyl; and

R[11] and R[12] are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or R[11], R[12] and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In still another aspect, the disclosure provides a compound of formula XVa, or pharmaceutically acceptable salts thereof, or mixtures thereof:

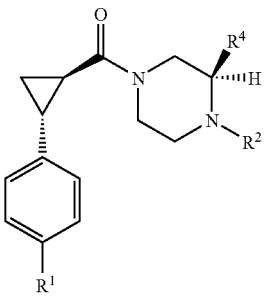

wherein:

R[1] is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—NR[11]R[12], —S(=O)$_2$NR[11]R[12], heterocycle, cyano, haloalkyl, —C(=O)NR[11]R[12], alkoxy, or halogen;

R[2] is $C_1$-$C_6$alkyl or $C_3$-$C_6$cycloalkyl;

R[4] is $C_1$-$C_3$alkyl; and

R[11] and R[12] are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or R[11], R[12] and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In a still further aspect, the disclosure provides a compound of formula XVb, or pharmaceutically acceptable salts thereof, or mixtures thereof:

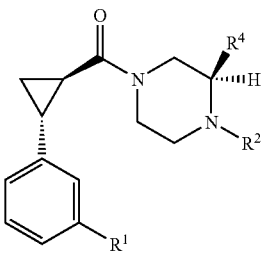

wherein:

R[1] is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)$_2$NR[11]R[12], —S(=O)$_2$NR[11]R[12], heterocycle, cyano, haloalkyl, —C(=O)NR[11]R[12], alkoxy, or halogen;

R[2] is $C_1$-$C_6$alkyl or $C_3$-$C_6$cycloalkyl;

$R^4$ is $C_1$-$C_3$alkyl; and $R^{11}$ and $R^{12}$ are each independently selected from H, —$C_1$-$C_6$alkyl, —$C_1$-$C_3$alkyl-$C_1$-$C_3$alkoxy, 5-membered heterocycloalkyl containing at least one heteroatom selected from O and N, 6-membered heterocycloalkyl containing at least one heteroatom selected from O and N, —$C_1$-$C_3$alkyl-(5-membered heteroaryl containing at least one heteroatom selected from O and N), —$C_1$-$C_3$alkyl-(6-membered heteroaryl containing at least one heteroatom selected from O and N), haloalkyl, or $R^{11}$, $R^{12}$ and the N to which they are attached come together to form a heterocycloalkyl selected from pyrrolidinyl, morpholinyl, piperidinyl, and piperazinyl, wherein said heterocycloalkyl is optionally substituted by at least one substituent selected from —$C_1$-$C_3$alkyl and —$C_1$-$C_6$alkyl-$C_1$-$C_3$alkoxy.

In another embodiment, $R^1$ is aryl, heteroaryl, —$C_1$-$C_6$alkyl-$C_1$-$C_3$alkoxy, —$C_1$-$C_6$alkyl-hydroxy, —$C_1$-$C_6$alkyl-C(=O)—$NR^{11}R^{12}$, —S(=O)$_2NR^{11}R^{12}$, cyano, haloalkyl, —C(=O)$NR^{11}R^{12}$, alkoxy, or halogen.

In still yet another embodiment, $R^1$ is —C(=O)$NR^{11}R^{12}$.

In yet another embodiment, $R^2$ is $C_1$-$C_6$alkyl.

In still another embodiment, $R^2$ is $C_3$-$C_6$cycloalkyl.

In a further embodiment, $R^2$ is $C_1$-$C_3$alkyl.

In yet another embodiment, $R^2$ is isopropyl or cyclobutyl.

In an even further embodiment, $R^3$ is H or methyl.

In still yet a further embodiment, $R^3$ is H.

In even a further embodiment, $R^3$ is methyl.

In yet a further embodiment, $R^4$ is H or methyl.

In yet an even further embodiment, $R^4$ is H.

In still yet an even further embodiment, $R^4$ is methyl.

In a still yet a further embodiment, $R^5$ is H, methyl, or ethyl.

In even a further embodiment, $R^5$ is H.

In still an even further embodiment, $R^5$ is methyl.

In still yet a further embodiment, $R^5$ is ethyl.

In still yet another embodiment, $R^6$ is H or methyl.

In still yet an even further embodiment, $R^6$ is H.

In still another embodiment, $R^6$ is methyl.

In yet another embodiment, $R^7$, $R^8$, $R^9$, and $R^{10}$ are each independently H.

Yet an even further embodiment is directed to at least one compound selected from: 4-(trans-2-((R)-4-isopropyl-2-methylpiperazine-1-carbonyl)cyclopropyl)benzamide, diastereomeric mixture; 4-(trans-2-((R)-4-isopropyl-2-methylpiperazine-1-carbonyl)cyclopropyl)benzamide, isomer 1; 4-(trans-2-((R)-4-isopropyl-2-methylpiperazine-1-carbonyl)cyclopropyl)benzamide, isomer 2; 4-(trans-2-((S)-4-isopropyl-2-methylpiperazine-1-carbonyl)cyclopropyl)benzamide, diastereomeric mixture; 4-(trans-2-((S)-4-isopropyl-2-methylpiperazine-1-carbonyl)cyclopropyl)benzamide, isomer 1; 4-(trans-2-((S)-4-isopropyl-2-methylpiperazine-1-carbonyl)cyclopropyl)benzamide, isomer 2; 4-(trans-2-((R)-4-cyclobutyl-2-methylpiperazine-1-carbonyl)cyclopropyl)benzamide, diastereomeric mixture; 4-(trans-2-((R)-4-cyclobutyl-2-methylpiperazine-1-carbonyl)cyclopropyl)benzamide, isomer 1; 4-(trans-2-((R)-4-cyclobutyl-2-methylpiperazine-1-carbonyl)cyclopropyl)benzamide, isomer 2; 4-(trans-2-((S)-4-cyclobutyl-2-methylpiperazine-1-carbonyl)cyclopropyl)benzamide, diastereomeric mixture; 4-(trans-2-((S)-4-cyclobutyl-2-methylpiperazine-1-carbonyl)cyclopropyl)benzamide, isomer 1; 4-(trans-2-((S)-4-cyclobutyl-2-methylpiperazine-1-carbonyl)cyclopropyl)benzamide, isomer 2; 4-(trans-2-((R)-4-cyclobutyl-2-ethylpiperazine-1-carbonyl)cyclopropyl)benzamide, diastereomeric mixture; 4-(trans-2-((R)-4-cyclobutyl-2-ethylpiperazine-1-carbonyl)cyclopropyl)benzamide, isomer 1; 4-(trans-2-((R)-4-cyclobutyl-2-ethylpiperazine-1-carbonyl)cyclopropyl)benzamide, isomer 2; 4-(trans-2-((S)-4-cyclobutyl-2-ethylpiperazine-1-carbonyl)cyclopropyl)benzamide, diastereomeric mixture; 4-(trans-2-((S)-4-cyclobutyl-3-methylpiperazine-1-carbonyl)cyclopropyl)benzamide, diastereomeric mixture; 4-(trans-2-((S)-4-cyclobutyl-3-methylpiperazine-1-carbonyl)cyclopropyl)benzamide, isomer 1; 4-(trans-2-((S)-4-cyclobutyl-3-methylpiperazine-1-carbonyl)cyclopropyl)benzamide, isomer 2; 4-(trans-2-((R)-4-cyclobutyl-3-methylpiperazine-1-carbonyl)cyclopropyl)benzamide, diastereomeric mixture; 4-(trans-2-((R)-4-cyclobutyl-3-methylpiperazine-1-carbonyl)cyclopropyl)benzamide, isomer 1; 4-(trans-2-((R)-4-cyclobutyl-3-methylpiperazine-1-carbonyl)cyclopropyl)benzamide, isomer 2; 4-(trans-2-(4-cyclobutyl-2,2-dimethylpiperazine-1-carbonyl)cyclopropyl)benzamide, enantiomeric mixture; 4-(trans-2-(4-cyclobutyl-3,3-dimethylpiperazine-1-carbonyl)cyclopropyl)benzamide, enantiomeric mixture; 4-(trans-2-(4-cyclobutyl-3,3-dimethylpiperazine-1-carbonyl)cyclopropyl)benzamide, enantiomer 1; 4-(trans-2-(4-cyclobutyl-3,3-dimethylpiperazine-1-carbonyl)cyclopropyl)benzamide, enantiomer 2; 3-(trans-2-((R)-4-cyclobutyl-2-methylpiperazine-1-carbonyl)cyclopropyl)benzamide, diastereomeric mixture; 3-(trans-2-((R)-4-cyclobutyl-2-methylpiperazine-1-carbonyl)cyclopropyl)benzamide, isomer 1; 3-(trans-2-((R)-4-cyclobutyl-2-methylpiperazine-1-carbonyl)cyclopropyl)benzamide, isomer 2; 3-(trans-2-((S)-4-cyclobutyl-2-methylpiperazine-1-carbonyl)cyclopropyl)benzamide, diastereomeric mixture; 3-(trans-2-((S)-4-cyclobutyl-2-methylpiperazine-1-carbonyl)cyclopropyl)benzamide, isomer 1; 3-(trans-2-((S)-4-cyclobutyl-2-methylpiperazine-1-carbonyl)cyclopropyl)benzamide, isomer 2; 3-(trans-2-((S)-4-cyclobutyl-3-methylpiperazine-1-carbonyl)cyclopropyl)benzamide, diastereomeric mixture; 4-{(1S,2S)-2-[((R)-4-Cyclobutyl-2-methylpiperazin-1-yl)carbonyl]-cyclopropyl}-benzamide; and 3-(trans-2-((R)-4-cyclobutyl-3-methylpiperazine-1-carbonyl)cyclopropyl)benzamide, diastereomeric mixture; and pharmaceutically acceptable salts thereof or mixtures thereof.

Another embodiment is directed to at least one compound selected from: 4-(trans-2-((R)-4-isopropyl-2-methylpiperazine-1-carbonyl)cyclopropyl)benzamide, isomer 1; 4-(trans-2-((S)-4-isopropyl-2-methylpiperazine-1-carbonyl)cyclopropyl)benzamide, isomer 1; 4-((trans)-2-((R)-4-cyclobutyl-2-methylpiperazine-1-carbonyl)cyclopropyl)benzamide, isomer 1; 4-((trans)-2-((S)-4-cyclobutyl-2-methylpiperazine-1-carbonyl)cyclopropyl)benzamide, isomer 1; 4-(trans-2-((R)-4-cyclobutyl-2-ethylpiperazine-1-carbonyl)cyclopropyl)benzamide, isomer 1; 4-((trans)-2-((S)-4-cyclobutyl-3-methylpiperazine-1-carbonyl)cyclopropyl)benzamide, isomer 1; 4-((trans)-2-((R)-4-cyclobutyl-3-methylpiperazine-1-carbonyl)cyclopropyl)benzamide, isomer 1; 4-(trans-2-(4-cyclobutyl-3,3-dimethylpiperazine-1-carbonyl)cyclopropyl)benzamide, enantiomer 1; 3-((trans)-2-((R)-4-cyclobutyl-2-methylpiperazine-1-carbonyl)cyclopropyl)benzamide, isomer 1; 4-{(1S,2S)-2-[((R)-4-Cyclobutyl-2-methylpiperazin-1-yl)carbonyl]-cyclopropyl}-benzamide; and 3-((trans)-2-((S)-4-cyclobutyl-2-methylpiperazine-1-carbonyl)cyclopropyl)benzamide, isomer 1; and pharmaceutically acceptable salts thereof or mixtures thereof.

If compounds of the present invention contain one or more chiral centers, the compounds of the invention may exist 1) in (and be isolated as) enantiomeric or diastereomeric forms, and/or 2) as a racemic mixture. The present invention includes any possible enantiomers, diastereomers, racemates or mixtures thereof, of the compounds of the formulae described herein. The optically active forms of the compound of the invention may be prepared, for example, by chiral chromatographic separation of a racemate, by synthesis from optically active starting materials or by asymmetric synthesis based on the procedures described hereafter.

It will also be understood that certain compounds of the invention may exist in solvated, for example hydrated, as well as unsolvated forms. It will further be understood that the present invention encompasses all such solvated forms of the compounds of the formulae described herein that possess the activity mentioned hereinbelow.

The compounds of the formulae described herein can also form salts. As a result, when a compound of a formulae described herein is referred to, such reference includes, unless otherwise indicated, salts thereof. In one embodiment, the compounds of the formulae described herein form pharmaceutically acceptable salts. In another embodiment, the compounds of the formulae described herein form salts that can, for example, be used to isolate and/or purify the compounds of the formulae described herein.

Generally, pharmaceutically acceptable salts of a compound in accordance with the formulae described herein can be obtained by using standard procedures well known in the art. These standard procedures include, but are not limited to, for example, the reacting of a sufficiently basic compound, such as, for example, an alkyl amine with a suitable acid, such as, for example, HCl or acetic acid, to afford a physiologically acceptable anion. It may also be possible to make a corresponding alkali metal (such as sodium, potassium, or lithium) or an alkaline earth metal (such as a calcium) salt by treating a compound in accordance with the formulae described herein, which have a suitably acidic proton, such as, for example, a carboxylic acid or a phenol with one equivalent of an alkali metal or alkaline earth metal hydroxide or alkoxide (such as, for example, an ethoxide or methoxide), or a suitably basic organic amine (such as, for example, a choline or meglumine) in an aqueous medium, followed by conventional purification techniques.

In one embodiment, a compound in accordance with the formulae described herein may be converted to a pharmaceutically acceptable salt or solvate thereof, particularly, an acid addition salt, such as, for example, hydrochloride, hydrobromide, phosphate, acetate, fumarate, maleate, tartrate, citrate, methanesulphonate, and p-toluenesulphonate.

In general, the compounds of the formulae described herein can be prepared in accordance with the following Schemes and the general knowledge of one skilled in the art and/or in accordance with the methods set forth in the Examples that follow. Solvents, temperatures, pressures, and other reaction conditions may readily be selected by one of ordinary skill in the art. Starting materials are commercially available or readily prepared by one skilled in the art. Combinatorial techniques can be employed in the preparation of compounds, for example, where the intermediates possess groups suitable for these techniques.

The term "amino-protecting group" refers to art-recognized moieties capable of attaching to an amino group so as to prevent the amino group from taking place in reactions occurring elsewhere on the molecule to which the amino group is attached. Acceptable amino-protecting groups, include but are not limited to, for example, amino-protecting groups described in "Protective Groups in Organic Synthesis", 2nd edition, John Wiley & Sons, 1981. The amino-protecting group may be, for example, a urethane type protective group (which is also referred to as a carbamate protective group), which includes but is not limited to, for example, arylalkyloxycarbonyl groups, such as, for example, benzyloxycarbonyl; and alkoxycarbonyl groups, such as, for example, methoxycarbonyl and tert-butoxycarbonyl. Typically, the amino-protecting group is tert-butoxycarbonyl.

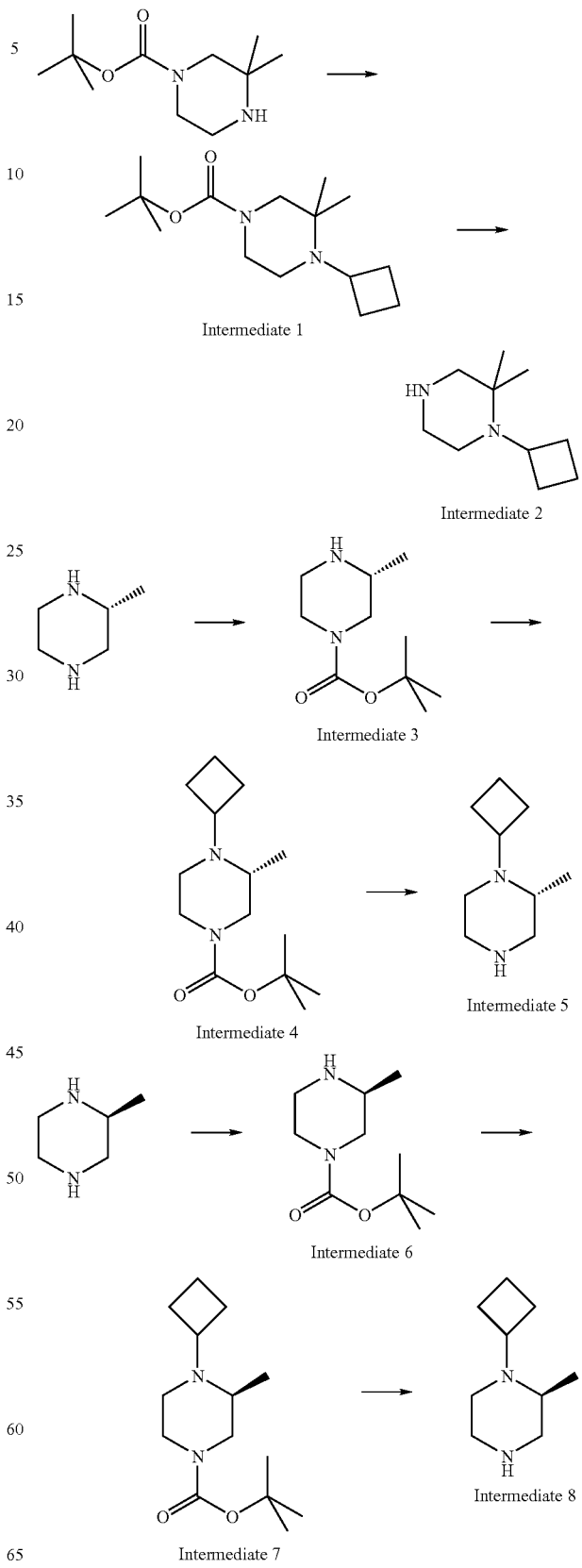

Scheme 1

Scheme 2
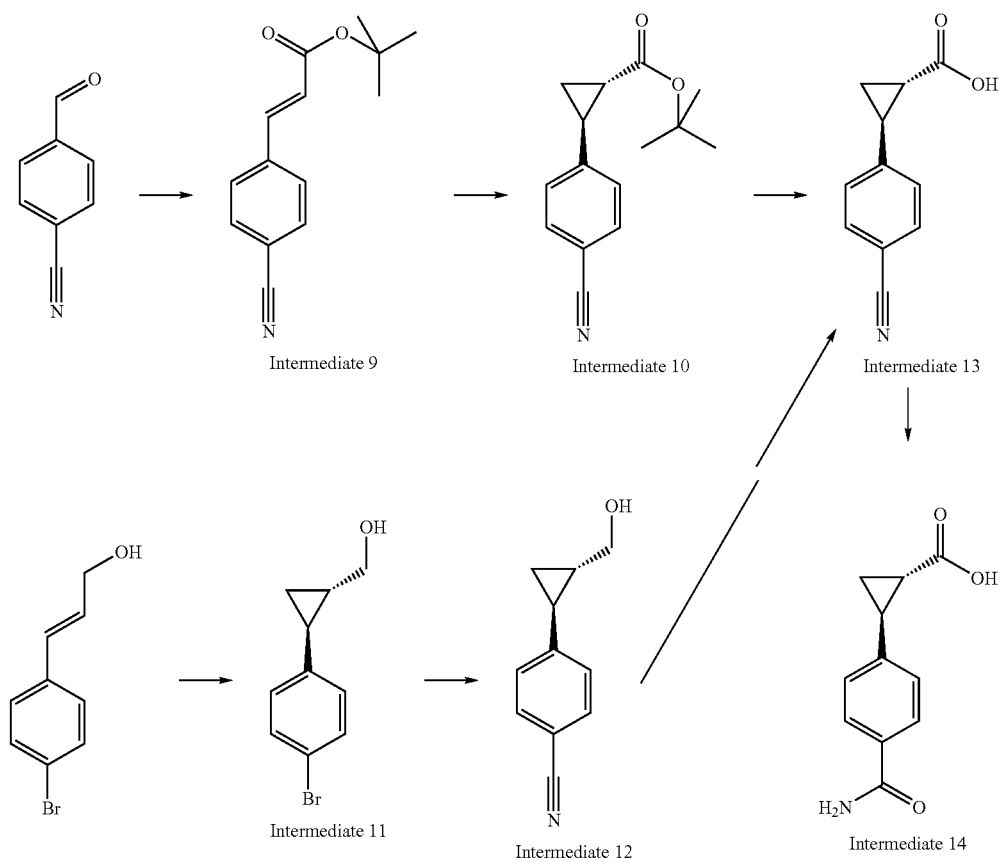
Scheme 3
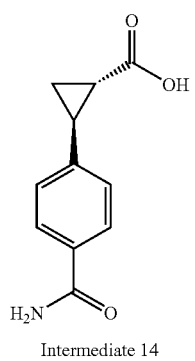
Intermediate 14
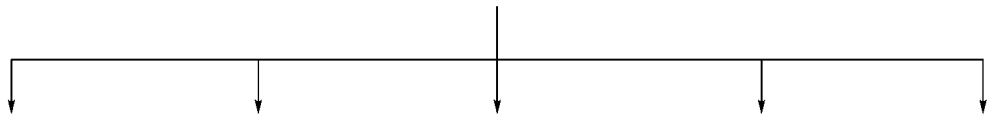

-continued
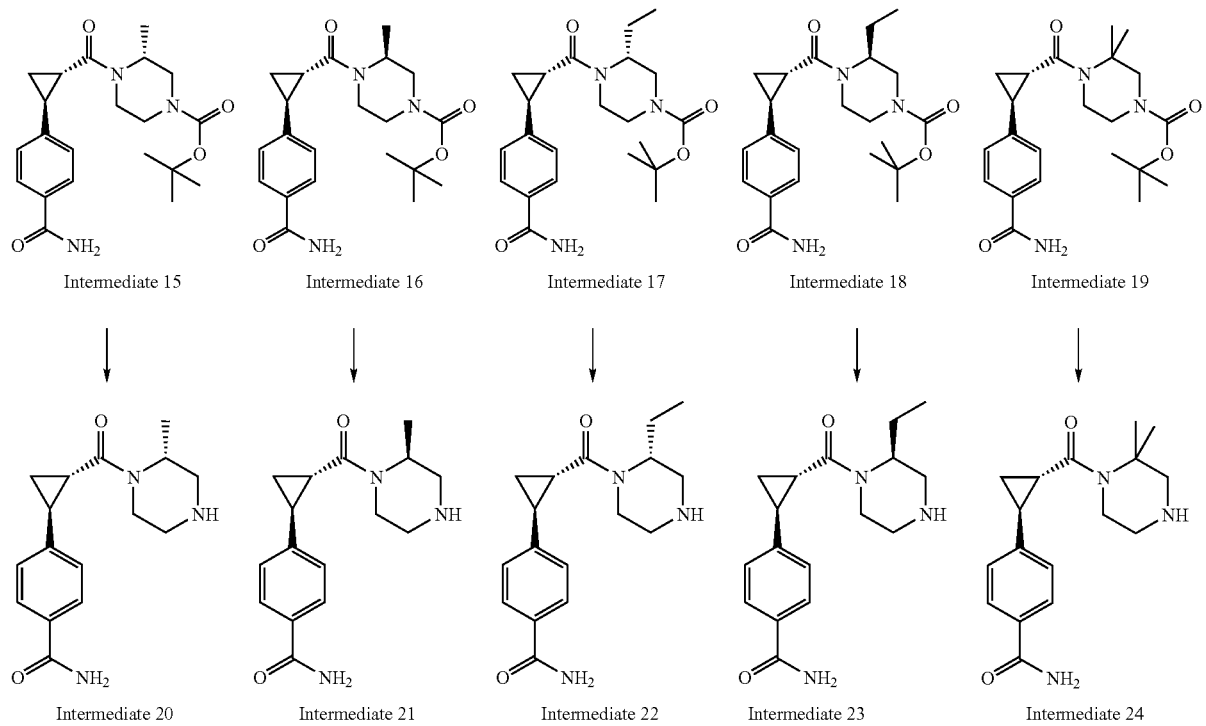
Scheme 4
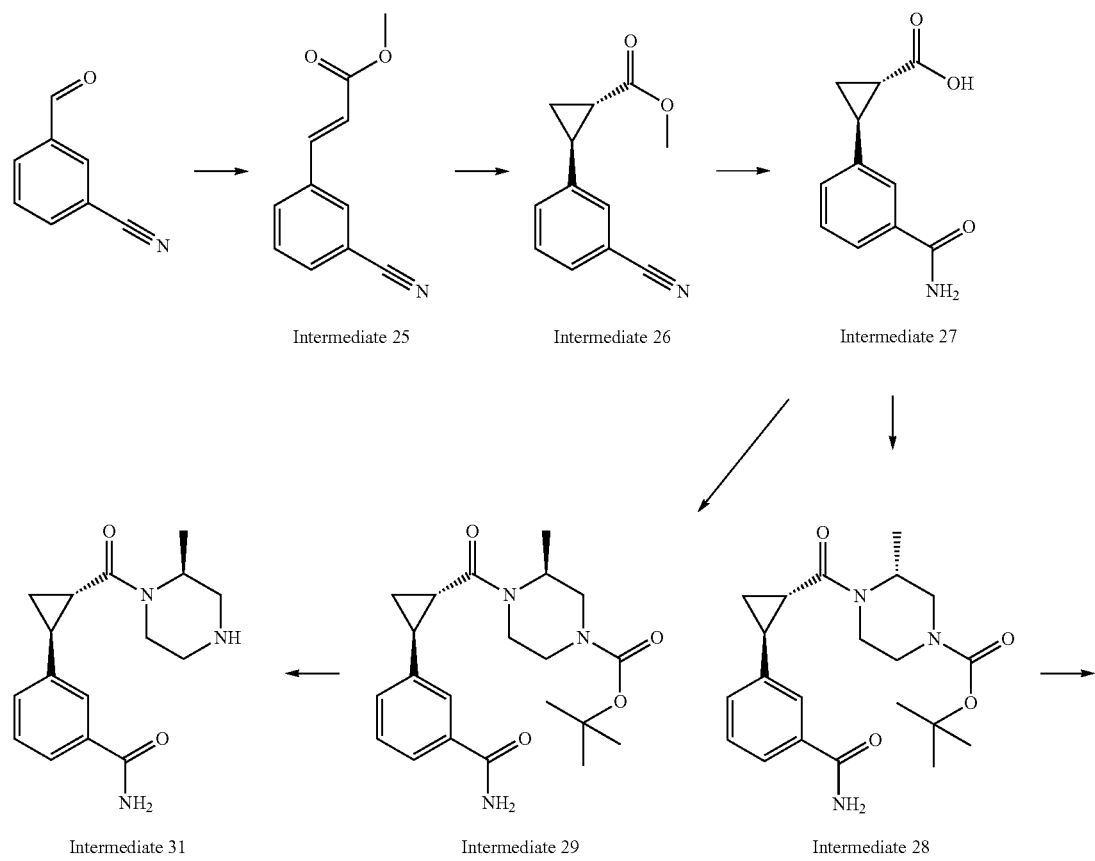

-continued
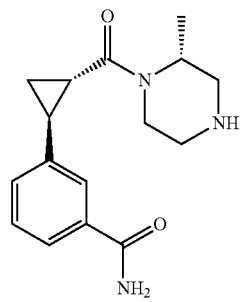
Intermediate 30
Scheme 5
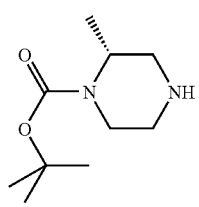 → 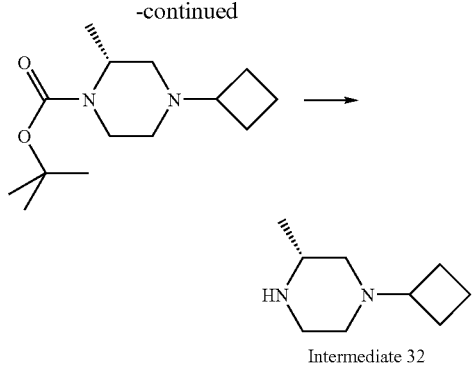
Intermediate 32
Scheme 6
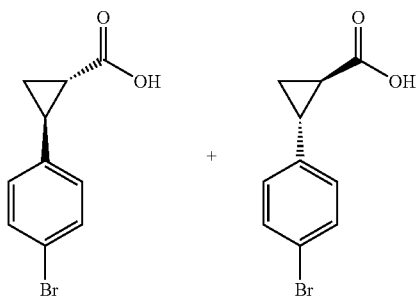
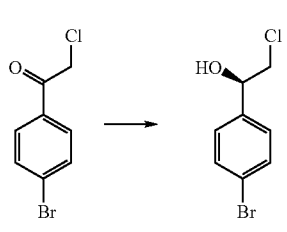 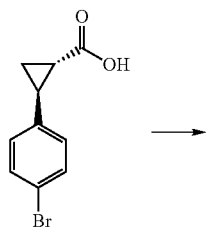 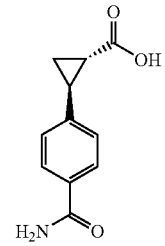
Intermediate 33   Intermediate 34   Intermediate 35   Intermediate 36   Intermediate 37

-continued

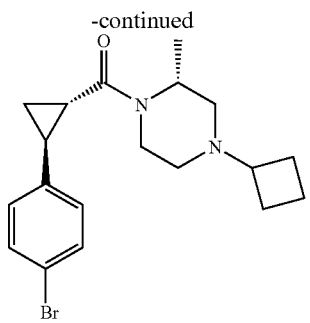

Intermediate 38

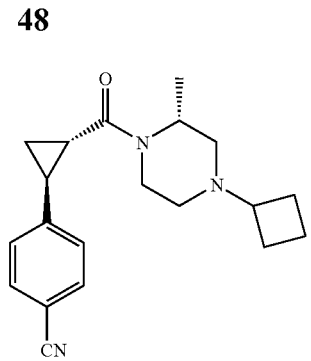

Intermediate 39

Another aspect of the disclosure is directed to a method for treating a disorder in which modulating the histamine H3 receptor is beneficial comprising administering to a warm-blooded animal in need of such treatment a therapeutically effective amount of at least one compound according to at least one formula described herein, or diastereomers or enantiomers thereof, or pharmaceutically acceptable salts of said formula, or diastereomers or enantiomers thereof, or mixtures thereof.

At least one compound in accordance with at least one formula described herein may be used to treat a wide range of conditions or disorders in which interacting with the histamine H3 receptor is beneficial. At least one compound in accordance with at least one formula describe herein may, for example, be useful to treat diseases of the central nervous system, the peripheral nervous system, the cardiovascular system, the pulmonary system, the gastrointestinal system, or the endocrinological system.

In one embodiment, at least one compound in accordance with at least one formula described herein modulates at least one histamine H3 receptor.

The terms "modulate", "modulates", "modulating", or "modulation", as used herein, refer to, for example, the activation (e.g., agonist activity) or inhibition (e.g., antagonist and inverse agonist activity) of at least one histamine H3 receptor.

In one embodiment, at least one compound in accordance with at least one formula described herein is an inverse agonist of at least one histamine H3 receptor.

In another embodiment, at least one compound in accordance with at least one formula described herein is an antagonist of at least one histamine H3 receptor.

In another embodiment, at least one compound in accordance with at least one formula described herein is an antagonist of at least one histamine H3 receptor.

In yet another embodiment, at least one compound in accordance with at least one formula described herein is an antagonist of at least one histamine H3 receptor.

Another embodiment provides a method for treating a disorder in which modulating the function of at least one histamine H3 receptor is beneficial comprising administering to a warm-blooded animal in need of such treatment a therapeutically effective amount of at least one compound according to at least one formula described herein.

In yet another embodiment, at least one compound in accordance with at least one formula described herein may be used as a medicament.

At least one compound in accordance with at least one formula described useful to treat at least one autoimmune disorder. Exemplary autoimmune disorders include, but are not limited to, for example, arthritis, skin grafts, organ transplants and similar surgical needs, collagen diseases, various allergies, tumors and viruses.

At least one compound in accordance with at least one formula described herein may be useful to treat at least one psychiatric disorder. Exemplary psychiatric disorders include, but are not limited to, for example, Psychotic Disorder(s) and Schizophrenia Disorder(s), such as, for example, Schizoaffective Disorder(s), Delusional Disorder(s), Brief Psychotic Disorder(s), Shared Psychotic Disorder(s), and Psychotic Disorder(s) Due to a General Medical Condition; Dementia and other Cognitive Disorder(s); Anxiety Disorder(s), such as, for example, Panic Disorder(s) Without Agoraphobia, Panic Disorder(s) With Agoraphobia, Agoraphobia Without History of Panic Disorder(s), Specific Phobia, Social Phobia, Obsessive-Compulsive Disorder(s), Stress related Disorder(s), Posttraumatic Stress Disorder(s), Acute Stress Disorder(s), Generalized Anxiety Disorder(s) and Generalized Anxiety Disorder(s) Due to a General Medical Condition; Mood Disorder(s), such as, for example, a) Depressive Disorder(s) (including but not limited to, for example, Major Depressive Disorder(s) and Dysthymic Disorder(s)), b) Bipolar Depression and/or Bipolar mania, such as, for example, Bipolar I (which includes, but is not limited to those with manic, depressive or mixed episodes), and Bipolar II, c) Cyclothymiac's Disorder(s), and d) Mood Disorder(s) Due to a General Medical Condition; Sleep Disorder(s), such as, for example, narcolepsy; Disorder(s) Usually First Diagnosed in Infancy, Childhood, or Adolescence including, but not limited to, for example, Mental Retardation, Downs Syndrome, Learning Disorder(s), Motor Skills Disorder(s), Communication Disorders(s), Pervasive Developmental Disorder(s), Attention-Deficit and Disruptive Behavior Disorder(s), Feeding and Eating Disorder(s) of Infancy or Early Childhood, Tic Disorder(s), and Elimination Disorder(s); Substance-Related Disorder(s) including, but not limited to, for example, Substance Dependence, Substance Abuse, Substance Intoxication, Substance Withdrawal, Alcohol-Related Disorder(s), Amphetamines (or Amphetamine-Like)-Related Disorder(s), Caffeine-Related Disorder(s), Cannabis-Related Disorder(s), Cocaine-Related Disorder(s), Hallucinogen-Related Disorder(s), Inhalant-Related Disorder(s), Nicotine-Related Disorder(s)s, Opioid-Related Disorder(s)s, Phencyclidine (or Phencyclidine-Like)-Related Disorder(s), and Sedative-, Hypnotic- or Anxiolytic-Related Disorder(s); Attention-Deficit and Disruptive Behavior Disorder(s); Eating Disorder(s), such as, for example, obesity; Personality Disorder(s) including, but not limited to, for example, Obsessive-Compulsive Personality Disorder(s); Impulse-Control Disorder(s); Tic Disorders including, but not limited to, for example Tourette's Disorder, Chronic motor or vocal tic disorder; and Transient Tic Disorder.

At least one of the above psychiatric disorders is defined, for example, in the American Psychiatric Association: Diagnostic and Statistical Manual of Mental Disorders, Fourth Edition, Text Revision, Washington, D.C., American Psychiatric Association, 2000.

At least one compound in accordance with at least one formula described herein may be useful i) to treat obesity or being overweight (e.g., promotion of weight loss and maintenance of weight loss), eating disorders (e.g., binge eating, anorexia, bulimia and compulsive), and/or cravings (for drugs, tobacco, alcohol, any appetizing macronutrients or non-essential food items); ii) to prevent weight gain (e.g., medication-induced or subsequent to cessation of smoking); and/or iii) to modulate appetite and/or satiety.

At least one compound in accordance with at least one formula described herein may be suitable for treating obesity by reducing appetite and body weight and/or maintaining weight reduction and preventing rebound.

At least one compound in accordance with at least one formula described herein may be used to prevent or reverse medication-induced weight gain, e.g. weight gain caused by antipsychotic (neuroleptic) treatment(s); and/or weight gain associated with smoking cessation.

At least one compound in accordance with at least one formula described herein may be useful to treat at least one Neurodegenerative Disorder. Exemplary Neurodegenerative Disorders include, but are not limited to, for example, Alzheimer's Disease (AD); Dementia, which includes, but is not limited to, for example, Alzheimer's Disease (AD), Down syndrome, vascular dementia, Parkinson's Disease (PD), postencephalitic parkinsonism, dementia with Lewy bodies, HIV dementia, Huntington's Disease, amyotrophic lateral sclerosis (ALS), motor neuron diseases (MND), Frontotemporal dementia Parkinson's Type (FTDP), progressive supranuclear palsy (PSP), Pick's Disease, Niemann-Pick's Disease, corticobasal degeneration, traumatic brain injury (TBI), dementia pugilistica, Creutzfeld-Jacob Disease and prion diseases; Cognitive Deficit in Schizophrenia (CDS); Mild Cognitive Impairment (MCI); Age-Associated Memory Impairment (AAMI); Age-Related Cognitive Decline (ARCD); Cognitive Impairment No Dementia (CIND); Multiple Sclerosis; Parkinson's Disease (PD); postencephalitic parkinsonism; Huntington's Disease; amyotrophic lateral sclerosis (ALS); motor neuron diseases (MND); Multiple System Atrophy (MSA); Corticobasal Degeneration; Progressive Supranuclear Paresis; Guillain-Barré Syndrome (GBS); and Chronic Inflammatory Demyelinating Polyneuropathy (CIDP).

At least one compound in accordance with the formulae described herein may be useful to treat at least one Neuroinflammatory Disorder including, but not limited to, for example, Multiple Sclerosis (MS), which includes, but is not limited to, for example, Relapse Remitting Multiple Sclerosis (RRMS), Secondary Progressive Multiple Sclerosis (SPMS), and Primary Progressive Multiple Sclerosis (PPMS); Parkinson's disease; Multiple System Atrophy (MSA); Corticobasal Degeneration; Progressive Supranuclear Paresis; Guillain-Barré Syndrome (GBS); and chronic inflammatory demyelinating polyneuropathy (CIDP).

At least one compound in accordance with at least one formula described herein may be useful to treat at least one Attention-Deficit and Disruptive Behavior Disorder. Exemplary Attention-Deficit and Disruptive Behavior Disorders include, but are not limited to, for example, attention deficit disorder (ADD), attention deficit hyperactivity disorder (ADHD), and affective disorders.

At least one compound in accordance with at least one formula described herein may be useful to treat pain; acute and chronic pain disorders including but not limited to, for example, Widespread pain, Localized pain, Nociceptive pain, Inflammatory pain, Central pain, Central and peripheral neuropathic pain, Central and peripheral neurogenic pain, Central and peripheral neuralgia, Low back pain, Postoperative pain, Visceral pain, and Pelvic pain; Allodynia; Anesthesia dolorosa; Causalgia; Dysesthesia; Fibromyalgia; Hyperalgesia; Hyperesthesia; Hyperpathia; Ischemic pain; Sciatic pain; Pain associated with cystitis including, but not limited to, interstitial cystitis; Pain associated with multiple sclerosis; Pain associated with arthritis; Pain associated with osteoarthritis; Pain associated with rheumatoid arthritis; and Pain associated with cancer.

At least one compound in accordance with at least one formula described herein may be used for the manufacture of a medicament for the treatment of at least one autoimmune disorder, psychiatric disorder, obesity disorder, eating disorder, craving disorder, neurodegenerative disorder, neuroinflammatory disorder, Attention-Deficit and Disruptive Behaviour Disorder, and/or pain disorder described hereinabove.

For example, in one embodiment at least one compound in accordance with at least one formula described herein may be used for the manufacture of a medicament for the treatment of at least one autoimmune disorder, psychiatric disorder, obesity disorder, eating disorder, craving disorder, neurodegenerative disorder, neuroinflammatory disorder, Attention-Deficit and Disruptive Behaviour Disorder, and/or pain disorder described hereinabove.

At least one compound in accordance with at least one formula described herein may be used for the manufacture of a medicament for the treatment of at least one disorder selected from cognitive deficit in schizophrenia, narcolepsy, attention deficit hyperactivity disorder, obesity, pain, and Alzheimer's disease.

For example, in one embodiment at least one compound in accordance with formula I may be used for the manufacture of a medicament for the treatment of at least one disorder selected from cognitive deficit in schizophrenia, narcolepsy, attention deficit hyperactivity disorder, obesity, pain, and Alzheimer's disease.

At least one compound in accordance with at least one formula described herein may be used for the treatment of at least one disorder selected from cognitive deficit in schizophrenia, narcolepsy, obesity, attention deficit hyperactivity disorder, pain, and Alzheimer's disease.

For example, one embodiment provides at least one compound in accordance with formula I for the treatment of at least one disorder selected from cognitive deficit in schizophrenia, narcolepsy, obesity, attention deficit hyperactivity disorder, pain, and Alzheimer's disease.

At least one compound in accordance with at least one formula described herein may be used for the treatment of at least one disorder selected from cognitive deficit in schizophrenia and Alzheimer's disease.

For example, one embodiment provides at least one compound in accordance with formula I for the treatment of at least one disorder selected from cognitive deficit in schizophrenia and Alzheimer's disease.

Another aspect provides a method for treating at least one autoimmune disorder, psychiatric disorder, obesity disorder, eating disorder, craving disorder, neurodegenerative disorder, neuroinflammatory disorder, attention-deficit and disruptive behaviour disorder, and/or pain disorder in a warm-blooded animal, comprising administering to said animal in need of such treatment a therapeutically effective amount of at least one compound in accordance with at least one formula described herein.

For example, one embodiment provides a method for treating at least one autoimmune disorder, psychiatric disorder, obesity disorder, eating disorder, craving disorder, neurodegenerative disorder, neuroinflammatory disorder, attention-deficit and disruptive behaviour disorder, and/or pain disorder in a warm-blooded animal, comprising administering to said animal in need of such treatment a therapeutically effective amount of at least one compound according to formula I.

Yet another aspect provides a method for treating at least one disorder selected from cognitive deficit in schizophrenia, narcolepsy, obesity, attention deficit hyperactivity disorder, pain, and Alzheimer's disease in a warm-blooded animal, comprising administering to said animal in need of such treatment a therapeutically effective amount of at least one compound in accordance with at least one formula described herein.

For example, one embodiment provides a method for treating at least one disorder selected from cognitive deficit in schizophrenia, narcolepsy, obesity, attention deficit hyperactivity disorder, pain, and Alzheimer's disease in a warm-blooded animal, comprising administering to said animal in need of such treatment a therapeutically effective amount of at least one compound according to formula I.

Yet another aspect provides a method for treating cognitive deficit in schizophrenia in a warm-blooded animal, comprising administering to said animal in need of such treatment a therapeutically effective amount of at least one compound in accordance with at least one formula described herein.

For example, one embodiment provides a method for treating cognitive deficit in schizophrenia in a warm-blooded animal, comprising administering to said animal in need of such treatment a therapeutically effective amount of at least one compound according to formula I.

Yet another aspect provides a method for treating obesity in a warm-blooded animal, comprising administering to said animal in need of such treatment a therapeutically effective amount of at least one compound in accordance with at least one formula described herein.

For example, one embodiment provides a method for treating obesity in a warm-blooded animal, comprising administering to said animal in need of such treatment a therapeutically effective amount of at least one compound according to formula I.

Yet another aspect provides a method for treating narcolepsy in a warm-blooded animal, comprising administering to said animal in need of such treatment a therapeutically effective amount of at least one compound in accordance with at least one formula described herein.

For example, one embodiment provides a method for treating narcolepsy in a warm-blooded animal, comprising administering to said animal in need of such treatment a therapeutically effective amount of at least one compound according to formula I.

Another aspect provides a method for treating Alzheimer's disease in a warm-blooded animal, comprising administering to said animal in need of such treatment a therapeutically effective amount of at least one compound in accordance with at least one formula described herein.

For example, one embodiment provides a method for treating Alzheimer's disease in a warm-blooded animal, comprising administering to said animal in need of such treatment a therapeutically effective amount of at least one compound according to formula I.

Another aspect provides a method for treating attention deficit hyperactivity disorder in a warm-blooded animal, comprising administering to said animal in need of such treatment a therapeutically effective amount of at least one compound in accordance with at least one formula described herein.

For example, one embodiment provides a method for treating attention deficit hyperactivity disorder in a warm-blooded animal, comprising administering to said animal in need of such treatment a therapeutically effective amount of at least one compound according to formula I.

Another aspect provides a method for treating a pain disorder in a warm-blooded animal, comprising administering to said animal in need of such treatment a therapeutically effective amount of at least one compound in accordance with at least one formula described herein.

For example, one embodiment provides a method for treating a pain disorder in a warm-blooded animal, comprising administering to said animal in need of such treatment a therapeutically effective amount of at least one compound according to formula I.

In one embodiment, the warm-blooded animal is a mammalian species including, but not limited to, for example, humans and domestic animals, such as, for example, dogs, cats, and horses.

In a further embodiment, the warm-blooded animal is a human.

Another aspect provides the use of at least one compound in accordance with at least one formula described herein in therapy.

For example, one embodiment provides the use of at least one compound in accordance with formula I in therapy.

Yet an even further embodiment provides the use of a compound in accordance with at least one formula described herein in the manufacture of a medicament for use in therapy.

As used herein, the term "therapy" also includes "prophylaxis" unless specifically indicated to the contrary.

In yet another embodiment a compound in accordance with at least one formula described herein, or a pharmaceutical composition or formulation comprising at least one compound in accordance with at least one formula described herein may be administered concurrently, simultaneously, sequentially or separately with at least one other pharmaceutically active compound selected from the following:

(i) antidepressants, such as, for example, agomelatine, amitriptyline, amoxapine, bupropion, citalopram, clomipramine, desipramine, doxepin, duloxetine, escitalopram, fluvoxamine, fluoxetine, gepirone, imipramine, ipsapirone, isocarboxazid, maprotiline, mirtazepine, nortriptyline, nefazodone, paroxetine, phenelzine, protriptyline, ramelteon, reboxetine, robalzotan, selegiline, sertraline, sibutramine, thionisoxetine, tranylcypromaine, trazodone, trimipramine, venlafaxine, and equivalents and pharmaceutically active isomer(s) and metabolite(s) thereof;

(ii) antipsychotics, such as, for example, amisulpride, aripiprazole, asenapine, benzisoxidil, bifeprunox, carbamazepine, clozapine, chlorpromazine, debenzapines, dibenzapine, divalproex, droperidol, fluphenazine, haloperidol, iloperidone, loxapine, mesoridazine, molindone, olanzapine, paliperidone, perphenazine, phenothiazine, phenylbutylpiperidine, pimozide, prochlorperazine, quetiapine, risperidone, sertindole, sulpiride, suproclone, thioridazine, thiothixene, trifluoperazine, trimetozine, valproate, valproic acid, zotepine, ziprasidone, and equivalents and pharmaceutically active isomer(s) and metabolite(s) thereof;

(iii) anxiolytics, such as, for example, alnespirone, azapirones, benzodiazepines, and barbiturates, such as, for example, adinazolam, alprazolam, balezepam, bentazepam, bromazepam, brotizolam, buspirone, clonazepam, clorazepate, chlordiazepoxide, cyprazepam, diazepam, estazolam, fenobam, flunitrazepam, flurazepam, fosazepam, lorazepam, lormetazepam, meprobamate, midazolam, nitrazepam, oxazepam, prazepam, quazepam, reclazepam, suriclone, tracazolate, trepipam, temazepam, triazolam, uldazepam, zolazepam, and equivalents and pharmaceutically active isomer(s) and metabolite(s) thereof;

(iv) anticonvulsants, such as, for example, carbamazepine, oxcarbazepine, valproate, lamotrogine, gabapentin, topiramate, phenytoin, ethosuximide, and equivalents and pharmaceutically active isomer(s) and metabolite(s) thereof;

(v) Alzheimer's therapies, such as, for example, donepezil, galantamine, memantine, rivastigmine, tacrine, and equivalents and pharmaceutically active isomer(s) and metabolite(s) thereof;

(vi) Parkinson's therapies and agents for the treatment of extrapyramidal symtpoms, such as, for example, levodopa, carbidopa, amantadine, pramipexole, ropinirole, pergolide, cabergoline, apomorphine, bromocriptine, MAOB inhibitors (i.e. selegine and rasagiline), COMT inhibitors (i.e. entacapone and tolcapone), alpha-2 inhibitors, anticholinergics (i.e., benztropine, biperiden, orphenadrine, procyclidine, and trihexyphenidyl), dopamine reuptake inhibitors, NMDA antagonists, Nicotine agonists, Dopamine agonists, and inhibitors of neuronal nitric oxide synthase, and equivalents and pharmaceutically active isomer(s) and metabolite(s) thereof;

(vii) migraine therapies, such as, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof;

(viii) stroke therapies, such as, for example, abciximab, activase, NXY-059, citicoline, crobenetine, desmoteplase, repinotan, traxoprodil, and equivalents and pharmaceutically active isomer(s) and metabolite(s) thereof;

(ix) urinary incontinence therapies, such as, for example, darafenacin, dicyclomine, falvoxate, imipramine, desipramine, oxybutynin, propiverine, propanthedine, robalzotan, solifenacin, alfazosin, doxazosin, terazosin, tolterodine, and equivalents and pharmaceutically active isomer(s) and metabolite(s) thereof;

(x) neuropathic pain therapies, such as, for example, gabapentin, lidoderm, pregablin, and equivalents and pharmaceutically active isomer(s) and metabolite(s) thereof;

(xi) nociceptive pain therapies, such as, for example, celecoxib, codeine, diclofenac, etoricoxib, fentanyl, hydrocodone, hydromorphone, levo-alpha-acetylmethadol, loxoprofen, lumiracoxib, meperidine, methadone, morphine, naproxen, oxycodone, paracetamol, propoxyphene, rofecoxib, sufentanyl, valdecoxib, and equivalents and pharmaceutically active isomer(s) and metabolite(s) thereof;

(xii) insomnia therapies and sedative hypnotics, such as, for example, agomelatine, allobarbital, alonimid, amobarbital, benzoctamine, butabarbital, capuride, chloral hydrate, clonazepam, chlorazepate, cloperidone, clorethate, dexclamol, estazolam, eszopiclone, ethchlorvynol, etomidate, flurazepam, glutethimide, halazepam, hydroxyzine, mecloqualone, melatonin, mephobarbital, methaqualone, midaflur, midazolam, nisobamate, pagoclone, pentobarbital, perlapine, phenobarbital, propofol, quazepam, ramelteon, roletamide, suproclone, temazepam, triazolam, triclofos, secobarbital, zaleplon, zolpidem, zopiclone and equivalents and pharmaceutically active isomer(s) and metabolite(s) thereof;

(xiii) mood stabilizers, such as, for example, carbamazepine, divalproex, gabapentin, lamotrigine, lithium, olanzapine, oxycarbazepine, quetiapine, valproate, valproic acid, verapamil, and equivalents and pharmaceutically active isomer(s) and metabolite(s) thereof;

(xiv) obesity therapies, such as, for example, anti-obesity drugs that affect energy expenditure, glycolysis, gluconeogenesis, glucogenolysis, lipolysis, lipogenesis, fat absorption, fat storage, fat excretion, hunger and/or satiety and/or craving mechanisms, appetite/motivation, food intake, and G-I motility; very low calorie diets (VLCD); and low-calorie diets (LCD);

(xv) therapeutic agents useful in treating obesity associated disorders, such as, for example, biguanide drugs, insulin (synthetic insulin analogues) and oral antihyperglycemics (these are divided into prandial glucose regulators and alpha-glucosidase inhibitors), PPAR modulating agents, such as, for example, PPAR alpha and/or gamma agonists; sulfonylureas; cholesterol-lowering agents, such as, for example, inhibitors of HMG-CoA reductase (3-hydroxy-3-methylglutaryl coenzyme A reductase); an inhibitor of the ileal bile acid transport system (IBAT inhibitor); a bile acid binding resin; bile acid sequestering agent, such as, for example, colestipol, cholestyramine, or cholestagel; a CETP (cholesteryl ester transfer protein) inhibitor; a cholesterol absorption antagonist; a MTP (microsomal transfer protein) inhibitor; a nicotinic acid derivative, including slow release and combination products; a phytosterol compound; probucol; an anti-coagulant; an omega-3 fatty acid; an anti-obesity therapy, such as, for example, sibutramine, phentermine, orlistat, bupropion, ephedrine, and thyroxine; an antihypertensive, such as, for example, an angiotensin converting enzyme (ACE) inhibitor, an angiotensin II receptor antagonist, an adrenergic blocker, an alpha adrenergic blocker, a beta adrenergic blocker, a mixed alpha/beta adrenergic blocker, an adrenergic stimulant, calcium channel blocker, an AT-1 blocker, a saluretic, a diuretic, and a vasodilator; a melanin concentrating hormone (MCH) modulator; an NPY receptor modulator; an orexin receptor modulator; a phosphoinositide-dependent protein kinase (PDK) modulator; modulators of nuclear receptors, suc as, for example, LXR, FXR, RXR, GR, ERRα, β, PPARα, β, γ and RORalpha; a monoamine transmission-modulating agent, such as, for example, a selective serotonin reuptake inhibitor (SSRI), a noradrenaline reuptake inhibitor (NARI), a noradrenaline-serotonin reuptake inhibitor (SNRI), a monoamine oxidase inhibitor (MAOI), a tricyclic antidepressive agent (TCA), a noradrenergic and specific serotonergic antidepressant (NaSSA); a serotonin receptor modulator; a leptin/leptin receptor modulator; a ghrelin/ghrelin receptor modulator; a DPP-IV inhibitor; and equivalents and pharmaceutically active isomer(s), metabolite(s), and pharmaceutically acceptable salts, solvates, and prodrugs thereof.

(xvi) agents for treating ADHD, such as, for example, amphetamine, methamphetamine, dextroamphetamine, atomoxetine, methylphenidate, dexmethylphenidate, modafinil, and equivalents and pharmaceutically active isomer(s) and metabolite(s) thereof; and (xvii) agents used to treat substance abuse disorders, dependence, and withdrawal, such as, for example, nicotine replacement therapies (i.e., gum, patches, and nasal spray); nicotinergic receptor agonists, partial agonists, and antagonists, (e.g. varenicline); acomprosate, bupropion, clonidine, disulfiram, methadone, naloxone, naltrexone, and equivalents and pharmaceutically active isomer(s) and metabolite(s) thereof.

When employed in combination with at least one compound in accordance with at least one formula described herein, the above other pharmaceutically active compound may be used, for example, in the amounts indicated in the Physicians' Desk Reference (PDR) or as otherwise determined by one of ordinary skill in the art.

Compound(s) in accordance with the formula described herein may be administered by any means suitable for the condition to be treated, which can depend on the quantity of the compound in accordance the formula described herein to be delivered.

Compound(s) in accordance with the formula described herein may be administered in the form of a conventional pharmaceutical composition by any route including, but not limited to, for example, orally, intramuscularly, subcutaneously, topically, intranasally, epidurally, intraperitoneally, intrathoracically, intravenously, intrathecally, intracerebroventricularly, and injecting into the joints.

In one embodiment, the route of administration is orally, intravenously or intramuscularly.

An "effective amount" of a compound in accordance with the formula described herein may be determined by one of ordinary skill in the art, and includes exemplary dosage amounts for a mammal of from about 0.05 to about 300 mg/kg/day, preferably less than about 200 mg/kg/day, in a single dose or in or in the form of individual divided doses. Exemplary dosage amounts for an adult human are from about 1 to 100 (for example, 15) mg/kg of body weight of active compound per day, which can be administered in a single dose or in the form of individual divided doses, such as from 1 to 4 times per day.

The specific dose level and frequency of dosage for any particular subject, however, may vary and generally depends on a variety of factors, including, but not limited to, for example, the bioavailability of the compound(s) in accordance with the formula described herein in the administered form; metabolic stability and length of action of the the compound(s) in accordance with the formula described herein; species, age, body weight, general health, sex, and diet of the subject; mode and time of administration; rate of excretion; drug combination; and severity of the particular condition.

One aspect provides a pharmaceutical composition comprising at least one compound in accordance with at least formula described herein and at least one pharmaceutically-acceptable carrier and/or diluent.

For example, one embodiment provides a pharmaceutical composition comprising at least one compound in accordance with formula I and at least one pharmaceutically-acceptable carrier and/or diluent.

Another embodiment provides a method for treating at least one disorder selected from cognitive deficit in schizophrenia, narcolepsy, obesity, attention deficit hyperactivity disorder, and Alzheimer's disease in a warm-blooded animal, comprising administering to said animal in need of such treatment a pharmaceutical composition comprising a therapeutically effective amount of a compound according to at least one formula described herein, and at least one pharmaceutically-acceptable carrier and/or diluent.

Acceptable solid pharmaceutical compositions include, but are not limited to, for example, powders, tablets, dispersible granules, capsules, cachets, and suppositories.

In a solid pharmaceutical composition, pharmaceutically acceptable carriers include, but are not limited to, for example, at least one solid, at least one liquid, and mixtures thereof. The solid carrier can also be a diluent, flavoring agent, solubilizer, lubricant, suspending agent, binder, encapsulating material, and/or table disintegrating agent. Suitable carriers, include, but are not limited to, for example, magnesium carbonate; magnesium stearate; talc; lactose; sugar; pectin; dextrin; starch; tragacanth; methyl cellulose; sodium carboxymethyl cellulose; a low-melting wax; cocoa butter; and mixtures thereof.

A powder can be prepared by, for example, mixing a finely divided solid with at least one finely divided compound of at least one formula described herein.

A tablet can be prepared by, for example, mixing at least one compound of at least one formula described herein in suitable proportions with a pharmaceutically acceptable carrier having the necessary binding properties and compacted into the desired shape and size.

A suppository can be prepared by, for example, mixing at least one compound of at least one formula described herein with at least one suitable non-irritating excipient that is liquid at rectal temperature but solid at a temperature below rectal temperature, wherein the non-irritating excipient is first melted and at least one compound in accordance with at least one formula described herein is dispersed therein. The molten homogeneous mixture in then poured into convenient sized molds and allowed to cool and solidify. Exemplary non-irritating excipients include, but are not limited to, for example, cocoa butter; glycerinated gelatin; hydrogenated vegetable oils; mixtures of polyethylene glycols of various molecular weights; and fatty acid esters of polyethylene glycol.

Acceptable liquid pharmaceutical compositions include, but are not limited to, for example, solutions, suspensions, and emulsions. For example, sterile water or water propylene glycol solutions of at least one compound of at least one formula described herein are liquid pharmaceutical compositions suitable for parenteral administration. Liquid compositions can also be formulated in solution in aqueous polyethylene glycol solution.

Aqueous solutions for oral administration can be prepared by dissolving at least one compound in accordance with at least one formula described herein in water and adding suitable colorants, flavoring agents, stabilizers, and/or thickening agents as desired.

Aqueous suspensions for oral administration can be prepared by dispersing at least one finely divided compound of at least one formula described herein in water together with a viscous materia, such as, for example, a natural synthetic gum, resin, methyl cellulose, and sodium carboxymethyl cellulose.

In one embodiment, the pharmaceutical composition contains from about 0.05% to about 99% w (percent by weight) of at least one compound in accordance with at least one formula described herein. All percentages by weight being based on total composition.

In another embodiment, the pharmaceutical composition contains from about 0.10% to about 50% w (percent by weight) of at least one compound in accordance with at least one formula described herein. All percentages by weight being based on total composition.

Another embodiment, provides a pharmaceutical composition comprising a compound of at least one formula described herein, and a pharmaceutically acceptable carrier/diluent for therapy.

Further, there is provided a pharmaceutical composition comprising a compound of at least one formula described herein, in association with a pharmaceutically acceptable carrier use in any of the conditions discussed above.

In a further aspect, the present invention provides a method of preparing a compound of at least one formula described herein.

Biological Evaluation

At least one compound of at least one formula described herein including the compounds described in the Examples hereof, when tested in at least one in vitro assay as substantially described below is active towards H3 receptors. Particularly, at least one compound described herein is an effective H3 receptor ligand. The in vitro activity may be related to in vivo activity but may not be linearly correlated with binding affinity. In the in vitro assay, a compound can be tested for its activity toward H3 receptors and $IC_{50}$ obtained to determine the activity for a particular compound toward the H3 receptor.

Guanosine 5'-O-(3-[$^{35}$S]thio)triphosphate [GTPγS] Binding Assay

A GTPγS binding assay can be used to investigate antagonist properties of compounds in CHO cells (Chinese Hamster Ovary) transfected with human Histamine H3 receptor (hH3R). Membranes from CHO cells expressing hH3R (10 µg/well) are diluted in GTPγS assay buffer (20 mM Hepes, 10 mM $MgCl_2$, 100 mM NaCl, pH 7.4) and preincubated with saponine (3 µg/ml), GDP (10 µM) and PVT-WGA SPA beads (125 µg/well) (Amersham) for 30 minutes. To determine antagonist activity, (R)-α-methyl histamine (30 nM) is added in 96 well SPA plate with [$^{35}$S]GTPγS (0.2 nM) and various concentration of H3R antagonists. The GTPγS binding assay is started with addition of the mixture membrane/saponine/GDP and incubated for 90 minutes at room temperature. The amount of bound [$^{35}$S]GTPγS is determined by using the MicroBeta Trilux counter (PerkinElmer). The percentage of [$^{35}$S]GTPγS bound in each sample is calculated as a percentage of that bound control sample incubated in absence of H3 antagonist. Duplicate determinations are obtained for each concentration, and the data are analyzed using ExcelFit4 to obtain the $IC_{50}$.

$IC_{50}$ Values

At least one formula compound in accordance with the present disclosure may have an $IC_{50}$ value of less than about 1 µM. In a further embodiment, at least one compound of at least one formula described herein may have activity in at least one of the above referenced assays via an $IC_{50}$ value of between about 1 nm to about 1 µM. In an even further embodiment, at least one compound of at least one formula described herein may have activity in at least one of the above referenced assays via an $IC_{50}$ value of between about 2 nM to about 100 nM. In yet a further embodiment, at least one compound of at least one formula described herein may have activity in at least one of the above referenced assays via an $IC_{50}$ value of between about 2 nM and 50 nM. In one embodiment, at least one compound of at least one formula described herein may have activity in at least one of the above referenced assays via an $IC_{50}$ value of less than about 100 nM. In another embodiment, at least one compound of at least one formula described herein may have activity in at least one of the above referenced assays via an $IC_{50}$ value of less than about 50 nM. In yet another embodiment, at least one compound of at least one formula described herein may have activity in at least one of the above referenced assays via an $IC_{50}$ value of less than about 20 nM.

Set forth in Table 1 hereinbelow for the Example 1-34 compounds are $IC_{50}$ values that were generated in accordance with the GTPγS Binding Assay as essentially described hereinabove.

TABLE 1

| Example No. | GTPγS Binding $IC_{50}$ (nM) |
|---|---|
| 1 | 7.481 |
| 2 | 5.655 |
| 3 | 326.5 |
| 4 | 13.54 |
| 5 | 8.536 |
| 6 | >1111 |
| 7 | 8.817 |
| 8 | 4.943 |
| 9 | 121.2 |
| 10 | 8.064 |
| 11 | 5.767 |
| 12 | 1325 |
| 13 | 29.07 |
| 14 | 15.29 |
| 15 | 139.9 |
| 16 | >1111 |
| 17 | 14.24 |
| 18 | 5.981 |
| 19 | 1272 |
| 20 | 8.736 |
| 21 | 6.826 |
| 22 | 1009 |
| 23 | >1111 |
| 24 | 15.85 |
| 25 | 12.01 |
| 26 | >1111 |
| 27 | 12.03 |
| 28 | 5.281 |
| 29 | 575.9 |
| 30 | 16.32 |
| 31 | 6.962 |
| 32 | >1111 |
| 33 | 41.01 |
| 34 | 51.8 |

Incorporation by Reference

Incorporated by reference herein in their entireties are U.S. Provisional Patent Application No. 61/305,581, filed Feb. 18, 2010, entitled Solid Forms Comprising A Cyclopropyl Amide Derivative; and U.S. Patent Application No. 61/305,583, filed Feb. 18, 2010, entitled Processes For Making Cyclopropyl Amide Derivatives And Intermeciates Associated Therewith.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather defined by the claims appended hereto.

All temperatures are in degrees Celsius (° C.) and are uncorrected.

Unless otherwise noted, commercial reagents used in preparing the example compounds were used as received without additional purification.

Unless otherwise noted, the solvents used in preparing the example compounds were commercial anhydrous grades and were used without further drying or purification.

All starting materials are commercially available, unless stated otherwise.

The names of the products were determined using the naming software included in CambridgeSoft E-Notebook version 9.2 (Chemoffice 9.0.7).

The following abbreviations are employed herein: aq.: aqueous; br.: broad; Bu: butyl; calcd: calculated; Celite®: brand of diatomaceous earth filtering agent, registered trademark of Celite Corporation; d: doublet; dd: doublet of doublet; ddd: doublet of doublet of doublet; dddd: doublet of doublet of doublet of doublet; DABCO: 1,4-diazabicyclo [2.2.2]octane; DCE: dichloroethane; DCM: dichloromethane; DIPEA: N-ethyl-N-isopropylpropan-2-amine; DME: dimethyl ether; DMEA: dimethyl ethylamine; DMF: N,N-dimethyl formamide; DMSO: dimethyl sulfoxide; dq: doublet of quartet; dt: doublet of triplet; EDC: 1-ethyl-3-(3-dimethylaminopropyl)carbodiimide hydrochloride; ESI: electrospray ion source; EtOAc: ethyl acetate; EtOH: ethanol; g: gram; h: hour(s); $^1$H NMR: proton nuclear magnetic resonance; HBTU: O-Benzotriazole-N,N,N',N'-tetramethyl-uronium-hexafluoro-phosphate; HOBT: N-Hydroxybenzotriazole; HPLC: high pressure liquid chromatography; HRMS: high resolution mass spectrometry; iPrOH: iso-propanol; L: liter; m: multiplet; M: molar; mL: milliliter; MeOH: methanol; mg: milligram; MgSO$_4$: anhydrous magnesium sulfate (drying agent); MHz: megahertz; min: minute(s); mmol: millimole; mol: mole; MPLC: medium pressure liquid chromatography; MS: mass spectrometry; MTBE: methyl tert-butyl ether; NaHCO$_3$: sodium bicarbonate; NH$_4$Cl: ammonium chloride; ppm: parts per million; q: quartet; quin: quintet; rt: room temperature; s: singlet; sat: saturated; t: triplet; TEA: triethylamine; tBuOH: tert-butanol; td: triplet of doublet; TFA: trifluoroacetic acid; and THF: tetrahydrofuran.

Column chromatography was performed using 32-63 micron, 60 Å, silica gel with glass column and air pressure. MPLC was performed on an ISCO Companion instrument using pre-packaged disposable RediSep SiO$_2$ stationary phase at 5-100 mL/min, UV detection (190-760 nm range).

The mass spectra were recorded using electrospray (LC-MS; method A: column XTerra MS C8 2.5 µm 2.1×30 mm, buffer gradient H$_2$O 0.1% TFA: CH$_3$CN+0.04% TFA, MS: micromass ZMD/ammonium acetate buffer; method B: Agilent Zorbax SB-C8 column 1.8 µm, 2.1×30 mm, H$_2$O with 0.1% formic acid:MeCN with 0.05% formic acid) ionisation techniques. Alternatively, mass spectra were recorded on a Waters MS consisting of an Alliance 2795 (LC) and Waters Micromass ZQ detector at 120° C. The mass spectrometer was equipped with an electrospray ion source (ESI) operated in a positive or negative ion mode. The mass spectrometer was scanned between m/z 100-1000 with a scan time of 0.3 s.

The $^1$H NMR spectra were recorded on Varian NMR Spectrometer at 400 MHz or Varian Mercury 300 MHz. The $^1$H NMR spectra were interpreted using the processing software ACD/SpecManager version 10.02. Alternatively, they were recorded on a Bruker UltraShield Advance 400 MHz/54 mm spectrometer and processed with XWIN-NMR version 2.6 software. The chemical shifts (δ) are reported in parts-per-million from a tetramethylsilane internal standard.

Example 1

4-(trans-2-((R)-4-isopropyl-2-methylpiperazine-1-carbonyl)cyclopropyl)benzamide, diastereomeric Mixture

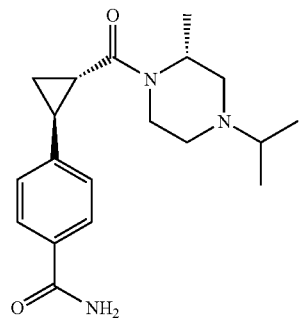 [SMILES: CC(C)N1CCN(C(=O)[C@H]2C[C@@H]2c2ccc(C(N)=O)cc2)[C@H](C)C1]

Intermediate 20 (655 mg, 2.28 mmol) was dissolved in DCE (20 mL). TEA (1.589 mL, 11.40 mmol) was added, followed by propan-2-one (0.338 mL, 4.56 mmol) and sodium triacetoxyborohydride (725 mg, 3.42 mmol). The reaction mixture was stirred overnight and washed with sat. NaHCO$_3$. The organic layer was dried over MgSO$_4$, filtered and concentrated under reduced pressure. The crude material was purified on preparative HPLC MS using the short high pH shallow gradient method (Mobile phase: 20-40% B; A: H$_2$O with 10 mM NH$_4$CO$_3$ and 0.375% NH$_4$OH v/v, B: CH$_3$CN, 10 min run) on XBridge Prep C18 OBD, 30×50 mm, 5 µm, Waters reverse phase column, providing 332 mg title compound (44.1%) as a solid (diastereomeric mixture). $^1$H NMR (400 MHz, CD$_3$OD) δ ppm 1.03 (dd, J=8.98, 6.64 Hz, 6H) 1.25 (d, J=6.64 Hz, 2H) 1.37 (br. s., 2H) 1.60 (ddd, J=9.28, 5.18, 4.30 Hz, 1H) 2.16 (br. s., 1H) 2.22-2.36 (m, 2H) 2.43 (br. s., 1H) 2.62-2.72 (m, 1H) 2.75 (d, J=11.33 Hz, 1H) 2.86 (dd, J=10.94, 2.73 Hz, 1H) 2.90-3.05 (m, 0.5H) 3.34-3.48 (m, 0.5H) 3.92-4.11 (m, 0.5H) 4.21-4.34 (m, 1H) 4.57-4.73 (m, 0.5H) 7.26 (d, J=8.20 Hz, 2H) 7.80 (d, J=8.59 Hz, 2H); for C$_{19}$H$_{28}$N$_3$O$_2$ 330.21760 [M+H]$^+$, found 330.21773.

Example 2

4-(trans-2-((R)-4-isopropyl-2-methylpiperazine-1-carbonyl)cyclopropyl)benzamide, isomer 1

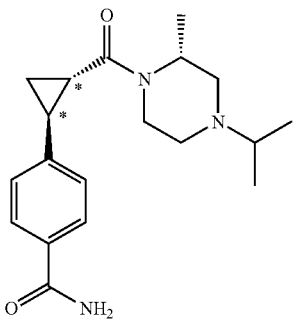 [SMILES: CC(C)N1CCN(C(=O)[C@H]2C[C@@H]2c2ccc(C(N)=O)cc2)[C@H](C)C1]

Note: * designates single isomer of unknown absolute stereochemistry.

Example 1 (304.0 mg, 0.92 mmol) (diastereomeric mixture) was separated on a MettlerToledo Minigram Supercritical Fluid Chromatography instrument using the following conditions: ChiralPak AD-H, 10×250 mm, 5 μm particle size, 10.0 mL/min, mobile phase: 55% EtOH with 0.1% DMEA, supercritical $CO_2$, regulator set to 100 Bar, column temperature set to 35° C., UV 215 nm, providing 120 mg isomer 1 (39.4%) and 104 mg isomer 2 (34.1%) as solids. The product was analyzed on chiral SFC (UV detection) using isocratic method (mobile phase: 55% EtOH with 0.1% DMEA, supercritical $CO_2$) on Chiral Pak AD-H, 10×250 mm, 5 μm particle size, giving an enantiomeric purity of 99%, $R_t$ 1.81 min (isomer 1) and 3.78 min (isomer 2). Isomer 1: $^1$H NMR (400 MHz, $CD_3OD$) δ ppm 1.02 (d, J=6.64 Hz, 3H) 1.02 (d, J=6.64 Hz, 3H) 1.25 (br. s., 1H) 1.37 (br. s., 3H) 1.52-1.67 (m, 1H) 2.07-2.36 (m, 3H) 2.42 (br. s., 1H) 2.67 (d, J=6.64 Hz, 1H) 2.75 (dt, J=11.33, 1.76 Hz, 1H) 2.85 (dddd, J=11.38, 3.37, 1.95, 1.66 Hz, 1H) 2.97 (t, J=12.89 Hz, 0.5H) 3.37 (t, J=11.33 Hz, 0.5H) 4.03 (d, J=11.33 Hz, 0.5H) 4.30 (d, J=12.89 Hz, 0.5H) 4.37 (br. s., 0.5H) 4.64 (br. s., 0.5H) 7.26 (d, J=8.20 Hz, 2H) 7.80 (d, J=8.20 Hz, 2H); HRMS m/z calcd for $C_{19}H_{28}N_3O_2$ 330.21760 $[M+H]^+$, found 330.21731; $[\alpha]_D$+156.8° (c 0.91, MeOH).

Example 3

4-(trans-2-((R)-4-isopropyl-2-methylpiperazine-1-carbonyl)cyclopropyl)benzamide, isomer 2

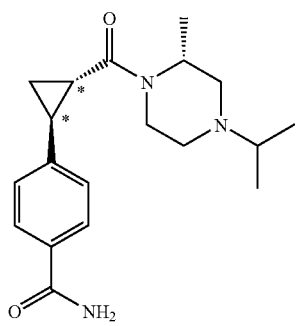

Note: * designates single isomer of unknown absolute stereochemistry.

This isomer was isolated in accordance with the chiral separation described in Example 2 and treated as described therein. The product was analyzed on chiral SFC (UV detection) using isocratic method (mobile phase: 55% EtOH with 0.1% DMEA, supercritical $CO_2$) on ChiralPak AD-H, 10×250 mm, 5 μm particle size, giving an enantiomeric purity of 99%, $R_t$ 1.81 min (isomer 1) and 3.78 min (isomer 2). Isomer 2: $^1$H NMR (400 MHz, $CD_3OD$) δ ppm 1.04 (d, J=6.64 Hz, 6H) 1.25 (d, J=7.03 Hz, 3H) 1.37 (br. s., 1H) 1.50-1.73 (m, 1H) 2.17 (t, J=10.94 Hz, 1H) 2.23-2.49 (m, 3H) 2.59-2.72 (m, 1H) 2.76 (d, J=11.33 Hz, 1H) 2.84 (t, J=9.77 Hz, 1H) 2.91-3.10 (m, 0.5H) 3.42 (t, J=11.52 Hz, 0.5H) 3.97 (d, J=14.84 Hz, 0.5H) 4.27 (d, J=12.11 Hz, 0.5H) 4.43 (br. s., 0.5H) 4.66 (br. s., 0.5H) 7.26 (d, J=8.59 Hz, 2H) 7.80 (d, J=8.20 Hz, 2H); HRMS m/z calcd for $C_{19}H_{28}N_3O_2$ 330.21760 $[M+H]^+$, found 330.21745; $[\alpha]_D$−234° (c 1.22, MeOH).

Example 4

4-(trans-2-((S)-4-isopropyl-2-methylpiperazine-1-carbonyl)cyclopropyl)benzamide, diastereomeric mixture

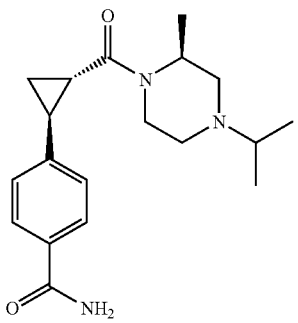 [SMILES: CC(C)N1CCN(C(=O)[C@H]2C[C@@H]2c2ccc(C(N)=O)cc2)[C@@H](C)C1]

Intermediate 21 (584 mg, 2.03 mmol) was dissolved in DCE (20 mL). TEA (1.416 mL, 10.16 mmol) was added, followed by propan-2-one (0.301 mL, 4.06 mmol) and sodium triacetoxyborohydride (646 mg, 3.05 mmol). The reaction mixture was stirred overnight and washed with sat $NaHCO_3$. The organic layer was dried over $MgSO_4$, filtered and concentrated under reduced pressure. The crude material was purified on preparative HPLC MS using the short high pH shallow gradient method (Mobile phase: 20-40% B; A: $H_2O$ with 10 mM $NH_4CO_3$ and 0.375% $NH_4OH$ v/v, B: $CH_3CN$, 10 min run) on XBridge Prep C18 OBD, 30×50 mm, 5 μm, Waters reverse phase column, providing 299 mg title compound (44.6%) as a solid (diastereomeric mixture). $^1$H NMR (400 MHz, $CD_3OD$) δ ppm 1.03 (dd, J=8.98, 6.64 Hz, 6H) 1.25 (d, J=7.03 Hz, 2H) 1.37 (br. s., 2H) 1.51-1.67 (m, 1H) 2.10-2.49 (m, 4H) 2.62-2.72 (m, 1H) 2.75 (d, J=11.33 Hz, 1H) 2.80-2.90 (m, 1H) 2.91-3.04 (m, 0.5H) 3.33-3.50 (m, 0.5H) 3.91-4.10 (m, 0.5H) 4.19-4.50 (m, 1H) 4.58-4.72 (m, 0.5H) 7.26 (d, J=8.20 Hz, 2H) 7.80 (d, J=8.59 Hz, 2H); HRMS m/z calcd for $C_{19}H_{28}N_3O_2$ 330.21760 $[M+H]^+$, found 330.21763.

Example 5

4-(trans-2-((S)-4-isopropyl-2-methylpiperazine-1-carbonyl)cyclopropyl)benzamide, isomer 1

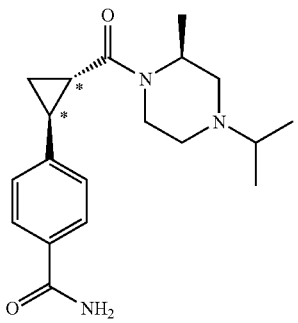 [SMILES: CC(C)N1CCN(C(=O)[C@H]2C[C@@H]2c2ccc(C(N)=O)cc2)[C@@H](C)C1]

Note: * designates single isomer of unknown absolute stereochemistry.

Example 4 (265.15 mg, 0.80 mmol) (diastereomeric mixture) was separated on a MettlerToledo Minigram Supercritical Fluid Chromatography instrument using the following conditions: ChiralPak AD-H, 10×250 mm, 5 μm particle size, 10.0 mL/min, mobile phase: 45% EtOH with 0.1% DMEA, supercritical $CO_2$, regulator set to 100 Bar, column temperature set to 35° C., UV 215 nm, providing 113 mg isomer 1 (42.5%) and 114 mg isomer 2 (42.8%) as solids. The product was analyzed on chiral SFC (UV detection) using isocratic method (mobile phase: 55% EtOH with 0.1% DMEA, supercritical $CO_2$) on Chiral Pak AD-H, 10×250 mm, 5 μm particle size, giving an enantiomeric purity of 99%, $R_t$ 1.85 min (isomer 1) and 2.43 min (isomer 2). Isomer 1: $^1$H NMR (400 MHz, $CD_3OD$) δ ppm 1.02 (d, J=6.64 Hz, 3H) 1.04 (d, J=6.64 Hz, 3H) 1.25 (d, J=6.64 Hz, 3H) 1.37 (br. s., 1H) 1.52-1.69 (m, 1H) 2.17 (t, J=11.33 Hz, 1H) 2.28 (br. s., 2H) 2.40 (d, J=8.98 Hz, 1H) 2.67 (septuplet, J=6.25 Hz, 1H) 2.76 (d, J=11.72 Hz, 1H) 2.84 (t, J=10.55 Hz, 1H) 2.92-3.04 (m, 0.5H) 3.38-3.48 (m, 0.5H) 3.97 (d, J=12.11 Hz, 0.5H) 4.27 (d, J=13.67 Hz, 0.5H) 4.43 (br. s., 0.5H) 4.66 (br. s., 0.5H) 7.26 (d, J=8.59 Hz, 2H) 7.78-7.83 (m, 2H); HRMS m/z calcd for $C_{19}H_{28}N_3O_2$ 330.21760 $[M+H]^+$, found 330.21708; $[α]_D$+ 256.3° (c 1.85, MeOH).

Example 6

4-(trans-2-((S)-4-isopropyl-2-methylpiperazine-1-carbonyl)cyclopropyl)benzamide, isomer 2

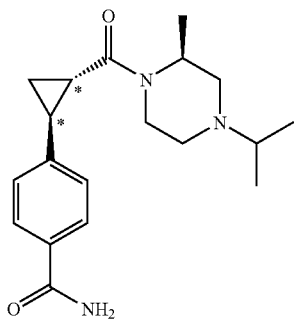 [SMILES: CC(C)N1CCN(C(=O)[C@H]2C[C@@H]2c2ccc(C(N)=O)cc2)[C@@H](C)C1]

Note: * designates single isomer of unknown absolute stereochemistry.

This isomer was isolated in accordance with the chiral separation described in Example 5 and treated as described therein. The product was analyzed on chiral SFC (UV detection) using isocratic method (mobile phase: 55% EtOH with 0.1% DMEA, supercritical $CO_2$) on ChiralPak AD-H, 10×250 mm, 5 μm particle size, giving an enantiomeric purity of 99%, $R_t$ 1.85 min (isomer 1) and 2.43 min (isomer 2). Isomer 2: $^1$H NMR (400 MHz, $CD_3OD$) δ ppm 1.02 (d, J=6.64 Hz, 3H) 1.05 (d, J=6.64 Hz, 3H) 1.16-1.28 (m, 1H) 1.29-1.47 (m, 3H) 1.53-1.66 (m, 1H) 2.07-2.37 (m, 3H) 2.42 (br. s., 1H) 2.67 (septuplet, J=6.64 Hz, 1H) 2.75 (dt, J=11.43, 1.90 Hz, 1H) 2.80-2.91 (m, 1H) 2.91-3.08 (m, 0.5H) 3.32-3.45 (m, 0.5H) 4.03 (d, J=13.67 Hz, 0.5H) 4.30 (d, J=12.50 Hz, 0.5H) 4.37 (br. s., 0.5H) 4.64 (br. s., 0.5H) 7.26 (d, J=8.20 Hz, 2H) 7.80 (d, J=8.20 Hz, 2H); HRMS m/z calcd for $C_{19}H_{28}N_3O_2$ 330.21760 $[M+H]^+$, found 330.21694; $[α]_D$− 153.6° (c 0.92, MeOH).

Example 7

4-(trans-2-((R)-4-cyclobutyl-2-methylpiperazine-1-carbonyl)cyclopropyl)benzamide, diastereomeric mixture

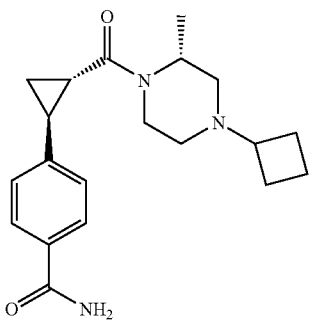 [SMILES: C[C@@H]1CN(C2CCC2)CCN1C(=O)[C@H]1C[C@@H]1c1ccc(C(N)=O)cc1]

Intermediate 20 was dissolved in DCE (13.0 mL). TEA (0.958 mL, 6.87 mmol) was added, followed by cyclobutanone (193 mg, 2.75 mmol) and sodium triacetoxyborohydride (437 mg, 2.06 mmol). The reaction mixture was stirred overnight and washed with sat. $NaHCO_3$. The organic layer was dried over $MgSO_4$, filtered and concentrated under reduced pressure. The crude material was purified on preparative HPLC MS using the short high pH shallow gradient method (Mobile phase: 20-40% B; A: $H_2O$ with 10 mM $NH_4CO_3$ and 0.375% $NH_4OH$ v/v, B: $CH_3CN$, 10 min run) on XBridge Prep C18 OBD, 30×50 mm, 5 μm, Waters reverse phase column, providing 159 mg title compound (33.9%) as a solid (diastereomeric mixture). $^1$H NMR (400 MHz, $CD_3OD$) δ ppm 1.27 (d, J=7.03 Hz, 2H) 1.39 (br. s., 2H) 1.59 (ddd, J=9.18, 5.27, 4.30 Hz, 1H) 1.65-1.78 (m, 3H) 1.78-1.98 (m, 3H) 1.98-2.10 (m, 2H) 2.20-2.34 (m, 1H) 2.42 (br. s., 1H) 2.62-2.77 (m, 2H) 2.78-2.90 (m, 1H) 2.90-3.05 (m, 1H) 3.94-4.10 (m, 1H) 4.23-4.35 (m, 1H) 7.25 (d, J=8.59 Hz, 2H) 7.80 (d, J=8.20 Hz, 2H); HRMS m/z calcd for $C_{20}H_{28}N_3O_2$ 342.21760 $[M+H]^+$, found 342.21804.

Example 8

4-((trans)-2-((R)-4-cyclobutyl-2-methylpiperazine-1-carbonyl)cyclopropyl)benzamide, isomer 1

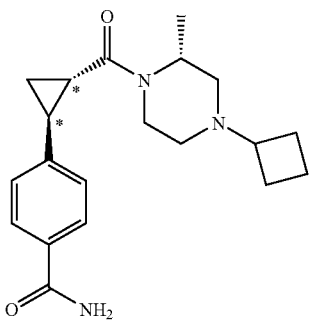

Note: * designates single isomer of unknown absolute stereochemistry.

Example 7 (138 mg, 0.40 mmol) (diastereomeric mixture) was separated on a MettlerToledo Minigram Supercritical Fluid Chromatography instrument using the following conditions: ChiralPak AD-H, 10×250 mm, 5 μm particle size, 10.0 mL/min, mobile phase: 55% iPrOH with 0.1% DMEA, supercritical $CO_2$, regulator set to 100 Bar, column temperature set to 35° C., UV 215 nm, providing 57.8 mg isomer 1 (41.9%) and 56.5 mg isomer 2 (41.0%) as solids. The product was analyzed on chiral SFC (UV detection) using isocratic method (mobile phase: 55% EtOH with 0.1% DMEA, supercritical $CO_2$) on ChiralPak AD-H, 10×250 mm, 5 μm particle size, giving an enantiomeric purity of 99%, $R_t$ 1.92 min (isomer 1) and 3.46 min (isomer 2). Isomer 1: $^1H$ NMR (400 MHz, $CD_3OD$) δ ppm 1.26 (br. s., 1H) 1.38 (br. s., 3H) 1.59 (ddd, J=9.57, 4.69, 4.49 Hz, 1H) 1.65-1.77 (m, 3H) 1.77-1.98 (m, 3H) 1.98-2.09 (m, 2H) 2.22-2.31 (m, 1H) 2.43 (br. s., 1H) 2.63-2.74 (m, 2H) 2.84 (d, J=11.33 Hz, 1H) 2.96 (t, J=12.89 Hz, 0.5H), 3.36 (t, J=12.30 Hz, 0.5H) 4.04 (d, J=12.11 Hz, 0.5H) 4.31 (d, J=12.11 Hz, 0.5H) 4.38 (br. s., 0.5H) 4.65 (br. s., 0.5H) 7.25 (d, J=8.20 Hz, 2H), 7.80 (d, J=8.20 Hz, 2H); HRMS m/z calcd for $C_{20}H_{28}N_3O_2$ 342.21760 [M+H]$^+$, found 342.21771; $[α]_D$+156.3° (c 2.20, MeOH).

Example 9

4-((trans)-2-((R)-4-cyclobutyl-2-methylpiperazine-1-carbonyl)cyclopropyl)benzamide, isomer 2

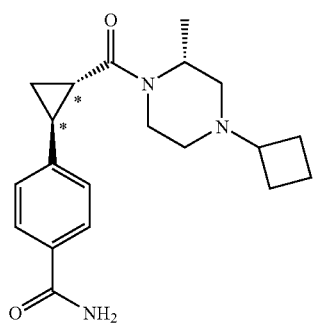 [SMILES: C[C@@H]1CN(C2CCC2)CCN1C(=O)[C@H]1C[C@@H]1c1ccc(C(N)=O)cc1]

Note: * designates single isomer of unknown absolute stereochemistry.

This isomer was isolated in accordance with the chiral separation described in Example 8 and treated as described therein. The product was analyzed on chiral SFC (UV detection) using isocratic method (mobile phase: 55% EtOH with 0.1% DMEA, supercritical $CO_2$) on ChiralPak AD-H, 10×250 mm, 5 μm particle size, giving an enantiomeric purity of 99%, $R_t$ 1.92 min (isomer 1) and 3.46 min (isomer 2). Isomer 2: $^1H$ NMR (400 MHz, $CD_3OD$) δ ppm 1.27 (d, J=7.03 Hz, 3H) 1.33-1.42 (m, 1H) 1.53-1.65 (m, 1H) 1.67-1.77 (m, 3H) 1.78-1.87 (m, 1H) 1.87-1.95 (m, 1H) 1.98-2.07 (m, 3H) 2.27 (br. s., 1H) 2.42 (br. s., 1H) 2.63-2.76 (m, 2H) 2.83 (t, J=9.96 Hz, 1H) 2.96 (t, J=12.50 Hz, 0.5H) 3.41 (t, J=11.33 Hz, 0.5H) 3.98 (d, J=12.11 Hz, 0.5H) 4.28 (d, J=12.11 Hz, 0.5H) 4.44 (br. s., 0.5H) 4.67 (br. s., 0.5H) 7.25 (d, J=8.20 Hz, 2H) 7.80 (d, J=8.59 Hz, 2H); HRMS m/z calcd for $C_{20}H_{28}N_3O_2$ 342.21760 [M+H]$^+$, found 342.21749; $[α]_D$−223.7° (c 2.20, MeOH).

Example 10

4-(trans-2-((S)-4-cyclobutyl-2-methylpiperazine-1-carbonyl)cyclopropyl)benzamide, diastereomeric mixture

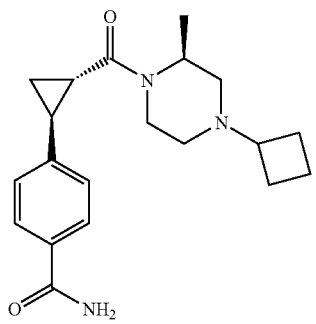

Intermediate 21 (478 mg, 1.66 mmol) was dissolved in DCE (15.0 mL). TEA (1.159 mL, 8.32 mmol) was added, followed by cyclobutanone (233 mg, 3.33 mmol) and sodium triacetoxyborohydride (529 mg, 2.50 mmol). The reaction mixture was stirred overnight and was washed with sat. $NaHCO_3$. The organic layer was dried over $MgSO_4$, filtered and concentrated under reduced pressure. The crude material was purified on preparative HPLC MS using the short high pH shallow gradient method (Mobile phase: 20-40% B; A: $H_2O$ with 10 mM $NH_4CO_3$ and 0.375% $NH_4OH$ v/v, B: $CH_3CN$, 10 min run) on XBridge Prep C18 OBD, 30×50 mm, 5 μm, Waters reverse phase column, providing 192 mg title compound (33.8%) as a solid (diastereomeric mixture). $^1H$ NMR (400 MHz, $CD_3OD$) δ ppm 1.27 (d, J=6.64 Hz, 2H) 1.39 (br. s., 2H) 1.59 (ddd, J=9.18, 5.27, 4.30 Hz, 1H) 1.68-1.98 (m, 6H) 1.98-2.11 (m, 2H) 2.19-2.35 (m, 1H) 2.42 (br. s., 1H) 2.62-2.77 (m, 2H) 2.77-2.90 (m, 1H) 2.90-3.06 (m, 1H) 3.92-4.12 (m, 1H) 4.22-4.36 (m, 1H) 7.25 (d, J=8.59 Hz, 2H) 7.80 (d, J=7.81 Hz, 2H); HRMS m/z calcd for $C_{20}H_{28}N_3O_2$ 342.21760 [M+H]$^+$, found 342.21783.

Example 11

4-((trans)-2-((S)-4-cyclobutyl-2-methylpiperazine-1-carbonyl)cyclopropyl)benzamide, isomer 1

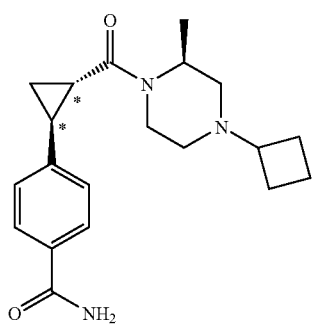 [SMILES: C[C@H]1CN(C2CCC2)CCN1C(=O)[C@H]1C[C@@H]1c1ccc(C(N)=O)cc1]

Note: * designates single isomer of unknown absolute stereochemistry.

Example 10 (173 mg, 0.51 mmol) (diastereomeric mixture) was separated on a MettlerToledo Minigram Supercritical Fluid Chromatography instrument using the following conditions: ChiralPak AD-H, 10×250 mm, 5 μm particle size, 10.0 mL/min, mobile phase: 40% EtOH with 0.1% DMEA, supercritical $CO_2$, regulator set to 100 Bar, column temperature set to 35° C., UV 215 nm, providing 73.0 mg isomer 1 (42.2%) and 72.7 mg isomer 2 (42.0%) as solids. The product was analyzed on chiral SFC (UV detection) using isocratic method (mobile phase: 55% EtOH with 0.1% DMEA, supercritical $CO_2$) on Chiral Pak AD-H, 10×250 mm, 5 μm particle size, giving an enantiomeric purity of 99%, $R_t$ 1.97 min (isomer 1) and 2.62 min (isomer 2). Isomer 1: $^1$H NMR (400 MHz, $CD_3OD$) δ ppm 1.27 (d, J=7.03 Hz, 3H) 1.33-1.42 (m, 1H) 1.53-1.65 (m, 1H) 1.65-1.77 (m, 3H) 1.78-1.97 (m, 3H) 1.97-2.09 (m, 2H) 2.27 (br. s., 1H) 2.42 (br. s., 1H) 2.63-2.76 (m, 2H) 2.77-2.89 (m, 1H) 2.96 (t, J=12.11 Hz, (m, 0.5H) 3.99 (d, J=11.72 Hz, 0.5H) 4.28 (d, J=12.89 Hz, 0.5H) 4.44 (br. s., 0.5H) 4.67 (br. s., 0.5H) 7.25 (d, J=8.20 Hz, 2H) 7.80 (d, J=8.59 Hz, 2H); HRMS m/z calcd for $C_{20}H_{28}N_3O_2$ 342.21760 [M+H]$^+$, found 342.21754; $[α]_D$+225.1° (c 2.26, MeOH).

Example 12

4-((trans)-2-((S)-4-cyclobutyl-2-methylpiperazine-1-carbonyl)cyclopropyl)benzamide, isomer 2

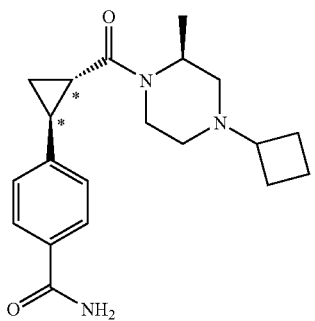 [SMILES: C[C@H]1CN(C2CCC2)CCN1C(=O)[C@H]1C[C@@H]1c1ccc(C(N)=O)cc1]

Note: * designates single isomer of unknown absolute stereochemistry.

This isomer was isolated in accordance with the chiral separation described in Example 11 and treated as described therein. The product was analyzed on chiral SFC (UV detection) using isocratic method (mobile phase: 55% EtOH with 0.1% DMEA, supercritical $CO_2$) on ChiralPak AD-H, 10×250 mm, 5 μm particle size, giving an enantiomeric purity of 99%, $R_t$ 1.97 min (isomer 1) and 2.62 min (isomer 2). Isomer 2: $^1$H NMR (400 MHz, $CD_3OD$) δ ppm 1.26 (br. s., 1H) 1.31-1.45 (m, 3H) 1.59 (ddd, J=9.18, 4.88, 4.69 Hz, 1H) 1.65-1.77 (m, 3H) 1.77-1.87 (m, 1H) 1.87-1.97 (m, 2H) 1.98-2.08 (m, 2H) 2.21-2.30 (m, 1H) 2.36-2.49 (m, 1H) 2.63-2.75 (m, 2H) 2.84 (d, J=11.33 Hz, 1H) 2.89-3.03 (m, 0.5H) 3.36-3.42 (m, 0.5H) 3.97-4.09 (m, 0.5H) 4.25-4.35 (m, 0.5H) 4.35-4.43 (m, 0.5H) 4.58-4.71 (m, 0.5H) 7.25 (d, J=8.59 Hz, 2H) 7.80 (d, J=8.20 Hz, 2H); HRMS m/z calcd for $C_{20}H_{28}N_3O_2$ 342.21760 [M+H]$^+$, found 342.21773; $[α]_D$-158.2° (c 2.90, MeOH).

Example 13

4-(trans-2-((R)-4-cyclobutyl-2-ethylpiperazine-1-carbonyl)cyclopropyl)benzamide, diastereomeric mixture

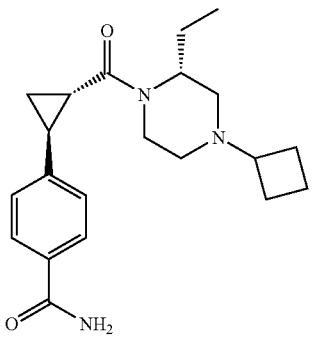 [SMILES: CC[C@@H]1CN(C2CCC2)CCN1C(=O)[C@H]1C[C@@H]1c1ccc(C(N)=O)cc1]

Intermediate 22 (335 mg, 1.11 mmol) was dissolved in DCE (10 mL). TEA (0.774 mL, 5.55 mmol) was added, followed by cyclobutanone (156 mg, 2.22 mmol) and sodium triacetoxyborohydride (353 mg, 1.67 mmol). The reaction mixture was stirred overnight and concentrated under reduced pressure. The residue was redissolved in DCM, washed with sat. $NaHCO_3$, dried over $MgSO_4$, filtered and concentrated under reduced pressure. The crude material was purified on preparative HPLC UV using the long high pH shallow gradient method (Mobile phase: 30-50% B; A: $H_2O$ with 10 mM $NH_4CO_3$ and 0.375% $NH_4OH$ v/v, B: $CH_3CN$, 30 min run) on XBridge Prep C18 OBD, 50×250 mm, 10μ, Waters reverse phase column, providing 309 mg title compound (78%) as a solid (diastereomeric mixture). $^1$H NMR (400 MHz, $CD_3OD$) δ ppm 0.69 (t, J=7.62 Hz, 1H) 0.90 (ddd, J=19.34, 7.62, 7.42 Hz, 2H) 1.32-1.44 (m, 1H) 1.54-1.63 (m, 1H) 1.63-2.12 (m, 10H) 2.22-2.52 (m, 2H) 2.61-2.75 (m, 1H) 2.75-2.95 (m, 3H) 4.02 (br. s., 0.5H) 4.15 (br. s., 0.5H) 4.36 (br. s., 0.5H) 4.48 (br. s., 0.5H) 7.20-7.28 (m, 2H) 7.80 (d, J=8.20 Hz, 2H); HRMS m/z calcd for $C_{21}H_{30}N_3O_2$ 356.23325 [M+H]$^+$, found 356.23326.

Example 14

4-(trans-2-((R)-4-cyclobutyl-2-ethylpiperazine-1-carbonyl)cyclopropyl)benzamide, isomer 1

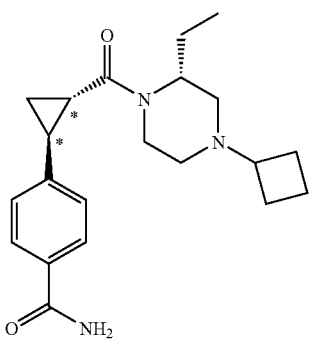

Note: * designates single isomer of unknown absolute stereochemistry.

Example 13 (150 mg, 0.42 mmol) (diastereomeric mixture) was separated on a MettlerToledo Minigram Supercritical Fluid Chromatography instrument using the following conditions: ChiralPak AD-H, 10×250 mm, 5 μm particle size, 10.0 mL/min, mobile phase: 55% iPrOH with 0.1% DMEA, supercritical $CO_2$, regulator set to 100 Bar, column temperature set to 35° C., UV 215 nm, providing 69.4 mg isomer 1 (93%) and 69.4 mg isomer 2 (93.0%) as solids. The product was analyzed on chiral SFC (UV detection) using isocratic method (mobile phase: 55% iPrOH with 0.1% DMEA, supercritical $CO_2$) on ChiralPak AD-H, 10×250 mm, 5 μm particle size, giving an enantiomeric purity of 99%, $R_t$ 1.80 min (isomer 1) and 2.66 min (isomer 2). Isomer 1: $^1$H NMR (400 MHz, $CD_3OD$) δ ppm 0.90 (dt, J=19.24, 7.57 Hz, 3H) 1.32-1.44 (m, 1H) 1.53-1.61 (m, 1H) 1.65-1.86 (m, 6H) 1.86-1.98 (m, 2H) 1.98-2.10 (m, 2H) 2.21-2.33 (m, 1H) 2.39-2.53 (m, 1H) 2.62-2.74 (m, 1H) 2.78-2.94 (m, 3H) 4.01-4.17 (m, 1H) 4.31-4.51 (m, 1H) 7.25 (d, J=7.03 Hz, 2H) 7.80 (d, J=8.20 Hz, 2H); HRMS m/z calcd $C_{21}H_{30}N_3O_2$ 356.2333 [M+H]$^+$; [α]$_D$+181° (c 0.48, MeOH).

Example 15

4-(trans-2-((R)-4-cyclobutyl-2-ethylpiperazine-1-carbonyl)cyclopropyl)benzamide, isomer 2

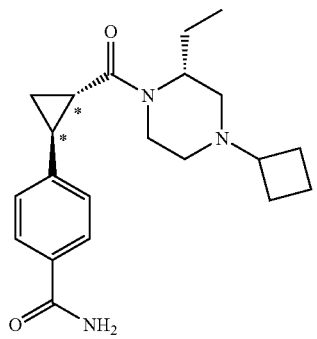 [SMILES: CC[C@@H]1CN(C2CCC2)CCN1C(=O)[C@H]1C[C@@H]1c1ccc(C(N)=O)cc1]

Note: * designates single isomer of unknown absolute stereochemistry.

This isomer was isolated in accordance with the chiral separation described in Example 14 and treated as described therein. The product was analyzed on chiral SFC (UV detection) using isocratic method (mobile phase: 55% iPrOH with 0.1% DMEA, supercritical $CO_2$) on ChiralPak AD-H, 10×250 mm, 5 μm particle size, giving an enantiomeric purity of 99%, $R_t$ 1.80 min (isomer 1) and 2.66 min (isomer 2). Isomer 2: $^1$H NMR (400 MHz, $CD_3OD$) δ ppm 0.69 (br. s., 2H) 0.88 (br. s., 1H) 1.37 (br. s., 1H) 1.54-2.12 (m, 11H) 2.18-2.48 (m, 2H) 2.67 (br. s., 1H) 2.74-2.94 (m, 3H) 3.92-4.22 (m, 1H) 4.28-4.54 (m, 1H) 7.24 (br. s., 2H) 7.79 (br. s., 2H); HRMS m/z calcd for $C_{21}H_{30}N_3O_2$ 356.2333 [M+H]$^+$, found 356.2325; [α]$_D$−209° (c 0.54, MeOH).

Example 16

4-(trans-2-((S)-4-cyclobutyl-2-ethylpiperazine-1-carbonyl)cyclopropyl)benzamide, diastereomeric mixture

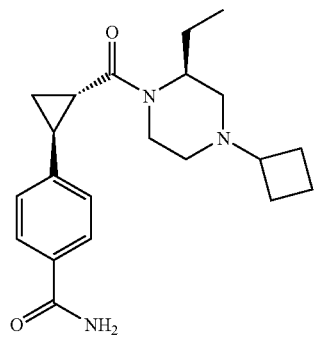 [SMILES: CC[C@H]1CN(C2CCC2)CCN1C(=O)[C@H]1C[C@@H]1c1ccc(C(N)=O)cc1]

Intermediate 23 (322 mg, 1.07 mmol) was dissolved in DCE (10 mL). TEA (0.746 mL, 5.35 mmol) was added, followed by cyclobutanone (150 mg, 2.14 mmol) and sodium triacetoxyborohydride (340 mg, 1.61 mmol). The reaction mixture was stirred overnight and concentrated under reduced pressure. The residue was redissolved in DCM, washed with sat. $NaHCO_3$, dried over $MgSO_4$, filtered and concentrated under reduced pressure. The crude material was purified on preparative HPLC UV using the long high pH shallow gradient method (Mobile phase: 40-60% B; A: $H_2O$ with 10 mM $NH_4CO_3$ and 0.375% $NH_4OH$ v/v, B: $CH_3CN$, 30 min run) on XBridge Prep C18 OBD, 50×250 mm, 10μ, Waters reverse phase column, providing 294 mg title compound (77%) as a white solid (diastereomeric mixture). $^1$N NMR (400 MHz, $CD_3OD$) δ ppm 0.69 (t, J=7.62 Hz, 1H) 0.90 (dt, J=19.24, 7.57 Hz, 2H) 1.33-1.44 (m, 1H) 1.50-2.12 (m, 11H) 2.22-2.52 (m, 2H) 2.61-2.75 (m, 1H) 2.75-2.94 (m, 3H) 3.94-4.09 (m, 0.5H) 4.15 (br. s., 0.5H) 4.35 (d, J=13.28 Hz, 0.5H) 4.42-4.53 (m, 0.5H) 7.21-7.28 (m, 2H) 7.80 (d, J=8.20 Hz, 2H); HRMS m/z calcd for $C_{21}H_{30}N_3O_2$ 356.23325 [M+H]$^+$, found 356.23294.

Example 17

4-(trans-2-((S)-4-cyclobutyl-3-methylpiperazine-1-carbonyl)cyclopropyl)benzamide, diastereomeric mixture

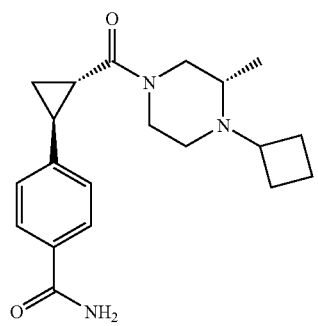 [SMILES: C[C@H]1CN(C(=O)[C@H]2C[C@@H]2c2ccc(C(N)=O)cc2)CCN1C1CCC1]

Intermediate 14 (300 mg, 1.46 mmol) was dissolved in DMF (15 mL). DIPEA (1.277 mL, 7.31 mmol) was added, followed by HOBT (296 mg, 2.19 mmol), EDC (420 mg, 2.19 mmol) and Intermediate 8 (399 mg, 1.75 mmol). The reaction mixture was stirred at rt overnight. The reaction mixture was concentrated under reduced pressure, redissolved in DCM, washed with sat. NaHCO$_3$, dried over MgSO$_4$, filtered and concentrated under reduced pressure. The crude material was purified on preparative HPLC MS using the long high pH shallow gradient method (Mobile phase: 5-95% B; A: H$_2$O with 10 mM NH$_4$CO$_3$ and 0.375% NH$_4$OH v/v, B: CH$_3$CN, 25 mM. run) on XBridge Prep C18 OBD, 30×150 mm, 5μ, Waters reverse phase column. Fractions were combined and lyophilized to provide 338 mg title compound (67.6%) as a solid (diastereomeric mixture). $^1$H NMR (400 MHz, CD$_3$OD) δ ppm 0.93 (d, J=6.25 Hz, 1H) 0.98-1.05 (m, 2H) 1.33-1.43 (m, 1H) 1.52-1.76 (m, 3H) 1.85-2.14 (m, 4H) 2.17-2.36 (m, 2H) 2.37-2.50 (m, 1H) 2.50-2.79 (m, 2H) 3.02-3.15 (m, 1H) 3.25 (ddd, J=13.48, 7.03, 6.84 Hz, 1H) 3.52-3.77 (m, 3H) 7.26 (d, J=8.20 Hz, 2H) 7.80 (d, J=7.81 Hz, 2H); HRMS m/z calcd for C$_{20}$H$_{28}$N$_3$O$_2$ 342.21760 [M+H]$^+$, found 342.21790.

Example 18

4-((trans)-2-((S)-4-cyclobutyl-3-methylpiperazine-1-carbonyl)cyclopropyl)benzamide, isomer 1

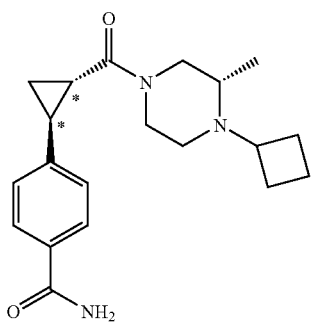 [SMILES: C[C@H]1CN(C(=O)[C@H]2C[C@@H]2c2ccc(C(N)=O)cc2)CCN1C1CCC1]

Note: * designates single isomer of unknown absolute stereochemistry.

Example 17 (310.4 mg, 0.91 mmol) (diastereomeric mixture) was separated on a MettlerToledo Minigram Supercritical Fluid Chromatography instrument using the following conditions: ChiralPak AD-H, 10×250 mm, 5 μm particle size, 10.0 mL/min, mobile phase: 40% EtOH with 0.1% DMEA, supercritical CO$_2$, regulator set to 100 Bar, column temperature set to 35° C., UV 215 nm, providing 83.2 mg isomer 1 (26.8%) and 132.1 mg isomer 2 (42.6%) as solids. The product was analyzed on chiral SFC (UV detection) using isocratic method (mobile phase: 55% EtOH with 0.1% DMEA, supercritical CO$_2$) on Chiral Pak AD, 4.6×250 mm, 20 μm particle size, giving an enantiomeric purity of 99%, R$_t$ 1.92 min (isomer 1) and 2.85 min (isomer 2). Isomer 1: $^1$H NMR (400 MHz, CD$_3$OD) δ ppm 0.93-1.07 (m, 3H) 1.29-1.44 (m, 1H) 1.51-1.64 (m, 1H) 1.64-1.75 (m, 2H) 1.90 (quin, J=9.77 Hz, 1H) 1.95-2.14 (m, 3H) 2.14-2.37 (m, 2H) 2.40-2.81 (m, 3H) 3.00-3.16 (m, 1H) 3.23 (dd, J=13.09, 7.23 Hz, 0.5H) 3.45 (dd, J=13.28, 6.64 Hz, 0.5H) 3.53-3.63 (m, 1H) 3.63-3.90 (m, 2H) 7.25 (d, J=8.20 Hz, 2H) 7.80 (d, J=8.20 Hz, 2H); HRMS m/z calcd for C$_{20}$H$_{28}$N$_3$O$_2$ 342.21760 [M+H]$^+$, found 342.21771; [α]$_D$+181.6° (c 3.03, MeOH).

Example 19

4-((trans)-2-((S)-4-cyclobutyl-3-methylpiperazine-1-carbonyl)cyclopropyl)benzamide, isomer 2

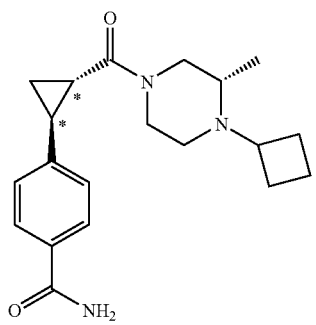 [SMILES: C[C@H]1CN(C(=O)[C@H]2C[C@@H]2c2ccc(C(N)=O)cc2)CCN1C1CCC1]

Note: * designates single isomer of unknown absolute stereochemistry.

This isomer was isolated in accordance with the chiral separation described in Example 18 and treated as described therein. The product was analyzed on chiral SFC (UV detection) using isocratic method (mobile phase: 55% EtOH with 0.1% DMEA, supercritical CO$_2$) on ChiralPak AD, 4.6×250 mm, 20 μm particle size, giving an enantiomeric purity of 99%, R$_t$ 1.92 min (isomer 1) and 2.85 min (isomer 2). Isomer 2: $^1$H NMR (400 MHz, CD$_3$OD) δ ppm 0.89-1.05 (m, 3H) 1.31-1.44 (m, 1H) 1.55-1.65 (m, 1H) 1.65-1.74 (m, 2H) 1.83-1.96 (m, 1H) 1.96-2.04 (m, 2H) 2.04-2.14 (m, 1H) 2.15-2.35 (m, 2H) 2.36-2.48 (m, 1H) 2.51-2.77 (m, 2H) 3.01-3.14 (m, 1H) 3.25 (dd, J=13.09, 7.23 Hz, 0.5H) 3.47 (dd, J=13.48, 6.05 Hz, 0.5H) 3.55 (ddd, J=12.99, 7.91, 3.32 Hz, 0.5H) 3.59-3.67 (m, 0.5H) 3.68-3.80 (m, 2H) 7.25 (dd, J=8.20, 1.95 Hz, 2H) 7.80 (d, J=8.20 Hz, 2H); HRMS m/z calcd for C$_{20}$H$_{28}$N$_3$O$_2$ 342.21760 [M+H]$^+$, found 342.21787; [α]$_D$−190.0° (c 2.69, MeOH).

Example 20

4-(trans-2-((R)-4-cyclobutyl-3-methylpiperazine-1-carbonyl)cyclopropyl)benzamide, diastereomeric mixture

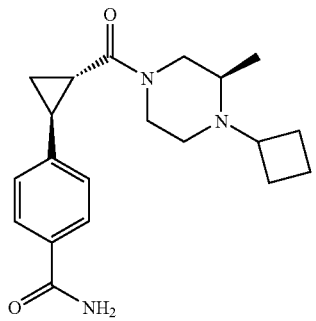 [SMILES: C[C@@H]1CN(C(=O)[C@H]2C[C@@H]2c2ccc(C(N)=O)cc2)CCN1C1CCC1]

Intermediate 14 (300 mg, 1.46 mmol) was dissolved in DMF (15 mL). DIPEA (1.277 mL, 7.31 mmol) was added, followed by HOBT (296 mg, 2.19 mmol), EDC (420 mg, 2.19 mmol) and Intermediate 5 (399 mg, 1.75 mmol). The reaction mixture was stirred at rt overnight. The reaction mixture was concentrated under reduced pressure, redissolved in DCM, washed with sat. NaHCO$_3$, dried over MgSO$_4$, filtered and concentrated under reduced pressure. The crude material was purified on preparative HPLC MS using the long high pH shallow gradient method (Mobile phase: 5-95% B; A: H$_2$O with 10 mM NH$_4$CO$_3$ and 0.375% NH$_4$OH v/v, B: CH$_3$CN, 25 min run) on XBridge Prep C18 OBD, 30×150 mm, 5μ, Waters reverse phase column. Fractions were combined and lyophilized to provide 360 mg (72.0%) as a solid (diastereomeric mixture). $^1$H NMR (400 MHz, CD$_3$OD) δ ppm 0.93 (d, J=6.64 Hz, 1H) 1.02 (d, J=6.25 Hz, 2H) 1.33-1.43 (m, 1H) 1.52-1.75 (m, 3H) 1.85-2.15 (m, 4H) 2.16-2.36 (m, 2H) 2.36-2.50 (m, 1H) 2.50-2.78 (m, 2H) 3.01-3.16 (m, 1H) 3.19-3.29 (m, 1H) 3.41-3.87 (m, 3H) 7.26 (d, J=8.20 Hz, 2H) 7.80 (d, J=7.81 Hz, 2H); HRMS m/z calcd for C$_{20}$H$_{28}$N$_3$O$_2$ 342.21760 [M+H]$^+$, found 342.21779.

Example 21

4-((trans)-2-((R)-4-cyclobutyl-3-methylpiperazine-1-carbonyl)cyclopropyl)benzamide, isomer 1

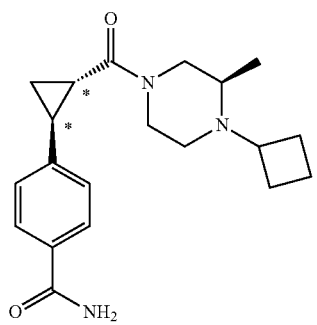 [SMILES: C[C@@H]1CN(C(=O)[C@H]2C[C@@H]2c2ccc(C(N)=O)cc2)CCN1C1CCC1]

Note: * designates single isomer of unknown absolute stereochemistry.

Example 20 (317.7 mg, 0.93 mmol) (diastereomeric mixture) was separated on a MettlerToledo Minigram Supercritical Fluid Chromatography instrument using the following conditions: ChiralPak AD-H, 10×250 mm, 5 μm particle size, 10.0 mL/min, mobile phase: 40% EtOH with 0.1% DMEA, supercritical CO$_2$, regulator set to 100 Bar, column temperature set to 35° C., UV 215 nm, providing 133.3 mg isomer 1 (41.9%) and 128.9 mg isomer 2 (40.6%) as solids. The product was analyzed on chiral SFC (UV detection) using isocratic method (mobile phase: 55% EtOH with 0.1% DMEA, supercritical CO$_2$) on Chiral Pak AD, 4.6×250 mm, 20 μm particle size, giving an enantiomeric purity of 99%, R$_t$ 1.97 min (isomer 1) and 2.53 min (isomer 2). Isomer 1: $^1$H NMR (400 MHz, CD$_3$OD) δ ppm 0.87-1.07 (m, 3H) 1.31-1.42 (m, 1H) 1.54-1.75 (m, 3H) 1.83-2.04 (m, 3H) 2.04-2.14 (m, 1H) 2.15-2.35 (m, 2H) 2.35-2.48 (m, 1H) 2.49-2.78 (m, 2H) 3.01-3.13 (m, 1H) 3.25 (dd, J=13.09, 7.23 Hz, 0.5H) 3.46 (dd, J=13.28, 5.86 Hz, 0.5H) 3.50-3.82 (m, 3H) 7.25 (d, J=6.64 Hz, 2H) 7.80 (d, J=8.20 Hz, 2H); HRMS m/z calcd for C$_{20}$H$_{28}$N$_3$O$_2$ 342.21760 [M+H]$^+$, found 342.21820; [α]$_D$+ 183.0° (c 3.99, MeOH).

Example 22

4-((trans)-2-((R)-4-cyclobutyl-3-methylpiperazine-1-carbonyl)cyclopropyl)benzamide, isomer 2

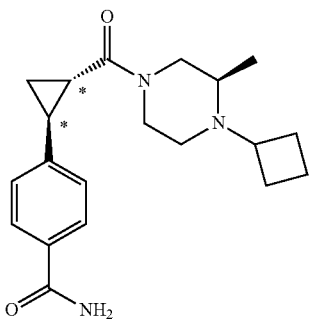 [SMILES: C[C@@H]1CN(C(=O)[C@H]2C[C@@H]2c2ccc(C(N)=O)cc2)CCN1C1CCC1]

Note: * designates single isomer of unknown absolute stereochemistry.

This isomer was isolated in accordance with the chiral separation described in Example 21 and treated as described therein. The product was analyzed on chiral SFC (UV detection) using isocratic method (mobile phase: 55% EtOH with 0.1% DMEA, supercritical CO$_2$) on ChiralPak AD, 4.6×250 mm, 20 μm particle size, giving an enantiomeric purity of 99%, R$_t$ 1.97 min (isomer 1) and 2.53 min (isomer 2). Isomer 2: $^1$H NMR (400 MHz, CD$_3$OD) δ ppm 0.95-1.06 (m, 3H) 1.33-1.44 (m, 1H) 1.51-1.63 (m, 1H) 1.63-1.76 (m, 2H) 1.91 (quin, J=10.60 Hz, 1H) 1.96-2.15 (m, 3H) 2.16-2.36 (m, 2H) 2.40-2.50 (m, 1H) 2.50-2.77 (m, 1H) 3.01-3.14 (m, 1H) 3.23 (dd, J=13.09, 7.23 Hz, 1H) 3.39-3.49 (m, 1H) 3.52-3.63 (m, 1H) 3.63-3.76 (m, 1H) 3.82 (ddd, J=12.79, 5.76, 2.93 Hz, 1H) 7.25 (d, J=8.20 Hz, 2H) 7.80 (d, J=8.59 Hz, 2H); HRMS m/z calcd for C$_{20}$H$_{28}$N$_3$O$_2$ 342.21760 [M+H]$^+$, found 342.21757; [α]$_D$-190.5° (c 3.25, MeOH).

Example 23

4-(trans-2-(4-cyclobutyl-2,2-dimethylpiperazine-1-carbonyl)cyclopropyl)benzamide, enantiomeric mixture

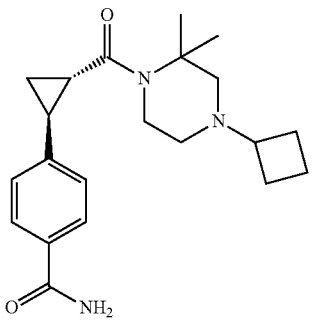 [SMILES: CC1(C)CN(C2CCC2)CCN1C(=O)[C@H]1C[C@@H]1c1ccc(C(N)=O)cc1]

Intermediate 24 (295 mg, 0.98 mmol) was dissolved in DCE (10 mL). TEA (1.366 mL, 9.80 mmol) was added, followed by cyclobutanone (137 mg, 1.96 mmol) and sodium triacetoxyborohydride (312 mg, 1.47 mmol). The reaction mixture was stirred for 5 days at rt, washed with sat NaHCO$_3$, dried over MgSO$_4$, filtered and concentrated under reduced pressure. The crude material was purified on preparative HPLC MS using the short high pH shallow gradient method (Mobile phase: 20-40% B; A: H$_2$O with 10 mM NH$_4$CO$_3$ and 0.375% NH$_4$OH v/v, B: CH$_3$CN, 10 mM run) on XBridge Prep C18 OBD, 30×50 mm, 5 μm, Waters reverse phase column, providing 101 mg title compound (29.0%) as a solid (enantiomeric mixture). $^1$H NMR (400 MHz, CD$_3$OD) δ ppm 1.30 (ddd, J=8.40, 6.05, 4.30 Hz, 1H) 1.38-1.47 (m, 6H) 1.49-1.57 (m, 1H) 1.66-1.79 (m, 2H) 1.90 (quin, J=9.57 Hz, 2H) 1.98-2.09 (m, 2H) 2.10-2.27 (m, 3H) 2.29-2.51 (m, 3H) 2.76 (br. s., 1H) 3.54-3.71 (m, 2H) 7.24 (d, J=8.59 Hz, 2H) 7.79 (d, J=8.59 Hz, 2H); HRMS m/z calcd for C$_{21}$H$_{30}$N$_3$O$_2$ 356.23325 [M+H]$^+$, found 356.23291.

Example 24

4-(trans-2-(4-cyclobutyl-3,3-dimethylpiperazine-1-carbonyl)cyclopropyl)benzamide, enantiomeric mixture

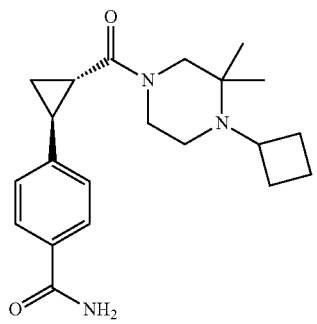 [SMILES: CC1(C)CN(C(=O)[C@H]2C[C@@H]2c2ccc(C(N)=O)cc2)CCN1C1CCC1]

Intermediate 14 (282 mg, 1.38 mmol) was dissolved in DMF (15 mL). DIPEA (1.201 mL, 6.88 mmol) was added, followed by HOBT (279 mg, 2.06 mmol), EDC (395 mg, 2.06 mmol) and Intermediate 2 (278 mg, 1.65 mmol). The reaction mixture was stirred at rt for 2 h and concentrated under reduced pressure. The residue was redissolved in DCM, washed with sat NaHCO$_3$, dried over MgSO$_4$, filtered and concentrated under reduced pressure to give 632 mg of crude as an orange oil. The crude material was purified on preparative HPLC UV using the long high pH shallow gradient method (Mobile phase: 20-40% B; A: H$_2$O with 10 mM NH$_4$CO$_3$ and 0.375% NH$_4$OH v/v, B: CH$_3$CN, 30 min run) on XBridge Prep C18 OBD, 50×250 mm, 10μ, Waters reverse phase column, providing 151 mg title compound (30.9%) as a solid (enantiomeric mixture). $^1$H NMR (400 MHz, CD$_3$OD) δ ppm 1.01 (s, 2H) 1.08 (s, 4H) 1.34-1.43 (m, 1H) 1.55-1.70 (m, 4H) 1.96-2.12 (m, 5H) 2.25-2.37 (m, 1H) 2.40-2.48 (m, 1H) 2.61 (br. s., 2H) 3.45 (br. s., 2H) 3.75 (br. s., 1H) 7.26 (dd, J=8.20, 5.08 Hz, 2H) 7.80 (dd, J=8.40, 2.93 Hz, 2H); HRMS m/z calcd for C$_{21}$H$_{30}$N$_3$O$_2$ 356.23325 [M+H]$^+$, found 356.23286.

Example 25

4-(trans-2-(4-cyclobutyl-3,3-dimethylpiperazine-1-carbonyl)cyclopropyl)benzamide, enantiomer 1

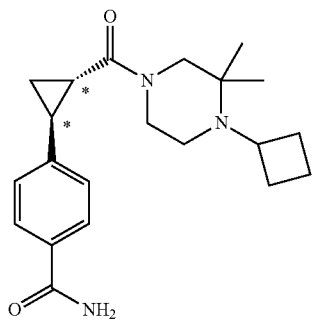 [SMILES: CC1(C)CN(C(=O)[C@H]2C[C@@H]2c2ccc(C(N)=O)cc2)CCN1C1CCC1]

Note: * designates single isomer of unknown absolute stereochemistry.

Example 24 (124 mg, 0.35 mmol) (enantiomeric mixture) was separated on a MettlerToledo Minigram Supercritical Fluid Chromatography instrument using the following conditions: ChiralPak AD-H, 10×250 mm, 5 μm particle size, 10.0 mL/min, mobile phase: 55% MeOH with 0.1% DMEA, supercritical CO$_2$, regulator set to 100 Bar, column temperature set to 35° C., UV 215 nm, providing 49.1 mg enantiomer 1 (79%) and 48.3 mg enantiomer 2 (78%) as solids. The product was analyzed on chiral SFC (UV detection) using isocratic method (mobile phase: 55% MeOH with 0.1% DMEA, supercritical CO$_2$) on ChiralPak AD-H, 10×250 mm, 5 μm particle size, giving an enantiomeric purity of 99%, R$_t$ 2.11 min (enantiomer 1) and 3.18 min (enantiomer 2). Enantiomer 1: $^1$H NMR (400 MHz, CD$_3$OD) δ ppm 0.97 (s, 2H) 1.05 (s, 4H) 1.34-1.42 (m, 1H) 1.55-1.68 (m, 3H) 1.93-2.11 (m, 4H) 2.24-2.37 (m, 1H) 2.39-2.47 (m, 1H) 2.47-2.66 (m, 2H) 3.32-3.47 (m, 3H) 3.48-3.58 (m, 0.5H) 3.63-3.81 (m, 1.5H) 7.26 (dd, J=8.20, 5.08 Hz, 2H) 7.80 (dd, J=8.40, 3.32 Hz, 2H); HRMS m/z calcd for C$_{21}$H$_{30}$N$_3$O$_2$ 356.2333 [M+H]$^+$, found 356.2332; [α]$_D$+193° (c 0.42, MeOH).

Example 26

4-(trans-2-(4-cyclobutyl-3,3-dimethylpiperazine-1-carbonyl)cyclopropyl)benzamide, enantiomer 2

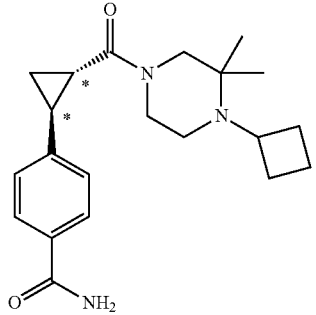 [SMILES: CC1(C)CN(C(=O)[C@H]2C[C@@H]2c2ccc(C(N)=O)cc2)CCN1C1CCC1]

Note: * designates single isomer of unknown absolute stereochemistry.

This isomer was isolated in accordance with the chiral separation described in Example 25 and treated as described therein. The product was analyzed on chiral SFC (UV detection) using isocratic method (mobile phase: 55% MeOH with 0.1% DMEA, supercritical $CO_2$) on ChiralPak AD-H, 10×250 mm, 5 μm particle size, giving an enantiomeric purity of 99%, $R_t$ 2.11 min (enantiomer 1) and 3.18 min (enantiomer 2). Enantiomer 2: $^1$H NMR (400 MHz, $CD_3OD$) δ ppm 0.97 (s, 2H) 1.05 (s, 4H) 1.38 (dddd, J=8.40, 6.15, 5.96, 4.49 Hz, 1H) 1.55-1.68 (m, 3H) 1.93-2.11 (m, 4H) 2.24-2.37 (m, 1H) 2.40-2.47 (m, 1H) 2.47-2.65 (m, 2H) 3.32-3.47 (m, 3H) 3.47-3.58 (m, 1H) 3.63-3.80 (m, 1H) 7.26 (dd, J=8.40, 5.27 Hz, 2H) 7.80 (dd, J=8.59, 3.52 Hz, 2H); HRMS m/z calcd for $C_{21}H_{30}N_3O_2$ 356.2333 [M+H]$^+$, found 356.2331; $[α]_D$ −195° (c 0.49, MeOH).

Example 27

3-(trans-2-((R)-4-cyclobutyl-2-methylpiperazine-1-carbonyl)cyclopropyl)benzamide, diastereomeric mixture

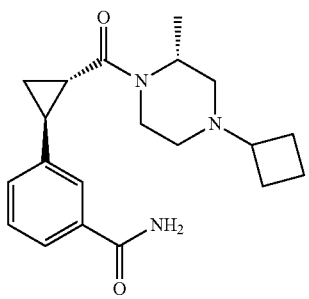 [SMILES: C[C@@H]1CN(C2CCC2)CCN1C(=O)[C@H]1C[C@@H]1c1cccc(C(N)=O)c1]

Intermediate 30 (101 mg, 0.35 mmol) was dissolved in DCE (3.5 mL). TEA (0.098 mL, 0.70 mmol) was added, followed by cyclobutanone (49.1 mg, 0.70 mmol) and sodium triacetoxyborohydride (111 mg, 0.53 mmol). The reaction mixture was stirred overnight, washed with sat. $NaHCO_3$, dried over $MgSO_4$, filtered and concentrated under reduced pressure. The crude material was purified on preparative HPLC MS using the short high pH shallow gradient method (Mobile phase: 20-40% B; A: $H_2O$ with 10 mM $NH_4CO_3$ and 0.375% $NH_4OH$ v/v, B: $CH_3CN$, 10 min run) on XBridge Prep C18 OBD, 30×50 mm, 5 μm, Waters reverse phase column, providing 73.7 mg title compound (61.7%) as a solid (diastereomeric mixture). $^1$H NMR (400 MHz, $CD_3OD$) δ ppm 1.28 (br. s., 4H) 1.58 (dt, J=9.08, 4.64 Hz, 1H) 1.64-2.11 (m, 8H) 2.27 (dt, J=8.69, 4.44 Hz, 1H) 2.44 (br. s., 1H) 2.62-2.78 (m, 2H) 2.85 (d, J=9.37 Hz, 1H) 2.97 (br. s., 1H) 4.04 (br. s., 0.5H) 4.29 (br. s., 0.5H) 4.49 (br. s., 0.5H) 4.67 (br. s., 0.5H) 7.33-7.44 (m, 2H) 7.63 (s, 1H) 7.70 (t, J=4.30 Hz, 1H); HRMS m/z calcd for $C_{20}H_{28}N_3O_2$ 342.21760 [M+H]$^+$, found 342.21788.

Example 28

3-((trans)-2-((R)-4-cyclobutyl-2-methylpiperazine-1-carbonyl)cyclopropyl)benzamide, isomer 1

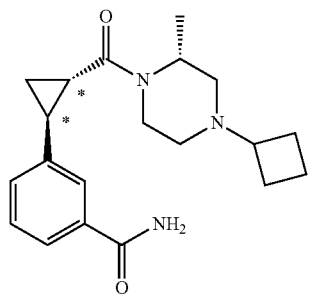 [SMILES: C[C@@H]1CN(C2CCC2)CCN1C(=O)[C@H]1C[C@@H]1c1cccc(C(N)=O)c1]

Note: * designates single isomer of unknown absolute stereochemistry.

Example 27 (50.9 mg, 0.15 mmol) (diastereomeric mixture) was separated on a MettlerToledo Minigram Supercritical Fluid Chromatography instrument using the following conditions: ChiralPak AD-H, 10×250 mm, 5 μm particle size, 10.0 mL/min, mobile phase: 40% MeOH with 0.1% DMEA, supercritical $CO_2$, regulator set to 100 Bar, column temperature set to 35° C., UV 215 nm, providing 23.9 mg isomer 1 (47.0%) and 23.2 mg isomer 2 (45.7%) as solids. The product was analyzed on chiral SFC (UV detection) using isocratic method (mobile phase: 40% iPrOH with 0.1% DMEA, supercritical $CO_2$) on ChiralPak AD, 4.6×250 mm, 20 μm particle size, giving an enantiomeric purity of 99%, $R_t$ 2.78 min (isomer 1) and 4.02 min (isomer 2). Isomer 1: $^1$H NMR (400 MHz, $CD_3OD$) δ ppm 1.27 (br. s., 1H) 1.39 (br. s., 3H) 1.53-1.64 (m, 1H) 1.64-2.14 (m, 8H) 2.27 (dd, J=8.20, 4.69 Hz, 1H) 2.36-2.52 (m, 1H) 2.62-2.79 (m, 2H) 2.85 (d, J=10.55 Hz, 1H) 2.90-3.06 (m, 0.5H) 3.34-3.48 (m, 0.5H) 4.06 (d, J=14.06 Hz, 0.5H) 4.32 (d, J=14.84 Hz, 0.5H) 4.41-4.48 (m, 0.5H) 4.57-4.75 (m, 0.5H) 7.38 (d, J=4.30 Hz, 2H) 7.63 (s, 1H) 7.70 (t, J=3.52 Hz, 1H); HRMS m/z calcd for $C_{20}H_{28}N_3O_2$ 342.21760 [M+H]$^+$, found 342.21776; $[α]_D$+ 127.2° (c 0.79, MeOH).

Example 29

3-((trans)-2-((R)-4-cyclobutyl-2-methylpiperazine-1-carbonyl)cyclopropyl)benzamide, isomer 2

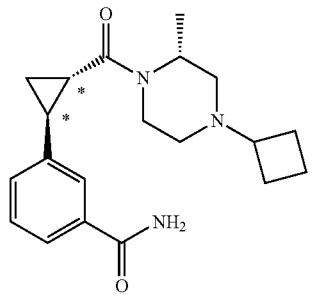 [SMILES: C[C@@H]1CN(C2CCC2)CCN1C(=O)[C@H]1C[C@@H]1c1cccc(C(N)=O)c1]

Note: * designates single isomer of unknown absolute stereochemistry.

This isomer was isolated in accordance with the chiral separation described in Example 28 and treated as described therein. The product was analyzed on chiral SFC (UV detection) using isocratic method (mobile phase: 40% iPrOH with 0.1% DMEA, supercritical $CO_2$) on ChiralPak AD, 4.6×250 mm, 20 μm particle size, giving an enantiomeric purity of 99%, $R_t$ 2.78 min (isomer 1) and 4.02 min (isomer 2). Isomer 2: $^1$H NMR (400 MHz, $CD_3OD$) δ ppm 1.28 (d, J=3.12 Hz, 3H) 1.38 (br. s., 1H) 1.49-1.65 (m, 1H) 1.65-2.16 (m, 8H) 2.27 (br. s., 1H) 2.43 (br. s., 1H) 2.62-2.78 (m, 2H) 2.84 (br. s., 1H) 2.91-3.03 (m, 0.5H) 3.37-3.49 (m, 0.5H) 4.02 (d, J=13.28 Hz, 0.5H) 4.29 (d, J=12.50 Hz, 0.5H) 4.47 (br. s., 0.5H) 4.68 (br. s., 0.5H) 7.38 (d, J=4.30 Hz, 2H) 7.63 (s, 1H) 7.70 (ddd, J=4.98, 3.61, 1.56 Hz, 1H); HRMS m/z calcd for $C_{20}H_{28}N_3O_2$ 342.21760 [M+H]$^+$, found 342.21766; $[α]_D$−191.9° (c 0.64, MeOH).

Example 30

3-(trans-2-((S)-4-cyclobutyl-2-methylpiperazine-1-carbonyl)cyclopropyl)benzamide, diastereomeric mixture

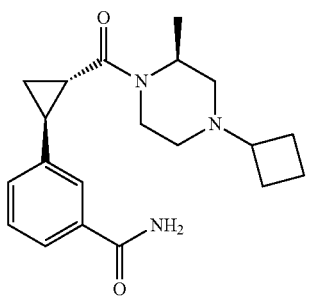 [SMILES: C[C@H]1CN(C2CCC2)CCN1C(=O)[C@H]1C[C@@H]1c1cccc(C(N)=O)c1]

Intermediate 31 (98 mg, 0.34 mmol) was dissolved in DCE (3.5 mL). TEA (0.095 mL, 0.68 mmol) was added, followed by cyclobutanone (47.7 mg, 0.68 mmol) and sodium triacetoxyborohydride (108 mg, 0.51 mmol). The reaction mixture was stirred overnight, washed with sat. $NaHCO_3$, dried over $MgSO_4$, filtered and concentrated under reduced pressure to give 78.2 mg of crude as an orange oil. The crude material was purified on preparative HPLC MS using the short high pH shallow gradient method (Mobile phase: 20-40% B; A: $H_2O$ with 10 mM $NH_4CO_3$ and 0.375% $NH_4OH$ v/v, B: $CH_3CN$, 10 min run) on XBridge Prep C18 OBD, 30×50 mm, 5 μm, Waters reverse phase column, providing 63.6 mg title compound (54.8%) as a solid (diastereomeric mixture). $^1$H NMR (400 MHz, $CD_3OD$) δ ppm 1.27 (br. s., 4H) 1.58 (ddd, J=9.18, 4.88, 4.69 Hz, 1H) 1.65-2.12 (m, 8H) 2.18-2.34 (m, 1H) 2.45 (br. s., 1H) 2.61-2.78 (m, 2H) 2.85 (d, J=12.89 Hz, 1H) 2.97 (t, J=12.89 Hz, 1H) 4.04 (br. s., 0.5H) 4.30 (br. s., 0.5H) 4.46 (br. s., 0.5H) 4.67 (br. s., 0.5H) 7.30-7.45 (m, 2H) 7.63 (s, 1H) 7.66-7.76 (m, 1H); HRMS m/z calcd for $C_{20}H_{28}N_3O_2$ 342.21760 [M+H]$^+$, found 342.21769.

Example 31

3-((trans)-2-((S)-4-cyclobutyl-2-methylpiperazine-1-carbonyl)cyclopropyl)benzamide, isomer 1

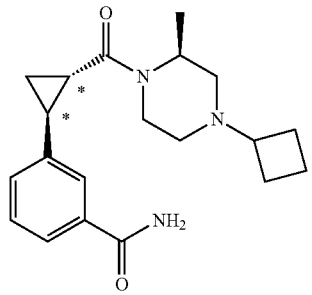 [SMILES: C[C@H]1CN(C2CCC2)CCN1C(=O)[C@H]1C[C@@H]1c1cccc(C(N)=O)c1]

Note: * designates single isomer of unknown absolute stereochemistry.

Example 30 (39.9 mg, 0.12 mmol) (diastereomeric mixture) was separated on a MettlerToledo Minigram Supercritical Fluid Chromatography instrument using the following conditions: ChiralPak AS-H, 10×250 mm, 5 μm particle size, 10.0 mL/min, mobile phase: 45% iPrOH with 0.1% DMEA, supercritical $CO_2$, regulator set to 100 Bar, column temperature set to 35° C., UV 215 nm, providing 17.0 mg isomer 1 (42.7%) and 14.1 mg isomer 2 (35.3%) as solids. The product was analyzed on chiral SFC (UV detection) using isocratic method (mobile phase: 45% iPrOH with 0.1% DMEA, supercritical $CO_2$) on ChiralPak AS-H, 10×250 mm, 5 μm particle size, giving an enantiomeric purity of 99%, $R_t$ 3.55 min (isomer 1) and 5.58 min (isomer 2). Isomer 1: $^1$H NMR (400 MHz, $CD_3OD$) δ ppm 1.28 (d, J=2.34 Hz, 3H) 1.38 (br. s., 1H) 1.65 (br. s., 1H) 1.66-2.12 (m, 8H) 2.27 (br. s., 1H) 2.43 (br. s., 1H) 2.63-2.78 (m, 2H) 2.84 (br. s., 1H) 2.91-3.10 (m, 0.5H) 3.37-3.53 (m, 0.5H) 3.95-4.09 (m, 0.5H) 4.19-4.35 (m, 0.5H) 4.47 (br. s., 0.5H) 4.68 (br. s., 0.5H) 7.38 (d, J=4.30 Hz, 2H) 7.63 (br. s., 1H) 7.66-7.74 (m, 1H); HRMS m/z calcd for $C_{20}H_{28}N_3O_2$ 342.21760 [M+H]$^+$, found 342.21726; $[α]_D$+269.1° (c 0.21, MeOH).

Example 32

3-((trans)-2-((S)-4-cyclobutyl-2-methylpiperazine-1-carbonyl)cyclopropyl)benzamide, isomer 2

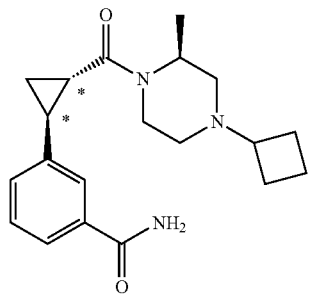 [SMILES: C[C@H]1CN(C2CCC2)CCN1C(=O)[C@H]1C[C@@H]1c1cccc(C(N)=O)c1]

Note: * designates single isomer of unknown absolute stereochemistry.

This isomer was isolated in accordance with the chiral separation described in Example 31 and treated as described therein. The product was analyzed on chiral SFC (UV detection) using isocratic method (mobile phase: 45% iPrOH with 0.1% DMEA, supercritical $CO_2$) on ChiralPak AS-H, 10×250 mm, 5 μm particle size, giving an enantiomeric purity of 99%, $R_t$ 3.55 min (isomer 1) and 5.58 min (isomer 2). Isomer 2: $^1$H NMR (400 MHz, $CD_3OD$) δ ppm 1.27 (br. s., 1H) 1.39 (br. s., 3H) 1.50-1.64 (m, 1H) 1.64-2.15 (m, 8H) 2.18-2.35 (m, 1H) 2.44 (br. s., 1H) 2.61-2.77 (m, 2H) 2.85 (d, J=11.33 Hz, 1H) 2.90-3.06 (m, 0.5H) 3.35-3.47 (m, 0.5H) 4.06 (d, J=12.89 Hz, 0.5H) 4.32 (d, J=12.50 Hz, 0.5H) 4.36-4.51 (m, 0.5H) 4.66 (br. s., 0.5H) 7.38 (d, J=4.69 Hz, 2H) 7.63 (s, 1H) 7.68-7.77 (m, 1H); HRMS m/z calcd for $C_{20}H_{28}N_3O_2$ 342.21760 [M+H]$^+$, found 342.21762; [α]$_D$ –114.9° (c 0.56, MeOH).

Example 33

3-(trans-2-((S)-4-cyclobutyl-3-methylpiperazine-1-carbonyl)cyclopropyl)benzamide, diastereomeric mixture

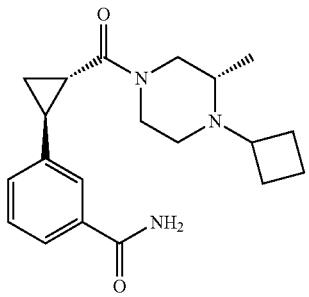 [SMILES: C[C@H]1CN(C(=O)[C@H]2C[C@@H]2c2cccc(C(N)=O)c2)CCN1C1CCC1]

Oxalyl chloride (0.256 mL, 2.92 mmol) was slowly added to a solution of intermediate 27 (200 mg, 0.97 mmol) in DCM (3.0 mL) at 0° C. under a nitrogen atmosphere. The solution was stirred for 3 h while warming to rt. The solvent was concentrated under reduced pressure and the residue was redissolved in DCM (1.0 mL). The resulting solution was added dropwise to a solution of intermediate 8 and DIPEA (0.851 mL, 4.87 mmol) in DCM (3.0 mL) at 0° C. under a nitrogen atmosphere. The reaction mixture was stirred overnight and the solvent was evaporated to give the crude product as a dark orange gummy solid. The crude material was purified on preparative HPLC UV using the long high pH shallow gradient method (Mobile phase: 30-50% B; A: $H_2O$ with 10 mM $NH_4CO_3$ and 0.375% $NH_4OH$ v/v, B: $CH_3CN$, 25 min run) on XBridge Prep C18 OBD, 30×150 mm, 5μ, Waters reverse phase column, providing 69.2 mg title compound (20.79%) as a solid (diastereomeric mixture). $^1$H NMR (400 MHz, $CD_3OD$) δ ppm 0.91-1.07 (m, 3H) 1.33-1.45 (m, 1H) 1.50-1.63 (m, 1H) 1.63-1.76 (m, 2H) 1.85-2.15 (m, 4H) 2.17-2.35 (m, 2H) 2.37-2.51 (m, 1H) 2.52-2.80 (m, 2H) 3.01-3.17 (m, 1H) 3.19-3.53 (m, 1H) 3.53-3.90 (m, 3H) 7.33-7.44 (m, 2H) 7.63 (s, 1H) 7.66-7.76 (m, 1H); HRMS m/z calcd for $C_{20}H_{28}N_3O_2$ 342.21760 [M+H]$^+$, found 342.21697.

Example 34

3-(trans-2-((R)-4-cyclobutyl-3-methylpiperazine-1-carbonyl)cyclopropyl)benzamide, diastereomeric mixture

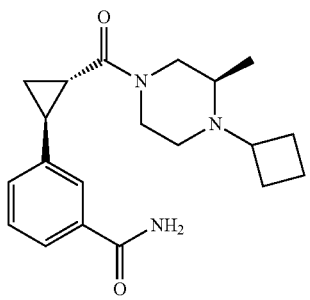 [SMILES: C[C@@H]1CN(C(=O)[C@H]2C[C@@H]2c2cccc(C(N)=O)c2)CCN1C1CCC1]

Oxalyl chloride (0.256 mL, 2.92 mmol) was slowly added to a solution of intermediate 27 (200 mg, 0.97 mmol) in DCM (3.0 mL) at 0° C. under a nitrogen atmosphere. The solution was stirred for 3 h while warming to rt. The solvent was concentrated under reduced pressure and the residue was redissolved in DCM (1.0 mL). The resulting solution was added dropwise to a solution of intermediate 5 (221 mg, 0.97 mmol) and DIPEA (0.851 mL, 4.87 mmol) in DCM (3.0 mL) at 0° C. under a nitrogen atmosphere. The reaction mixture was stirred overnight and the solvent was evaporated to give the crude product as a dark yellow gummy solid. The crude material was purified on preparative HPLC UV using the long high pH shallow gradient method (Mobile phase: 30-50% B; A: $H_2O$ with 10 mM $NH_4CO_3$ and 0.375% $NH_4OH$ v/v, B: $CH_3CN$, 25 min run) on XBridge Prep C18 OBD, 30×150 mm, 5μ, Waters reverse phase column, providing 74.5 mg title compound (22.39%) as a solid (diastereomeric mixture). $^1$H NMR (400 MHz, $CD_3OD$) δ ppm 0.90-1.08 (m, 3H) 1.33-1.45 (m, 1H) 1.50-1.63 (m, 1H) 1.63-1.77 (m, 2H) 1.85-2.15 (m, 4H) 2.17-2.35 (m, 2H) 2.38-2.51 (m, 1H) 2.51-2.80 (m, 2H) 3.02-3.16 (m, 1H) 3.20-3.54 (m, 1H) 3.53-3.91 (m, 3H) 7.33-7.42 (m, 2H) 7.63 (s, 1H) 7.66-7.74 (m, 1H); HRMS m/z calcd for $C_{20}H_{28}N_3O_2$ 342.21760 [M+H]$^+$, found 342.21964.

Example 35

First Method

4-{(1S,2S)-2-[((R)-4-Cyclobutyl-2-methylpiperazin-1-yl)carbonyl]-cyclopropyl}-benzamide

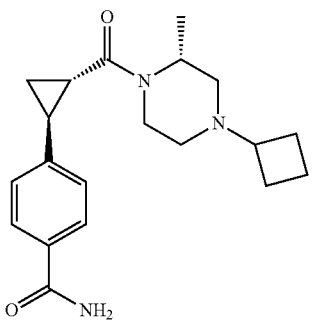 [SMILES: C[C@@H]1CN(C2CCC2)CCN1C(=O)[C@H]1C[C@@H]1c1ccc(C(N)=O)cc1]

Intermediate 37 (389 g, 1.90 moles) was mixed in 2-MeTHF (6.7 L) at $t_{jacket}$=25° C. 1,1'-Carbonyldiimidazole (412 g, 2.09 moles, 82.1% w/w) was added in 1 portion. The reaction slurry was heated to $t_{jacket}$=55° C. The gas evolution decreased after approximately 1 h. The reaction slurry was heated to $t_{jacket}$=85° C. for 3 h and then cooled to $t_{jacket}$=50° C. Intermediate 32 (490 g, 2.08 moles, 96.3% w/w) and TEA (290 mL, 2.09 moles) were added to the reaction slurry. 2-MeTHF (2 L) was used for rinsing. The reaction slurry was heated at $t_{jacket}$=70° C. for 4 h. Analyzing a sample on HPLC indicated full conversion at this point. The reaction slurry was cooled to $t_{jacket}$=20° C. 1M $Na_2CO_3$ in brine (2 L) was added and the temperature was adjusted to $t_{jacket}$=40° C. The aq. phase was separated off and the organic phase washed with brine (2 L). The organic phase was extracted with 5% $H_3PO_4$ in $H_2O$ (1.5 L×4) at $t_{jacket}$=20° C. The combined aq. phases were washed with DCM (1 L). Very slow phase separation occurred. The combined aq. phases were basified to pH>11 with 5M NaOH and extracted with DCM (1.2 L×2). The combined organic phases were concentrated under vacuum to dryness. The residual oil was dissolved in acetonitrile (1.2 L) at $t_{jacket}$=50° C. Seed was added and the solution was stirred for 30 min. at $t_{jacket}$=40° C. The mixture was cooled to $t_{jacket}$=5° C. over 6 h and the product was filtered off. Drying under vacuum at 40° C. gave 372 g Example 35 (1.04 moles, 100% w/w) as a first crop. The mother liquid was recrystallized from acetonitrile and a second crop could be isolated of Example 35 (77 g, 0.21 moles, 98.7% w/w). Example 35 was isolated in a total yield of 66%. Example 35 corresponds to Example 8 (isomer 1). $^1$H-NMR (DMSO-d$_6$): δ 7.91 (br s, 1H), 7.78 (d, J=8.4 Hz, 2H), 7.30 (br s, 1H), 7.25 (d, J=8.0 Hz, 2H), 4.54 and 4.36 (br s, 1H), 4.17 and 4.01 (d, J=12.2 Hz, 1H), 3.20 and 2.80 (t, J=11.9 Hz, 1H), 2.74 (d, J=11.4 Hz, 1H), 2.67-2.55 (m, 2H), 2.33 (br s, 2H), 1.99-1.88 (m, 2H), 1.88-1.53 (m, 6H), 1.48-1.37 (m, 1H), 1.27 (br s, 3H), 1.12 (br s, 1H); LC-MS (ES): m/z 342 (M+1). R$_t$ 1.68 min with the analytical method (mobile phase: 5-90% B; A: $H_2O$ with 0.1% formic acid, B: $CH_3CN$, 8.6 min run) on Xbridge C18, 3.0×50 mm, 2.5 μm particle size.

Example 35

Second Method

4-{(1S,2S)-2-[((R)-4-Cyclobutyl-2-methylpiperazin-1-yl)carbonyl]-cyclopropyl}-benzamide

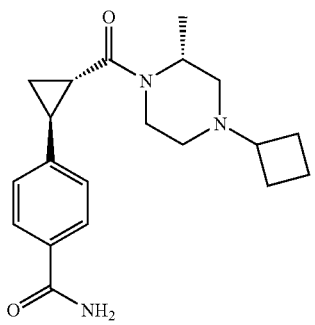

$N_2$ was bubbled into Intermediate 39 (6.09 g, 18.83 mmol) in EtOH (125 mL) and $H_2O$ (30 mL). To this was added Hydrido(dimethylphosphinous acid-kP)[hydrogen bis(dimethylphosphnito-kP]platinum (II) (0.050 g, 0.12 mmol). The reaction was heated at reflux for 20 h. The reaction was heated for a further 24 h, concentrated to dryness and partitioned between EtOAc and $H_2O$. The aq. phase was extracted 3× with EtOAc, the combined organic layers were washed with brine, dried over $Na_2SO_4$, filtered and concentrated. The crude material was purified by flash chromatography on silica gel, eluting with a gradient of $CH_2Cl_2$ and MeOH, 2-10% with a plateau at 4% until elution of visible dark band followed by a second purification with a gradient of acetone/heptane 30-100% to afford 3.65 g Example 35 (56.8% yield) as a solid. $^1$H NMR (400 MHz, $CD_3OD$) δ ppm 1.24 (br. s., 1H) 1.36 (br. s., 3H) 1.52-1.60 (m, 1H) 1.63-1.74 (m, 3H) 1.74-1.84 (m, 1H) 1.84-1.95 (m, 2H) 1.95-2.05 (m, 2H) 2.24 (br. s., 1H) 2.40 (br. s., 1H) 2.60-2.72 (m, 2H) 2.82 (d, J=12.50 Hz, 1H) 2.94 and 3.36 (t, J=12.11 Hz, 1H) 4.01 and 4.28 (d, J=13.28 Hz, 1H) 4.35 and 4.62 (br. s., 1H) 7.22 (d, J=8.20 Hz, 2H) 7.77 (d, J=8.59 Hz, 2H). The product was analyzed on analytical HPLC MS using the Zorbax gradient method (mobile phase: 5-95% B; A: $H_2O$ with 0.05% TFA, B: $CH_3CN$, 4.5 min run) on Zorbax SB C18, 4.6×30 mm, 1.8 μm particle size. MS m/z 342.3 [M+H]$^+$ (ESI), R$_t$=0.584 min. The product was analyzed on chiral SFC (UV detection) using isocratic method (mobile phase: 55% EtOH with 0.1% DMEA, supercritical $CO_2$) on ChiralPak AD-H, 10×250 mm, 5 μm particle size, giving an enantiomeric purity of >99%, R$_t$ 1.98 min. Example 35 corresponds to Example 8 (isomer 1). HRMS m/z calcd for $C_{20}H_{27}N_3O_2$ 342.2176 [M+H]$^+$, found 342.2176.

Example 35

Crystalline Form I

4-{(1S,2S)-2-[((R)-4-Cyclobutyl-2-methylpiperazin-1-yl)carbonyl]-cyclopropyl}-benzamide, Crystalline Form I

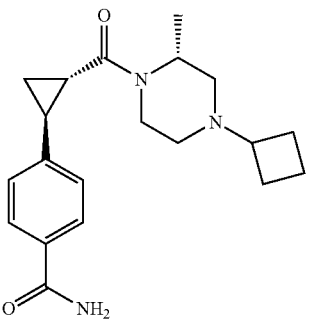 [SMILES: C[C@@H]1CN(C2CCC2)CCN1C(=O)[C@H]1C[C@@H]1c1ccc(C(N)=O)cc1]

In a first means of preparing Crystalline Form I, 20 mg of an amorphous form of 4-{(1S,2S)-2-[((R)-4-Cyclobutyl-2-methylpiperazin-1-yl)carbonyl]-cyclopropyl}-benzamide was added to a vessel. To the vessel, 100 μl of EtOAc was added to obtain a suspension. The resulting slurry was stirred at ambient temperature for 3 days. Solid material was then isolated and dried in air.

In a second means of preparing Crystalline Form I, 20 mg of an amorphous form of 4-{(1S,2S)-2-[((R)-4-Cyclobutyl-2-methylpiperazin-1-yl)carbonyl]-cyclopropyl}-benzamide was added to a vessel. To the vessel, 100 μl of acetonitrile was added to obtain a suspension. The resulting slurry was stirred at ambient temperature for 3 days. Solid material was then isolated and dried in air.

The solid material obtained via at least one of the processes set forth above was analyzed by XRPD. Selected peaks are provided in Table 1. A representative XRPD pattern is shown in FIG. 1. The XRPD pattern confirmed the solid material to be Crystalline Form I.

TABLE 2

| Selected XRPD Peaks of Crystalline Form I | | |
|---|---|---|
| Peak | °2θ | Relative Intensity (%) |
| 1 | 4.6 | 51.7 |
| 2 | 7.6 | 43.2 |
| 3 | 11.8 | 30.8 |
| 4 | 14.1 | 20.9 |
| 5 | 15.3 | 48.7 |
| 6 | 15.5 | 100.0 |
| 7 | 15.9 | 36.9 |
| 8 | 17.4 | 76.8 |
| 9 | 18.9 | 50.7 |
| 10 | 22.2 | 33.8 |

Intermediates

Intermediate 1 tert-butyl 4-cyclobutyl-3,3-dimethylpiperazine-1-carboxylate

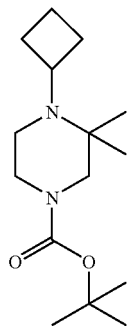 [SMILES: CC(C)(C)OC(=O)N1CCN(C2CCC2)C(C)(C)C1]

Tert-butyl 3,3-dimethylpiperazine-1-carboxylate (413 mg, 1.65 mmol) was dissolved in DCE (15 mL). TEA (1.148 mL, 8.23 mmol) was added, followed by cyclobutanone (231 mg, 3.29 mmol) and sodium triacetoxyborohydride (524 mg, 2.47 mmol). The reaction mixture was stirred for 5 h and a few drops of acetic acid were added. The reaction mixture was heated at 40° C. for 4 days, cooled to rt, washed with sat NaHCO$_3$, dried over MgSO$_4$, filtered and concentrated under reduced pressure to give a dark yellow oil. The crude title compound was used in the next step without further purification.

Intermediate 2

1-cyclobutyl-2,2-dimethylpiperazine

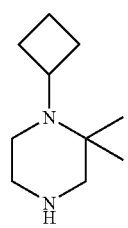

Intermediate 1 (0.443 g, 1.65 mmol) was dissolved in DCM (10 mL) and TFA (5.00 mL) was added. The reaction mixture was stirred for 1.5 h, then was concentrated under reduced pressure and dried under vacuum. The crude title compound was used in the next step without purification.

Intermediate 3

(R)-tert-butyl 3-methylpiperazine-1-carboxylate

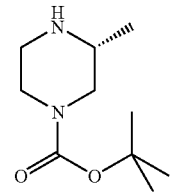

(R)-2-methylpiperazine (5.025 g, 50.2 mmol) was dissolved in DCM (100 mL). A solution of boc anhydride (5.47 g, 25.1 mmol) in DCM (50 mL) was added dropwise at 0° C. The reaction mixture was stirred at rt for 1 h. The solution was filtered and concentrated under reduced pressure. Water (100 mL) was added to the residue, which was filtered again. The filtrate was saturated with K$_2$CO$_3$ and extracted with Et$_2$O (3×150 mL). The combined organic layers were dried over anhydrous Na$_2$SO$_4$, filtered and concentrated under reduced pressure to provide 5.04 g title compound (50%) as a solid. $^1$H NMR (300 MHz, CDCl$_3$) δ ppm 1.03 (d, J=6.3 Hz, 3H) 1.45 (s, 9H) 1.56 (s, 1H) 2.30-2.46 (m, 1H) 2.65-2.72 (m, 1H) 2.74-2.76 (m, 2H) 2.93-2.95 (m, 1H) 3.93 (br s, 2H).

Intermediate 4

(R)-tert-butyl 4-cyclobutyl-3-methylpiperazine-1-carboxylate

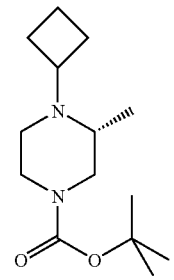 [SMILES: C[C@@H]1CN(C(=O)OC(C)(C)C)CCN1C1CCC1]

Intermediate 3 (2.63 g, 13.1 mmol) was dissolved in DCE (60 mL). Cyclobutanone (1.38 g, 19.7 mmol) and acetic acid (0.75 mL, 13.1 mmol) were added and the mixture stirred at rt for 30 min. NaBH(OAc)$_3$ (4.18 g, 19.7 mmol) was added portionwise and the mixture was stirred at rt overnight. Sat. Na$_2$CO$_3$ (50 mL) was added and the aq. layer was extracted with DCM (3×75 mL). The combined organic phases were dried over Na$_2$SO$_4$, filtered and concentrated under reduced pressure to provide 2.58 g title compound (77%) as an oil. $^1$H NMR (300 MHz, CDCl$_3$) δ ppm 0.97 (d, J=6.4 Hz, 3H) 1.45 (s, 9H) 1.61-1.70 (m, 2H) 1.81-1.91 (m, 1H) 1.93-2.00 (m, 2H) 2.03-2.14 (m, 2H) 2.41-2.51 (m, 1H) 2.58-2.65 (m, 1H) 2.94-3.05 (m, 1H) 3.06-3.16 (m, 1H) 3.29-3.58 (m, 3H).

Intermediate 5

(R)-1-cyclobutyl-2-methylpiperazine

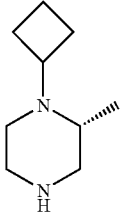

Intermediate 4 (2.58 g, 10.2 mmol) was dissolved in MeOH (30 mL). 4 M HCl in dioxane (10 mL) was added and the mixture was stirred at rt overnight. Volatiles were evaporated and the residue dissolved with a small quantity of MeOH. The solution was added dropwise to a large quantity of Et$_2$O with vigorous stirring. The precipitate was filtered and dried under reduced pressure to provide 2.01 g title compound (87%) as the hydrochloride salt. $^1$H NMR (300 MHz, CD$_3$OD) δ ppm 1.48 (d, J=6.7 Hz, 3H) 1.80-1.97 (m, 2H) 2.31-2.46 (m, 3H) 2.58-2.77 (m, 1H) 3.15-3.28 (m, 1H) 3.38-3.50 (m, 1H) 3.54-3.81 (m, 5H) 4.00 (q, J=8.3, 16.6 Hz, 1H); MS m/z 155.37 [M+H]$^+$ (ES+); [α]$_D$ –12.95° (c 2.95, MeOH).

Intermediate 6

(S)-tert-butyl 3-methylpiperazine-1-carboxylate

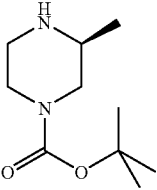

(S)-2-methylpiperazine (5.00 g, 49.9 mmol) was dissolved in DCM (150 mL). A solution of boc anhydride (5.47 g, 25.0 mmol) in DCM (50 mL) was added dropwise at 0° C. The reaction mixture was stirred at rt for 2 h. The solution was filtered and concentrated under reduced pressure. Water (100 mL) was added to the residue and it was filtered again. The filtrate was saturated with K$_2$CO$_3$ and extracted with Et$_2$O (3×150 mL). The combined organic layers were dried over anhydrous Na$_2$SO$_4$, filtered and concentrated under reduced pressure to provide 4.92 g title compound (49%) as a solid. $^1$H NMR (300 MHz, CDCl$_3$) δ ppm 1.03 (d, J=6.3 Hz, 3H) 1.45 (s, 9H) 1.53 (br. s, 1H) 2.38 (t, J=11.8 Hz, 1H) 2.65-2.72 (m, 1H) 2.74-2.76 (m, 2H) 2.92-2.95 (m, 1H) 3.92 (br. s, 2H).

Intermediate 7

(S)-tert-butyl 4-cyclobutyl-3-methylpiperazine-1-carboxylate

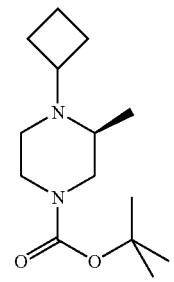 [SMILES: C[C@H]1CN(C(=O)OC(C)(C)C)CCN1C1CCC1]

Intermediate 6 (3.00 g, 15.0 mmol) was dissolved in DCE (65 mL). Cyclobutanone (1.58 g, 22.5 mmol) and acetic acid (0.86 mL, 15.0 mmol) were added and the mixture stirred at rt for 30 min. NaBH(OAc)$_3$ (4.76 g, 22.5 mmol) was added portionwise and the mixture was stirred at rt overnight. Sat. Na$_2$CO$_3$ (50 mL) was added and the aq. layer was extracted with DCM (3×75 mL). The combined organic phases were dried over Na$_2$SO$_4$, filtered and concentrated under reduced pressure to provide 3.45 g title compound (90%) as an oil. $^1$H NMR (300 MHz, CDCl$_3$) δ ppm 1.00 (d, J=6.5 Hz, 3H) 1.41 (s, 9H) 1.54-1.73 (m, 2H) 1.89-1.96 (m, 1H) 2.00-2.14 (m, 3H) 2.26 (br. s, 1H) 2.65 (br. s, 2H) 2.99-3.10 (m, 1H) 3.20 (br. s, 1H) 3.46 (br. s, 3H).

Intermediate 8

(S)-1-cyclobutyl-2-methylpiperazine

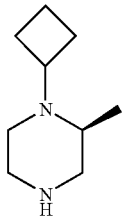

Intermediate 7 (3.45 g, 13.6 mmol) was dissolved in MeOH (40 mL). 4 M HCl in dioxane (10 mL) was added and the mixture was stirred at rt overnight. Volatiles were evaporated under reduced pressure and the residue dissolved with a small quantity of MeOH. The solution was added dropwise to a large quantity of Et$_2$O with vigorous stirring. The precipitate was filtered and dried under reduced pressure to provide 2.32 g title compound (75%) as the hydrochloride salt. $^1$H NMR (300 MHz, CD$_3$OD) δ ppm 1.46-1.50 (m, 3H) 1.81-1.97 (m, 2H) 2.35-2.46 (m, 3H) 2.58-2.79 (m, 1H) 3.15-3.28

(m, 1H) 3.39-3.51 (m, 1H) 3.54-3.82 (m, 5H) 4.01 (m, 1H); MS m/z 155.42 [M+H]+ (ES+); [α]$_D$+23.43° (c 4.0, MeOH).

Intermediate 9

(E)-tert-butyl 3-(4-cyanophenyl)acrylate

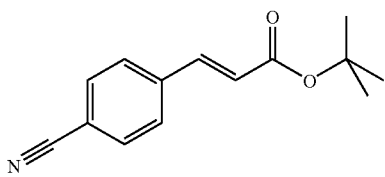 [SMILES: CC(C)(C)OC(=O)/C=C/c1ccc(C#N)cc1]

A flame dried three-neck round-bottom flask equipped with a magnetic stirring bar, a thermometer, an addition funnel and a nitrogen inlet was charged with NaH (3.96 g, 94.7 mmol) and anhydrous THF (120 mL). Tert-butyl diethylphosphonoacetate (23.2 mL, 94.7 mmol) dissolved in anhydrous THF (20 mL) was added dropwise via the addition funnel over a period of 30 min. After the completion of addition, the reaction mixture was stirred at rt for another 30 min. A solution of 4-cyanobenzaldehyde (11.3 g, 86.1 mmol) dissolved in anhydrous THF (20 mL) was added to the reaction mixture dropwise via the addition funnel over a period of 30 min. After the end of the addition, the reaction mixture was stirred at rt for 1 h, then diluted with MTBE (200 mL) and sat. NH$_4$Cl (150 mL). The organic layer was separated, washed with 25 mL of water and 25 mL of sat. NH$_4$Cl, dried over MgSO$_4$, filtered and evaporated to dryness to give 20.0 g title compound as a solid (100%). $^1$H NMR (400 MHz, CDCl$_3$) δ ppm 1.56 (s, 9H) 6.47 (d, J=16 Hz, 1H) 7.58 (d, J=16 Hz, 1H) 7.61 (d, J=8 Hz, 2H) 7.68 (d, J=8 Hz, 2H).

Intermediate 10 trans-tert-butyl 2-(4-cyanophenyl)cyclopropanecarboxylate

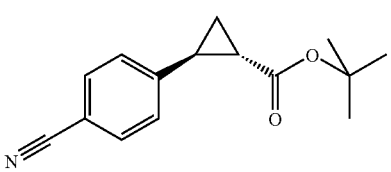 [SMILES: CC(C)(C)OC(=O)[C@H]1C[C@@H]1c1ccc(C#N)cc1]

Trimethylsulfoxonium iodide (37.9 g, 172.4 mmol) was dissolved in DMSO (450 mL) under nitrogen. Sodium tert-butoxide (16.5 g, 172.4 mmol) was added and the resultant mixture was stirred at rt for 2 h. Intermediate 9 (20 g, 86.2 mmol) was added and the reaction mixture was stirred at rt for 16 h. The reaction mixture was diluted by sequential addition of MTBE (500 mL) and brine (300 mL). The organic layer was separated, dried over MgSO$_4$, filtered and evaporated to dryness. The crude product was purified by flash chromatography (silica, heptane/EtOAc 95:5 to 90:10), giving 11.6 g title compound (54%) as a solid. $^1$H NMR (400 MHz, CDCl$_3$) δ ppm 1.29-1.23 (m, 1H) 1.49 (s, 9H) 1.57-1.69 (m, 1H) 1.83-1.96 (m, 1H) 2.40-2.53 (m, 1H) 7.18 (d, J=8 Hz, 2H) 7.57 (d, J=8 Hz, 2H).

Intermediate 11 trans-2-(4-bromophenyl)cyclopropyl)methanol

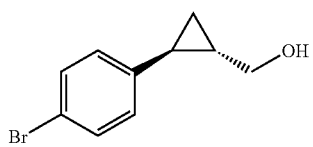 [SMILES: OC[C@H]1C[C@@H]1c1ccc(Br)cc1]

A solution of diethyl zinc (1.1 M, 695 mL, 765 mmol) in hexanes was added to a flame-dried 3-necked round bottom flask containing 450 mL of DCM under nitrogen. The resulting solution was cooled to 0-5° C. TFA (59 mL, 765 mmol) was added slowly to the cooled diethylzinc solution. After the completion of addition, the resulting mixture was stirred for 20 min. A solution of CH$_2$I$_2$ (62 mL, 765 mmol) in 50 mL of DCM was added to the mixture. After an additional 20 min of stirring, a solution of 3-(4-bromophenyl)prop-2-en-1-ol (81.6 g, 382.9 mmol) in 450 mL of DCM was added. After completing addition, the reaction mixture was warmed to rt and stirred for 2 h. Excess reagent was quenched by slow addition of 500 mL of 1 M HCl. The top aq. layer was separated and extracted with 200 mL of DCM. The combined organic extracts were washed with 500 mL of a mixture of sat. NH$_4$Cl and NH$_4$OH (9:1 v/v), dried over MgSO$_4$, filtered and concentrated under reduced pressure. The crude was purified by flash column chromatography (silica, heptane/EtOAc 10:1), giving 76.1 g title compound as a solid (87.5%). $^1$H NMR (400 MHz, CDCl$_3$) δ ppm 0.90-1.00 (m, 2H) 1.36-1.48 (m, 1H) 1.75-1.85 (m, 1H) 3.62 (t, J=6 Hz, 2H) 6.95 (d, J=8.5 Hz, 2H) 7.38 (d, J=8.5 Hz, 2H).

Intermediate 12 trans-4-(2-(hydroxymethyl)cyclopropyl)benzonitrile

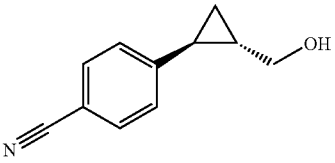 [SMILES: N#Cc1ccc([C@H]2C[C@@H]2CO)cc1]

A round bottom flask was charged with Intermediate 11 (10.0 g, 44 mmol), dimethylacetamide (125 mL), potassium hexacyanferrate (II) trihydrate (24.2 g, 22 mmol), palladium (II) acetate (1.3 g, 2.2 mmol), DABCO (1.3 g, 4.4 mmol), and sodium carbonate (12.2 g, 44 mmol). The resulting mixture was heated to 150° C. under nitrogen for 17 h. The reaction mixture was cooled to rt and filtered through a pad of silica gel. The pad was washed with EtOAc (200 mL). The combined filtrate and washing were diluted with more EtOAc (200 mL), washed with brine (3×100 mL), dried over MgSO$_4$, filtered and concentrated under reduced pressure. The crude was purified by column chromatography (silica, DCM/MeOH 99:1) to give 10.5 g title compound (55%). $^1$H NMR (400 MHz, CDCl$_3$) δ ppm 1.00-1.15 (m, 2H) 1.47-1.58 (m, 1H) 1.88-1.94 (m, 1H) 3.56-3.76 (m, 2H) 7.15 (d, J=8.5 Hz, 2H) 7.55 (d, J=8.5 Hz, 2H).

Intermediate 13 (First Method)

trans-2-(4-cyanophenyl)cyclopropanecarboxylic acid

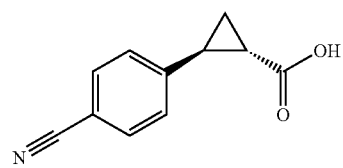 [SMILES: N#Cc1ccc([C@H]2C[C@@H]2C(=O)O)cc1]

Intermediate 12 (11.2 g, 64.7 mmol) was dissolved in acetone (100 mL). The solution was cooled to −10° C. Jones reagent (65 mL) was added over a period of 30 min. After completing addition, the reaction was warmed to rt and then quenched by adding 2-propanol (100 mL). The resulting mixture was diluted with EtOAc (200 mL). MgSO$_4$ was added and stirring was continued for another 30 min. The mixture was filtered and the filtrate was concentrated under reduced pressure. The residue was redissolved in EtOAc (200 mL), washed with 2×75 mL of water, dried over MgSO$_4$, filtered and concentrated under reduced pressure. The crude was purified by trituration with EtOAc (20 mL) to afford 5.2 g title compound (43%) as a solid. $^1$H NMR (400 MHz, DMSO-d$_6$) δ ppm 1.39-1.46 (m, 1H) 1.47-1.55 (m, 1H) 1.90-1.98 (m, 1H) 2.45-2.55 (m, 1H) 7.38 (d, J=8.2 Hz, 2H) 7.73 (d, J=8.2 Hz, 2H).

Preparation of Jones Reagent:

Jones reagent was prepared by dissolving 26.7 g of CrO$_3$ in 23 mL concentrated H$_2$SO$_4$ and diluting the mixture to 100 mL with water.

Intermediate 13 (Second Method)

trans-2-(4-cyanophenyl)cyclopropanecarboxylic acid

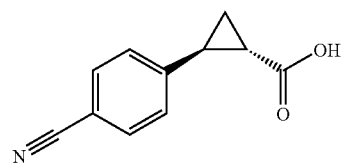 [SMILES: N#Cc1ccc([C@H]2C[C@@H]2C(=O)O)cc1]

Intermediate 10 (11.6 g, 47.7 mmol) was dissolved in MeOH (55 mL). A solution of NaOH (5.7 g, 143.1 mmol) in water (30 mL) was added and the resultant mixture was heated at 70° C. for 4 h. After cooling to rt, the mixture was concentrated to one-third its volume and diluted by the addition of 50 mL of 0.5 M NaOH. The resultant mixture was washed with 2×25 mL of MTBE. The aq. layer was separated and acidified by addition of concentrated HCl until pH 1. The acidified aq. phase was extracted with 2×50 mL of EtOAc. The combined organic extracts were dried over MgSO$_4$, filtered and evaporated to dryness. The crude was purified by flash chromatography (silica, DCM:MeOH 99:1 to 90:10), giving 3.1 g title compound (36.4%) as a solid. $^1$H NMR (400 MHz, CDCl$_3$) δ ppm 1.37-1.46 (m, 1H) 1.47-1.55 (m, 1H) 1.87-1.98 (m, 1H) 2.43-2.49 (m, 1H) 7.38 (d, J=8 Hz, 2H) 7.74 (d, J=8 Hz, 2H) 12.43 (s, 1H).

Intermediate 14 trans-2-(4-carbamoylphenyl)cyclopropanecarboxylic acid

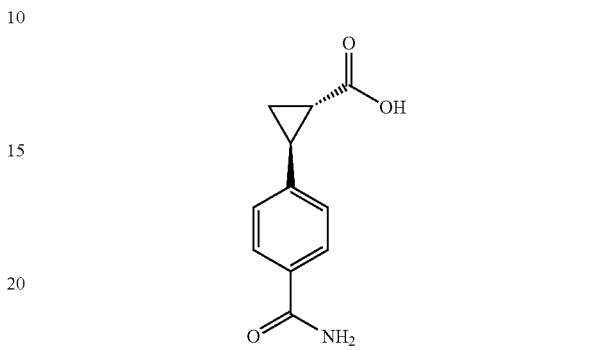

Intermediate 13 (3.4 g, 18.16 mmol) was dissolved in tBuOH (90 mL). Grounded KOH (5.10 g, 90.81 mmol) was added, the reaction mixture was heated to 70° C. overnight, cooled to rt and concentrated under reduced pressure. The residue was redissolved in water and washed with EtOAc. The aq. phase was acidified to pH 4-5 with 1 M HCl. The precipitate was filtered and dried under vacuum to give 3.06 g title compound (82%) as a solid. The product was used in the next step without further purification. $^1$H NMR (400 MHz, CD$_3$OD) δ ppm 1.42 (ddd, J=8.50, 6.35, 4.69 Hz, 1H) 1.55-1.62 (m, 1H) 1.91 (ddd, J=8.50, 5.37, 4.10 Hz, 1H) 2.52 (ddd, J=9.18, 6.25, 4.10 Hz, 1H) 7.20-7.26 (m, 2H) 7.76-7.83 (m, 2H); MS m/z 206.22 [M+H]$^+$ (ES+).

Intermediate 15

(R)-tert-butyl 4-(trans-2-(4-carbamoylphenyl)cyclopropanecarbonyl)-3-methylpiperazine-1-carboxylate

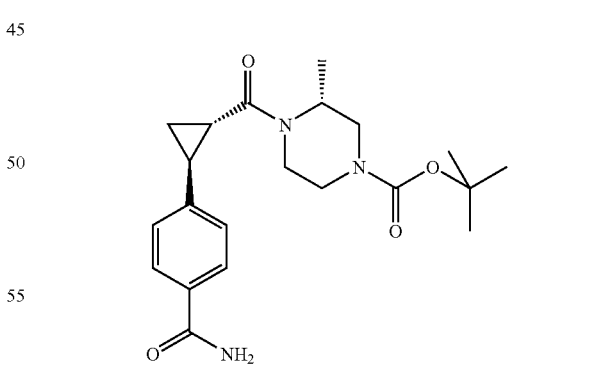

Intermediate 14 (450 mg, 2.19 mmol) was dissolved in DMF (20 mL). DIPEA (1.149 mL, 6.58 mmol) was added, followed by HOBT (444 mg, 3.29 mmol), EDC (631 mg, 3.29 mmol) and intermediate 3 (527 mg, 2.63 mmol). The reaction mixture was stirred at rt for 2 days, concentrated under reduced pressure, redissolved in EtOAc, washed with 1M HCl and sat. NaHCO$_3$, dried over MgSO$_4$, filtered and concentrated under reduced pressure to give title compound as a solid. The crude product was used in the next step without further purification. MS m/z 388.34 [M+H]+ (ESI).

Intermediate 16

(S)-tert-butyl 4-(trans-2-(4-carbamoylphenyl)cyclopropanecarbonyl)-3-methylpiperazine-1-carboxylate

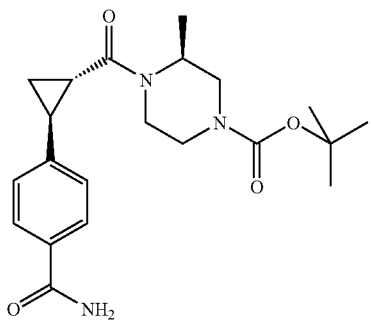 [SMILES: C[C@H]1CN(C(=O)OC(C)(C)C)CCN1C(=O)[C@H]1C[C@@H]1c1ccc(C(N)=O)cc1]

Intermediate 14 (450 mg, 2.19 mmol) was dissolved in DMF (20 mL). DIPEA (1.149 mL, 6.58 mmol) was added, followed by HOBT (444 mg, 3.29 mmol), EDC (631 mg, 3.29 mmol) and intermediate 6 (527 mg, 2.63 mmol). The mixture was stirred at rt overnight, concentrated under reduced pressure, redissolved in EtOAc washed with 1M HCl and sat. NaHCO$_3$, dried over MgSO$_4$, filtered and concentrated under reduced pressure to give title compound as a gum. The crude product was used in the next step without further purification. MS m/z 388.31 [M+H]+ (ESI).

Intermediate 17

(R)-tert-butyl 4-(trans-2-(4-carbamoylphenyl)cyclopropanecarbonyl)-3-ethylpiperazine-1-carboxylate

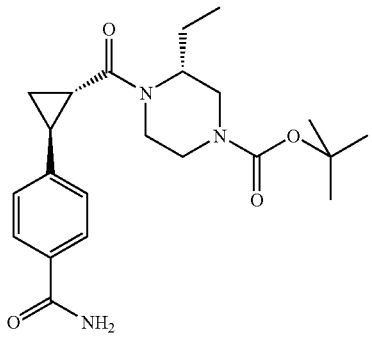 [SMILES: CC[C@@H]1CN(C(=O)OC(C)(C)C)CCN1C(=O)[C@H]1C[C@@H]1c1ccc(C(N)=O)cc1]

Intermediate 14 (300 mg, 1.46 mmol) was dissolved in DMF (15 mL). DIPEA (0.766 mL, 4.39 mmol) was added, followed by HOBT (296 mg, 2.19 mmol), EDC (420 mg, 2.19 mmol) and (R)-tert-butyl 3-ethylpiperazine-1-carboxylate (376 mg, 1.75 mmol). The mixture was stirred at rt for 2 h, concentrated under reduced pressure, redissolved in DCM, washed with sat NaHCO$_3$, dried over MgSO$_4$, filtered and concentrated under reduced pressure. The crude material was purified on preparative HPLC UV using the long high pH shallow gradient method (Mobile phase: 30-50% B; A: H$_2$O with 10 mM NH$_4$CO$_3$ and 0.375% NH$_4$OH v/v, B: CH$_3$CN, 30 min run) on XBridge Prep C18 OBD, 50×250 mm, 10 µm, Waters reverse phase column, giving 470 mg title compound (80%) as a white crystalline solid. $^1$H NMR (400 MHz, CD$_3$OD) δ ppm 0.72 (t, J=7.42 Hz, 1H) 0.84-1.00 (m, 2H) 1.34-1.44 (m, 1H) 1.46 (s, 9H) 1.50-1.80 (m, 3H) 2.24-2.58 (m, 2H) 2.97 (br. s., 3H) 3.92-4.11 (m, 2.5H) 4.11-4.27 (m, 0.5H) 4.28-4.39 (m, 0.5H) 4.43-4.56 (m, 0.5H) 7.21-7.30 (m, 2H) 7.80 (d, J=8.59 Hz, 2H); MS m/z 402.33 [M+H]+ (ESI).

Intermediate 18

(S)-tert-butyl 4-(trans-2-(4-carbamoylphenyl)cyclopropanecarbonyl)-3-ethylpiperazine-1-carboxylate

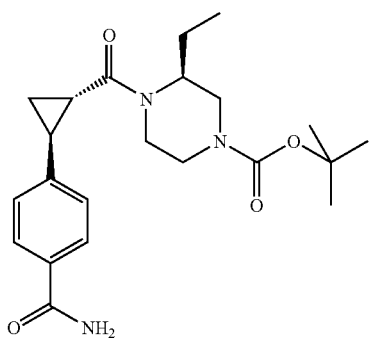 [SMILES: CC[C@H]1CN(C(=O)OC(C)(C)C)CCN1C(=O)[C@H]1C[C@@H]1c1ccc(C(N)=O)cc1]

Intermediate 14 was dissolved in DMF (15 mL). DIPEA (0.766 mL, 4.39 mmol) was added, followed by HOBT (296 mg, 2.19 mmol), EDC (420 mg, 2.19 mmol) and (S)-tert-butyl 3-ethylpiperazine-1-carboxylate (376 mg, 1.75 mmol). The mixture was stirred at rt for 2 h, concentrated under reduced pressure, redissolved in DCM, washed with sat. NaHCO$_3$, dried over MgSO$_4$, filtered and concentrated under reduced pressure. The crude material was purified on preparative HPLC UV using the long high pH shallow gradient method (Mobile phase: 30-50% B; A: H$_2$O with 10 mM NH$_4$CO$_3$ and 0.375% NH$_4$OH v/v, B: CH$_3$CN, 30 min run) on XBridge Prep C18 OBD, 50×250 mm, 10 µm, Waters reverse phase column, giving 455 mg title compound (77%) as a white crystalline solid. $^1$H NMR (400 MHz, CD$_3$OD) δ ppm 0.72 (t, J=7.42 Hz, 1H) 0.82-0.01 (m, 2H) 1.34-1.42 (m, 1H) 1.45 (s, 9H) 1.50-1.79 (m, 3H) 2.25-2.50 (m, 2H) 2.73-3.20 (m, 3H) 3.91-4.11 (m, 2.5H) 4.19 (br. s., 0.5H) 4.33 (br. s., 0.5H) 4.50 (br. s., 0.5H) 7.19-7.34 (m, 2H) 7.81 (d, J=8.59 Hz, 2H); MS m/z 402.32 [M+H]+ (ESI).

Intermediate 19 tert-butyl 4-(trans-2-(4-carbamoylphenyl)cyclopropanecarbonyl)-3,3-dimethylpiperazine-1-carboxylate

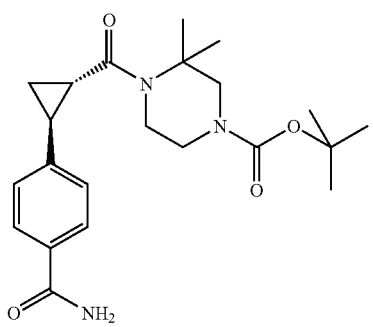 [SMILES: CC(C)(C)OC(=O)N1CCN(C(=O)[C@H]2C[C@@H]2c2ccc(C(N)=O)cc2)C(C)(C)C1]

Intermediate 14 was dissolved in DMF (20 mL). DIPEA (1.021 mL, 5.85 mmol) was added, followed by HOBT (395 mg, 2.92 mmol), EDC (561 mg, 2.92 mmol) and tert-butyl 3,3-dimethylpiperazine-1-carboxylate (587 mg, 2.34 mmol). The reaction mixture was stirred at rt overnight, concentrated under reduced pressure, redissolved in DCM, washed with 1M HCl and sat NaHCO$_3$, dried over MgSO$_4$, filtered and concentrated under reduced pressure. The crude material was purified on preparative HPLC UV using the long high pH shallow gradient method (Mobile phase: 30-50% B; A: H$_2$O with 10 mM NH$_4$CO$_3$ and 0.375% NH$_4$OH v/v, B: CH$_3$CN, 30 min run) on XBridge Prep C18 OBD, 50×250 mm, 10 μm, Waters reverse phase column, giving 412 mg title compound (52.6%) as a solid. $^1$H NMR (400 MHz, CDCl$_3$) δ ppm 1.22-1.35 (m, 9H) 1.38-1.55 (m, 9H) 1.71 (br. s., 1H) 1.94 (br. s., 1H) 2.47 (br. s., 1H) 2.88 (s, 3H) 2.96 (s, 3H) 3.32-3.59 (m, 4H) 3.65-3.85 (m, 2H) 5.77 (br. s., 1H) 6.16 (br. s., 1H) 7.17 (d, J=8.20 Hz, 2H) 7.75 (d, J=8.20 Hz, 2H); MS m/z 402.21 [M+H]$^+$ (ESI).

Intermediate 20

4-(trans-2-((R)-2-methylpiperazine-1-carbonyl)cyclopropyl)benzamide

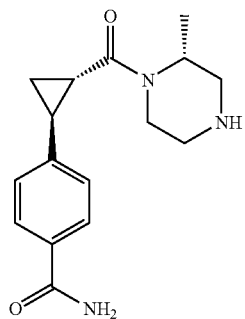 [SMILES: C[C@@H]1CNCCN1C(=O)[C@H]1C[C@@H]1c1ccc(C(N)=O)cc1]

Intermediate 15 (849 mg, 2.19 mmol) was dissolved in DCM (10.0 mL). TFA (5.00 mL) was added and the reaction mixture stirred at rt for 30 min. Volatiles were evaporated under reduced pressure to give a yellow gum. The crude material was used in the next step without purification. $^1$H NMR (400 MHz, CD$_3$OD) δ ppm 1.33 (d, J=7.03 Hz, 3H) 1.37-1.52 (m, 3H) 1.65 (br. s., 1H) 2.26-2.39 (m, 1H) 2.51 (br. s., 1H) 3.11 (br. s., 1H) 3.21-3.45 (m, 4H) 7.27 (d, J=8.20 Hz, 2H) 7.81 (d, J=8.20 Hz, 2H).

Intermediate 21

4-(trans-2-((S)-2-methylpiperazine-1-carbonyl)cyclopropyl)benzamide

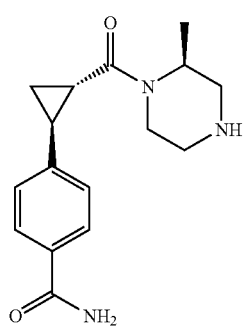 [SMILES: C[C@H]1CNCCN1C(=O)[C@H]1C[C@@H]1c1ccc(C(N)=O)cc1]

Intermediate 16 (849 mg, 2.19 mmol) was dissolved in DCM (10 mL). TFA (5.00 mL) was added and the reaction mixture stirred at rt for 30 min. Volatiles were evaporated under reduced pressure to give a yellow gum. The crude material was used in the next step without purification. $^1$H NMR (400 MHz, CD$_3$OD) δ ppm 1.28-1.37 (m, 3H) 1.37-1.52 (m, 3H) 1.65 (br. s., 1H) 2.28-2.39 (m, 1H) 2.51 (br. s., 1H) 3.10 (br. s., 1H) 3.38 (m, 4H) 7.27 (d, J=8.20 Hz, 2H) 7.81 (d, J=8.20 Hz, 2H).

Intermediate 22

4-(trans-2-((R)-2-ethylpiperazine-1-carbonyl)cyclopropyl)benzamide

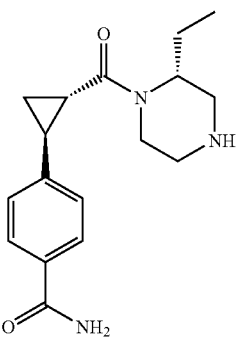 [SMILES: CC[C@@H]1CNCCN1C(=O)[C@H]1C[C@@H]1c1ccc(C(N)=O)cc1]

Intermediate 17 (445 mg, 1.11 mmol) was dissolved in DCM (5 mL). TFA (2.50 mL) was added and the reaction mixture stirred at rt for 30 min. Volatiles were evaporated under reduced pressure to give a yellow gum. The crude material was used for the next step without purification. $^1$H NMR (400 MHz, CD$_3$OD) δ ppm 0.68-0.84 (m, 1.5H) 0.85-1.05 (m, 3.5H) 1.39-1.50 (m, 1.5H) 1.66-1.80 (m, 0.5H) 2.26-2.50 (m, 2H) 3.01-3.11 (m, 1H) 3.32-3.43 (m, 4H) 4.43-4.82 (m, 2H) 7.21-7.31 (m, 2H) 7.77-7.86 (m, 2H).

Intermediate 23

4-(trans-2-((S)-2-ethylpiperazine-1-carbonyl)cyclopropyl)benzamide

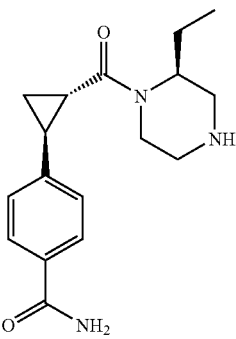 [SMILES: CC[C@H]1CNCCN1C(=O)[C@H]1C[C@@H]1c1ccc(C(N)=O)cc1]

Intermediate 18 (429 mg, 1.07 mmol) was dissolved in DCM (5 mL). TFA (2.50 mL) was added and the reaction mixture stirred at rt for 1 h. Volatiles were evaporated under reduced pressure to give a yellow gum. The crude material was used for the next step without purification. $^1$H NMR (400

MHz, CD$_3$OD) δ ppm 0.68-0.85 (m, 1.5H) 0.85-1.09 (m, 3.5H) 1.44 (ddd, J=8.20, 6.45, 4.49 Hz, 1.5H) 1.67-1.81 (m, 0.5H) 2.26-2.50 (m, 2H) 3.01-3.15 (m, 1H) 3.32-3.43 (m, 4H) 4.45-4.84 (m, 2H) 7.17-7.34 (m, 2H) 7.81 (d, J=8.59 Hz, 2H).

Intermediate 24

4-(trans-2-(2,2-dimethylpiperazine-1-carbonyl)cyclopropyl)benzamide

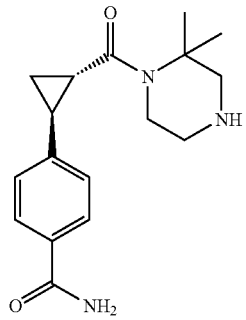 [SMILES: CC1(C)CNCCN1C(=O)[C@H]1C[C@@H]1c1ccc(C(N)=O)cc1]

Intermediate 19 (392 mg, 0.98 mmol) was dissolved in DCM (7 mL). TFA (3.50 mL) was added and the reaction mixture stirred at rt for 30 min. Volatiles were evaporated under reduced pressure to give a yellow gum. The crude material was used in the next step without purification. $^1$H NMR (400 MHz, CD$_3$OD) δ ppm 1.38 (ddd, J=8.40, 6.25, 4.49 Hz, 1H) 1.50-1.63 (m, 1H) 2.21-2.28 (m, 1H) 2.43 (ddd, J=9.08, 6.15, 4.30 Hz, 1H) 2.86 (s, 3H) 3.00 (s, 3H) 3.19 (s, 2H) 3.37 (t, J=5.66 Hz, 2H) 3.90 (q, J=5.47 Hz, 2H) 7.26 (d, J=8.20 Hz, 2H) 7.80 (d, J=8.20 Hz, 2H); MS m/z 302.28 [M+H]$^+$ (ESI).

Intermediate 25

(E)-methyl 3-(3-cyanophenyl)acrylate

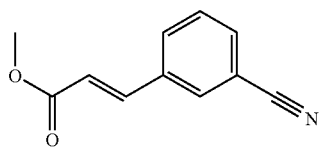

Methyl 2-(dimethoxyphosphoryl)acetate (20.83 g, 114.39 mmol) was dissolved in THF (500 mL). Sodium hydride (4.58 g, 114.39 mmol) was added in small portions. 3-formylbenzonitrile (10 g, 76.26 mmol) was added dissolved in 50 mL of THF and the reaction mixture was stirred at rt for 2 h. The reaction mixture was diluted with heptane, washed with H$_2$O, dried over sodium sulfate, filtered and concentrated under reduced pressure. The resulting solid was triturated in heptane, filtered, washed with heptane and dried under vacuum, giving 13.26 g title compound (93%) as a white powder. $^1$H NMR (400 MHz, CDCl$_3$) δ ppm 3.83 (s, 3H) 6.50 (d, J=16.02 Hz, 1H) 7.52 (t, J=7.81 Hz, 1H) 7.61-7.84 (m, 4H).

Intermediate 26

Trans-methyl 2-(3-cyanophenyl)cyclopropanecarboxylate

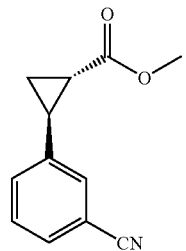

Trimethylsulfoxonium iodide (4.23 g, 19.23 mmol) was dissolved in DMSO (160 mL). Potassium tert-butoxide (2.158 g, 19.23 mmol) was added and the mixture was heated until complete dissolution. Intermediate 25 (3.0 g, 16.03 mmol) was added and the reaction mixture stirred 4 h at rt, concentrated under reduced pressure, diluted with EtOAc, washed with H$_2$O, dried over MgSO$_4$, filtered and concentrated under reduced pressure. The crude material was purified on silica gel by MPLC using 0-5% MeOH in DCM to provide 0.771 g title compound (23.91%) as a solid. $^1$H NMR (400 MHz, CDCl$_3$) δ ppm 1.34 (ddd, J=8.50, 6.35, 4.69 Hz, 1H) 1.63-1.72 (m, 1H) 1.93 (ddd, J=8.50, 5.37, 4.10 Hz, 1H) 2.56 (ddd, J=9.28, 6.35, 4.30 Hz 3.74 (s, 3H) 7.32-7.44 (m, 3H) 7.48-7.54 (m, 1H); MS m/z 201.92 [M+H]$^+$ (ESI).

Intermediate 27 trans-2-(3-carbamoylphenyl)cyclopropanecarboxylic acid

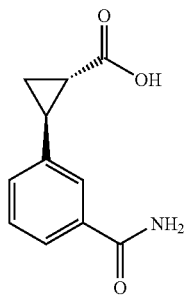 [SMILES: NC(=O)c1cccc([C@H]2C[C@@H]2C(=O)O)c1]

Intermediate 26 (771 mg, 3.83 mmol) was dissolved in tBuOH (80 mL). Ground KOH (1.075 g, 19.16 mmol) was added and the reaction mixture was heated to 70° C. overnight. After cooling to rt, the solid formed was filtered and dissolved in H$_2$O. The aq. phase was acidified to pH 2-3 with 2M HCl. The precipitate formed was filtered and dried under vacuum to provide 481 mg title compound (61.2%) as a solid. $^1$H NMR (400 MHz, CD$_3$OD) δ ppm 1.43 (ddd, J=8.40, 6.45, 4.69 Hz, 1H) 1.52-1.62 (m, 1H) 1.85-1.95 (m, 1H) 2.53 (ddd, J=9.18, 6.45, 4.30 Hz, 1H) 7.31-7.44 (m, 2H) 7.64 (t, J=1.76 Hz, 1H) 7.71 (ddd, J=7.23, 1.95, 1.76 Hz, 1H); MS m/z 205.91 [M+H]$^+$ (ESI).

Intermediate 28

(R)-tert-butyl 4-(trans-2-(3-carbamoylphenyl)cyclopropanecarbonyl)-3-methylpiperazine-1-carboxylate

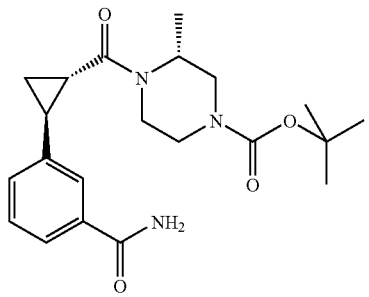 [SMILES: C[C@@H]1CN(C(=O)OC(C)(C)C)CCN1C(=O)[C@H]1C[C@@H]1c1cccc(C(N)=O)c1]

Intermediate 27 (110 mg, 0.54 mmol) was dissolved in DMF (10 mL). DIPEA (0.281 mL, 1.61 mmol) was added, followed by HOBT (109 mg, 0.80 mmol), EDC (154 mg, 0.80 mmol) and intermediate 3 (129 mg, 0.64 mmol). The reaction mixture was stirred at rt overnight, concentrated under reduced pressure, redissolved in EtOAc, washed with 1M HCl and sat. NaHCO$_3$, dried over MgSO$_4$, filtered and concentrated under reduced pressure to give 137 mg title compound (66.2%) as an orange gummy solid. The crude product was used in the next step without further purification. MS m/z 388.27 [M+H]$^+$ (ESI).

Intermediate 29

(S)-tert-butyl 4-(trans-2-(3-carbamoylphenyl)cyclopropanecarbonyl)-3-methylpiperazine-1-carboxylate

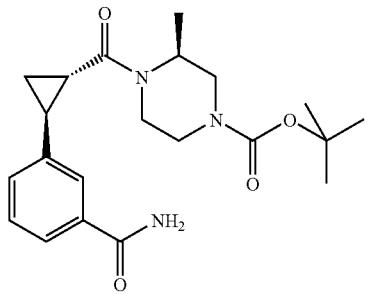 [SMILES: C[C@H]1CN(C(=O)OC(C)(C)C)CCN1C(=O)[C@H]1C[C@@H]1c1cccc(C(N)=O)c1]

Intermediate 27 (110 mg, 0.54 mmol) was dissolved in DMF (10 mL). DIPEA (0.281 mL, 1.61 mmol) was added, followed by HOBT (109 mg, 0.80 mmol), EDC (154 mg, 0.80 mmol) and intermediate 6 (129 mg, 0.64 mmol). The reaction mixture was stirred at rt overnight, concentrated under reduced pressure, redissolved in EtOAc, washed with 1M HCl and sat. NaHCO$_3$, dried over MgSO$_4$, filtered and concentrated under reduced pressure to give 133 mg title compound (64.1%) as an orange gummy solid. The crude product was used in the next step without further purification. MS m/z 388.27 [M+H]$^+$ (ESI).

Intermediate 30

3-(trans-2-((R)-2-methylpiperazine-1-carbonyl)cyclopropyl)benzamide

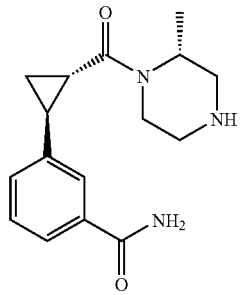 [SMILES: C[C@@H]1CNCCN1C(=O)[C@H]1C[C@@H]1c1cccc(C(N)=O)c1]

Intermediate 28 (135 mg, 0.35 mmol) was dissolved in DCM (2.5 mL). TFA (1.25 mL) was added and the reaction mixture stirred at rt for 4.5 h. Volatiles were evaporated under reduced pressure to give a dark orange gummy solid. The crude material was used in the next step without purification. $^1$H NMR (400 MHz, CD$_3$OD) δ ppm 1.23-1.49 (m, 5H) 1.61 (br. s., 1H) 2.31 (dq, J=8.74, 4.51 Hz, 1H) 2.51 (br. s., 1H) 2.86 (s, 1H) 3.00 (s, 1H) 3.02-3.30 (m, 2H) 3.33-3.43 (m, 2H) 7.39 (d, J=4.69 Hz, 2H) 7.65 (s, 1H) 7.71 (t, J=3.71 Hz, 1H).

Intermediate 31

3-(trans-2-((S)-2-methylpiperazine-1-carbonyl)cyclopropyl)benzamide

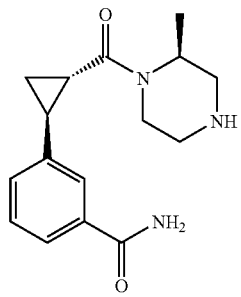 [SMILES: C[C@H]1CNCCN1C(=O)[C@H]1C[C@@H]1c1cccc(C(N)=O)c1]

Intermediate 29 (130 mg, 0.34 mmol) was dissolved in DCM (2.5 mL). TFA (1.25 mL) was added and the reaction mixture stirred at rt for 4 h. Volatiles were evaporated under reduced pressure to give a dark orange gummy solid. The crude material was used for the next step without purification. $^1$H NMR (400 MHz, CD$_3$OD) δ ppm 1.22-1.52 (m, 5H) 1.62 (br. s., 1H) 2.25-2.36 (m, 1H) 2.51 (br. s., 1H) 2.86 (s, 1H) 3.00 (s, 1H) 3.05-3.30 (m, 3H) 3.34-3.44 (m, 1H) 7.39 (d, J=4.69 Hz, 2H) 7.65 (s, 1H) 7.67-7.75 (m, 1H).

Intermediate 32

(R)-1-Cyclobutyl-3-methylpiperazine×2HCl

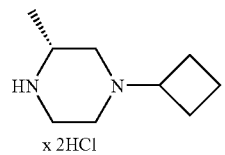

x 2HCl (R)-Boc-2-methylpiperazine (350 g, 1.71 moles, 98% w/w), which is commercially available from Lanzhou Boc Chemical Co., was dissolved in EtOH (2.75 L) at $t_{jacket}$=20° C. Acetic acid (1.37 L) was added in one portion followed by the addition of cyclobutanone (184 g, 2.57 moles). The charging vessel was rinsed with EtOH (250 mL) and the light yellow solution was left stirring at $t_{jacket}$=20° C. for 1 h. NaBH(OAc)$_3$ (497 g, 2.48 moles, 95% w/w) was added in 20 portions over 90 min. EtOH (340 mL) was used for rinsing. The reaction mixture was left stirring for 2 h. A sample was analyzed on GC using HP-5MS column (length 25 m, ID 0.32 mm, Film 0.52 μm) with a gradient method (2 min at 60° C., followed by 25° C./min during 8 min then 2 min at 260° C.). Frontinlet temperature=200° C. using He as gas and a detector temperature=300° C. More NaBH(OAc)$_3$ (30 g, 0.14 moles) was added to complete the reaction within 1 h. The reaction mixture was cooled to $t_{jacket}$=0° C. before quenching with 5M NaOH (5.5 L). EtOH was distilled off under vacuum at $t_{jacket}$=50° C. The H$_2$O phase was extracted with toluene (5.5 L) at $t_{jacket}$=20° C. The organic phase was combined with a second batch, started with (R)-Boc-2-methylpiperazine (300 g, 1.47 moles, 98% w/w). The combined organic phases were concentrated under vacuum at $t_{jacket}$=50° C. to approximately 2 L. The obtained toluene solution with the intermediate can be stored at 5° C. for several days. The toluene solution was diluted with 2-propanol (2 L) at $t_{jacket}$=10° C., and HCl in 2-propanol (1.06 L, 6.36 moles, 6M) diluted in 2-propanol (2 L) was added over 30 min. The reaction solution was heated to $t_{jacket}$=48° C. HCl in 2-propanol (2.12 L, 12.72 moles, 6M) diluted in 2-propanol (2 L) was added over 2 h at $t_{inner}$=46° C. The reaction solution was kept at $t_{jacket}$=48° C. for an additional 3 h before being cooled to $t_{jacket}$=0° C. over 1 h. A seed mixture (0.4 L reaction solution with Intermediate 32 (0.2 g, 0.89 mmoles)) was added. The reaction mixture was left stirring at $t_{jacket}$=0° C. overnight and the product was filtered off. Drying under vacuum at 40° C. gave Intermediate 32 (620 g, 2.63 moles, 96.3% w/w, 83% yield). $^1$H-NMR (DMSO-d$_6$): δ 12.46 (s, 1H), 10.13 (s, 2H), 3.35-3.74 (m, 6H), 3.09 (m, 1H), 2.92 (m, 1H), 2.39 (m, 2H), 2.16 (m, 2H), 1.72 (m, 2H), 1.32 (d, 3H, J=6.4 Hz); $^{13}$C-NMR (DMSO-d$_6$): δ 58.50, 49.62, 48.13, 44.30, 24.48, 24.38, 15.25, 13.26.

Intermediate 33

(R)-1-(4-Bromo-phenyl)-2-chloro-ethanol

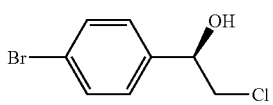

Borane dimethylsulfide (2.0 kg, 24.8 moles, 94% w/w) was mixed in toluene (8 L) at $t_{jacket}$=20° C. (R)-(+)-Methyl-CBS-oxazaborolidine (2.6 kg, 2.74 moles, 1M) as a toluene solution was added. The charging vessel was rinsed with toluene (0.5 L) and $t_{jacket}$ was set to 45° C. 1-(4-Bromo-phenyl)-2-chloro-ethanone (7.84 kg, 33.6 moles), which is commercially available from Jiangyan Keyan Fine Chemical Co. Ltd, was dissolved in 2-MeTHF (75 L) in a separate vessel and when $t_{inner}$ was above 40° C. in the first vessel, the 2-MeTHF solution was added during 3 h. The latter vessel was rinsed with 2-MeTHF (2 L) and added to the reaction mixture, which was left stirring at $t_{jacket}$=45° C. for 1 h. Analysis of a sample on HPLC indicated full conversion at this point using the following gradient method (mobile phase 20-95% B; A: 5% CH$_3$CN in H$_2$O with 0.1% TFA, B: 95% CH$_3$CN in H$_2$O with 0.085% TFA, 10 min run) on Chromolith Performance RP-18e, 4.6×100 mm. The reaction mixture was cooled to $t_{jacket}$=10° C. before slow quench with MeOH (36 L). The first liter of MeOH was added during 30 min. and the rest during additional 30 min. MeOH was distilled off under vacuum at $t_{jacket}$=50° C. The organic solution left was cooled to $t_{jacket}$=20° C., washed with 1M HCl in H$_2$O (7 L conc HCl+73 L H$_2$O) and concentrated under vacuum at $t_{jacket}$=50° C. to approximately 40 L. Intermediate 33 obtained in a 2-MeTHF solution can be stored at 10° C. for 20 h or used directly in the next synthetic step.

Intermediate 34

(R)-2-(4-Bromo-phenyl)-oxirane

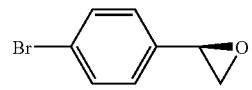

Aliquat® 175 (methyl tributyl ammonium chloride) (1.12 kg, 4.75 moles) was added to Intermediate 33 as a 2-MeTHF solution (33.6 moles, 40 L) at $t_{jacket}$=20° C. NaOH (5.1 kg, 57.4 moles, 45% w/w) diluted in H$_2$O (2 L) was added during 20 min. The reaction mixture was left stirring at $t_{jacket}$=20° C. for 2 h. Analysis of a sample on HPLC indicated full conversion at this point using the following gradient method (mobile phase 20-95% B; A: 5% CH$_3$CN in H$_2$O with 0.1% TFA, B: 95% CH$_3$CN in H$_2$O with 0.085% TFA, 10 min run) on Chromolith Performance RP-18e, 4.6×100 mm. The aq. phase was separated off and the organic phase washed with H$_2$O (2×25 L). 2-MeTHF (25 L) was added and the organic phase concentrated under vacuum at $t_{jacket}$=50° C. to approximately 30 L. Intermediate 34 obtained in a 2-MeTHF solution, can be stored at 5° C. for 140 h or used directly in the next synthetic step.

Intermediate 35 (First Method)

(1S,2S)-2-(4-Bromo-phenyl)-cyclopropanecarboxylic acid

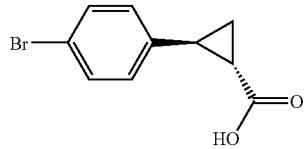 [SMILES: O=C(O)[C@H]1C[C@@H]1c1ccc(Br)cc1]

Triethyl phosphonoacetate (10.5 L, 51.9 moles, 98% w/w) was dissolved in 2-MeTHF (14 L) at $t_{jacket}$=20° C. Hexyl lithium in hexane (21 L, 48.3 moles, 2.3 M) was added at a rate to maintain $t_{inner}$ below 0° C. The charging vessel was rinsed with 2-MeTHF (3 L) and the reaction solution was left stirring at $t_{jacket}$=10° C. Intermediate 34 as a 2-MeTHF solution (33.6 moles, 30 L) was added during 20 min. The charging vessel was rinsed with 2-MeTHF (2 L) and the reaction solution was left stirring at $t_{jacket}$=65° C. for at least 16 h with the last 3 h at $t_{jacket}$=75° C. Analysis of a sample on HPLC using the following gradient method (mobile phase 20-95% B; A: 5% $CH_3CN$ in $H_2O$ with 0.1% TFA, B: 95% $CH_3CN$ in $H_2O$ with 0.085% TFA, 10 min run) on Chromolith Performance RP-18e, 4.6×100 mm indicated full conversion to the intermediate (1S,2S)-2-(4-bromo-phenyl)-cyclopropanecarboxylic acid ethyl ester. The reaction solution was cooled to $t_{jacket}$=20° C. NaOH (7.6 kg, 85.5 moles, 45% w/w) diluted in $H_2O$ (12 L) was added over 20 min. The reaction solution obtained was left stirring at $t_{jacket}$=60° C. for at least 2 h. Analysis of a sample on HPLC indicated full conversion at this point using the following gradient method (mobile phase 20-95% B; A: 5% $CH_3CN$ in $H_2O$ with 0.1% TFA, B: 95% $CH_3CN$ in $H_2O$ with 0.085% TFA, 10 min run) on Chromolith Performance RP-18e, 4.6×100 mm. The reaction solution was cooled to $t_{jacket}$=20° C., the aq. phase was separated off and the organic phase was extracted with $H_2O$ (37 L). The combined aq. phases were acidified to pH<3.5 with $H_3PO_4$ (9 L, 131 moles, 85% w/w) diluted in $H_2O$ (12.5 L). Only 17 L of the diluted $H_3PO_{4(aq)}$ was used to achieve the pH<3.5. The acidic aq. phase was extracted with 2-MeTHF (2×15 L). The combined organic phases including rinsing with 2-MeTHF (2 L) were concentrated under vacuum at $t_{jacket}$=50° C. to approximately 11 L. The 2-MeTHF solution was diluted with EtOH (14.5 L) at $t_{jacket}$=35° C. and $H_2O$ (16 L) was added over 20 min. The reaction solution was cooled to $t_{jacket}$=28° C. Seed (16 g, 0.066 moles) was added and the solution was stirred for 2 h at $t_{jacket}$=28° C. The reaction mixture was cooled to $t_{jacket}$=0° C. over 6 h and left stirring for at least 1 h. Additional $H_2O$ (8 L) was added during 40 min. and the product was filtered off and washed with cold $H_2O$ (10 L). Drying under vacuum at 40° C. gave 6.18 kg Intermediate 35 (21.5 moles, 84% w/w), 64% yield over four steps from 7.84 kg 1-(4-bromo-phenyl)-2-chloro-ethanone (33.6 moles).

Recrystallization of Intermediate 35: Two batches of Intermediate 35 (6.18+7.04 kg) were mixed in EtOH (52 L) and heated at $t_{jacket}$=70° C. $H_2O$ (52 L) was added. The reaction solution was cooled to $t_{jacket}$=30° C. over 2.5 h. $H_2O$ (16 L) was added during 20 min. and the crystallization was cooled to $t_{jacket}$=20° C. during 3 h. The product was filtered off and washed with a mixture of $H_2O$ (8 L) and EtOH (2 L). Drying under vacuum at 40° C. gave 10.0 kg Intermediate 35 (41.5 moles, 88% w/w, which was redissolved in toluene (39 L) and isooctane (57 L) at $t_{jacket}$=60° C. A clear solution was obtained. The reaction solution was cooled to $t_{jacket}$=45° C. and left stirring for 1 h, then cooled to $t_{jacket}$=20° C. over 2 h. The product was filtered off and washed with a mixture of toluene (4 L) and isooctane (36 L) in two portions. Drying under vacuum at 40° C. gave 7.4 kg Intermediate 35 (29.8 moles, 97% w/w), 44% yield over four steps from 7.84+7.93 kg 1-(4-bromo-phenyl)-2-chloro-ethanone (67.5 moles). $^1$H-NMR (DMSO-$d_6$): δ 12.36 (s, 1H), 7.44 (d, 2H, J=8 Hz), 7.13 (d, 2H, J=8 Hz), 2.39 (m, 1H), 1.81 (m, 1H), 1.43 (m, 1H), 1.33 (m, 1H); $^{13}$C-NMR (DMSO-$d_6$): δ 173.76, 139.88, 131.20, 128.24, 119.14, 24.73, 24.31, 16.78; LC-MS (ESI): m/z 239 (M-1 ($Br^{79}$)) and 241 (M-1 ($Br^{81}$)). $R_t$=5.03 min with the analytical method (mobile phase: 5-90% B; A: $H_2O$ with 0.1% formic acid, B: $CH_3CN$, 8.6 min run) on Xbridge C18, 3.0×50 mm, 2.5 μm particle size.

Intermediate 35 (Second Method)

(1S,2S)-2-(4-Bromo-phenyl)-cyclopropanecarboxylic acid

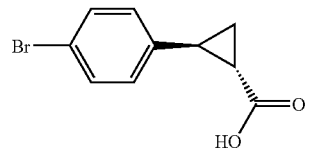 [SMILES: O=C(O)[C@H]1C[C@@H]1c1ccc(Br)cc1]

To a stirred solution of (trans)-2-(4-bromophenyl)cyclopropanecarboxylic acid (6.52 g, 27.04 mmol), which can be prepared in accordance with the process set forth on page 82 of WO 2009/024823, in 400 ml of EtOH was added a solution of (R)-(+)-1-(1-Naphthyl)ethylamine (4.63 g, 4.37 mL, 27.04 mmol) in 100 ml of EtOH followed by 25 ml of $H_2O$. This was stirred at rt for about 4 h. The solid was collected by filtration and washed with 40 ml of cold EtOH/$H_2O$ (20/1) to provide 3.18 g of salt as a white solid (58% recovery) equivalent to 1.86 g of free acid. This was taken up in 2 N NaOH and extracted 5 times with EtOAc. The aq. phase was placed on a rotary evaporator to remove the remaining EtOAc. The resulting clear solution was transferred to an erlenmeyer flask, cooled in an ice bath, and conc. HCl was added dropwise while stirring to pH 4. The resulting solid was collected by filtration providing 1.63 g of Intermediate 35. The product was analyzed by chiral SFC (UV detection) using isocratic method (mobile phase: 25% MeOH with 0.1% DMEA, supercritical $CO_2$) on ChiralPak AD-H, 10×250 mm, 5 μm particle size, giving an enantiomeric purity of >95%, $R_t$=3.88 min (isomer 1) and 4.79 min (isomer 2). $^1$H NMR (400 MHz, $CDCl_3$) δ ppm 1.37 (ddd, J=8.20, 6.64, 4.69 Hz, 1H), 1.67 (ddd, J=9.28, 5.08, 4.79 Hz, 1H), 1.87 (ddd, J=8.50, 4.69, 4.39 Hz, 1H), 2.48-2.63 (m, 1H), 6.87-7.06 (m, 2H), 7.37-7.46 (m, 2H).

Intermediate 36

(1S,2S)-2-(4-Cyano-phenyl)-cyclopropanecarboxylic acid

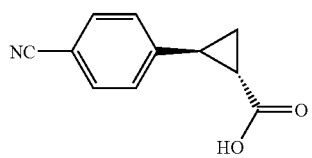

Intermediate 35 (first method) (3.7 kg, 14.9 moles, 97% w/w) and zinc-dust (98%+, <10 μm) (99 g, 1.51 moles) were mixed with DMF (13.5 L) and the slurry was stirred at $t_{jacket}$=20° C. The mixture was inerted and left with $N_2$ pressure of 0.1-0.2 bar. Bis(tri-t-butylphosphine)-palladium (0) (27.5 g, 0.054 moles) was added to the slurry, and the vessel was inerted and left with $N_2$ pressure of 0.1-0.2 bar. The mixture was heated to $t_{jacket}$=45° C., Zn(CN)$_2$ (1.0 kg, 8.52 moles) was added to the suspension in one portion, and the system was inerted and left with $N_2$ pressure of 0.1-0.2 bar (N.B. Cyanide salts are highly toxic). The resulting mixture was heated to $t_{jacket}=75°$ C. and stirred for at least 2 h. Analysis of a sample on HPLC indicated full conversion at this point using the following gradient method (mobile phase 20-95% B; A: 5% $CH_3CN$ in $H_2O$ with 0.05% formic acid, B: 95% $CH_3CN$ in $H_2O$ with 0.05% formic acid, 8 min run) on Chromolith Performance RP-18e, 4.6×100 mm. The reaction mixture was cooled to $t_{jacket}=20°$ C. Thiol-functionalized silica (Silicycle, SiliaBond Thiol) (1.07 kg, 28% w/w) was added and the vessel was inerted. The reaction mixture was stirred for at least 36 h at $t_{jacket}=20°$ C. The scavenger was filtered off via a filter with activated charcoal or equivalent (pall-filter). The vessel and the filter system were washed with 2-MeTHF (53 L). The filtrate and washings were combined and stirred at $t_{jacket}=5°$ C. A pale yellow liquid resulted. NaCl (3.5 kg) in $H_2O$ (16.4 L) was added during 15 min. at such a rate so the inner temperature remained below 15° C. The resulting reaction mixture was heated to $t_{jacket}=45°$ C. and the aq. phase was separated off. The organic phase was washed with $NaHSO_4 \times H_2O$ in $H_2O$ (2×(2.87 kg+16.4 L)) and NaCl in $H_2O$ (3.5 kg+16.4 L). The organic phase was cooled to $t_{jacket}=10°$ C. and NaOH (1.54 kg, 19.3 moles, 50% w/w) diluted in $H_2O$ (41 L) was added during 45 min. The resulting reaction mixture was heated to $t_{jacket}=30°$ C. and the organic phase was separated off. The aq. phase was stirred at $t_{jacket}=20°$ C. and pH adjusted to 6.5 with $H_3PO_4$ (0.90 kg, 7.81 moles, 85% w/w) diluted in $H_2O$ (5.3 L) at a rate that maintained the inner temperature below 25° C. 2-MeTHF and $H_2O$ were distilled off under vacuum until a volume 85-90% of the volume prior to distillation, approximately 8 L. The reaction mixture was cooled to $t_{jacket}=0°$ C. and continued charging off $H_3PO_4$ (1.17 kg, 10.1 moles, 85% w/w) diluted in $H_2O$ (8.2 L) until pH=4. The slurry was left stirring overnight at $t_{jacket}=10°$ C. The product was filtered off, washed with $H_2O$ (2×4 L). Drying under vacuum at 40° C. gave Intermediate 36 (2.24 kg, 11.2 moles, 93.2% w/w), 75% yield. $^1$H-NMR (DMSO-$d_6$): δ 12.45 (s, 1H), 7.72 (d, 2H, J=8 Hz), 7.37 (d, 2H, J=8 Hz), 2.50 (m, 1H), 1.94 (m, 1H), 1.50 (m, 1H), 1.42 (m, 1H); $^{13}$C-NMR (DMSO-$d_6$): δ 173.51, 146.68, 132.27, 126.93, 118.97, 108.85, 25.16, 25.04, 17.44; LC-MS (ESI): m/z 186 (M−1). $R_t=3.63$ min with the analytical method (mobile phase: 5-90% B; A: $H_2O$ with 0.1% formic acid, B: $CH_3CN$, 8.6 min run) on Xbridge C18, 3.0×50 mm, 2.5 μm particle size.

Intermediate 37

(1S,2S)-2-(4-Carbamoyl-phenyl)-cyclopropanecarboxylic acid

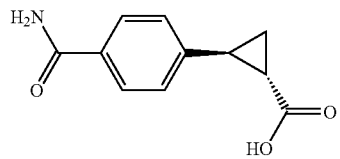 [SMILES: NC(=O)c1ccc([C@H]2C[C@@H]2C(=O)O)cc1]

Intermediate 36 (4.46 kg, 22.0 moles, 92.5% w/w) was mixed in $H_2O$ (40 L) at $t_{jacket}=30°$ C. NaOH (2.25 kg, 28.1 moles, 50% w/w) diluted in $H_2O$ (6 L) was added at such a rate so $t_{inner}$ remained below 35° C. The charging vessel was rinsed with $H_2O$ (1 L). If the pH was not ≥12, more NaOH was charged in the same concentration as previously. Hydrogen peroxide (4.89 kg, 50.3 moles, 35% w/w) was added at a rate to maintain $t_{inner}$ below 35° C. The charging vessel was rinsed with $H_2O$ (1 L) and the reaction slurry was left stirring for 0.5-1.0 h. Analysis of a sample on HPLC indicated full conversion at this point using the following gradient method (mobile phase 20-95% B; A: 5% $CH_3CN$ in $H_2O$ with 0.05% formic acid, B: 95% $CH_3CN$ in $H_2O$ with 0.05% formic acid, 8 min run) on Chromolith Performance RP-18e, 4.6×100 mm. The reaction mixture was cooled to $t_{jacket}=0°$ C. and left stirring for at least 0.5 h when the temperature was reached. The sodium salt of Intermediate 37 was filtered off and washed with cold $H_2O$ (2×7 L). The solid was slurry washed on the filter with $NaHSO_4 \times H_2O$ (2.76 kg, 20.0 moles) diluted in $H_2O$ (35 L). The slurry was kept stirring at $t_{jacket}=0°$ C. for 1 h. If the pH was not <3.7, it was adjusted with $NaHSO_4 \times H_2O$ in $H_2O$. The product was filtered off, washed with cold $H_2O$ (3×14 L). Drying under vacuum at 40° C. gave Intermediate 37 (4.0 kg, 18.2 moles, 93.4% w/w), 83% yield. $^1$H-NMR (DMSO-$d_6$): δ 12.40 (s, 1H), 7.94 (s, 1H), 7.79 (d, 2H, J=8 Hz), 7.32 (s, 1H), 7.23 (d, 2H, J=8 Hz), 2.44 (m, 1H), 1.88 (m, 1H), 1.47 (m, 1H), 1.39 (m, 1H); $^{13}$C-NMR (DMSO-$d_6$): δ 173.83, 167.67, 143.94, 132.17, 127.68, 125.73, 25.21, 24.67, 17.11; LC-MS (ESI): m/z 206 (M+1). $R_t=2.13$ min with the analytical method (mobile phase: 5-90% B; A: $H_2O$ with 0.1% formic acid, B: $CH_3CN$, 8.6 min run) on Xbridge C18, 3.0×50 mm, 2.5 μm particle size.

Intermediate 38

((1S,2S)-2-(4-bromophenyl)cyclopropyl)((R)-4-cyclobutyl-2-methylpiperazin-1-yl)methanone

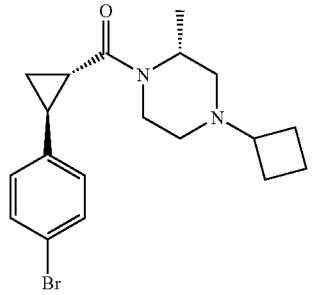 [SMILES: C[C@@H]1CN(C2CCC2)CCN1C(=O)[C@H]1C[C@@H]1c1ccc(Br)cc1]

To a solution of Intermediate 35 (second method) (5.87 g, 24.34 mmol) in DMF (120 mL) at 0° C. was added N,N-Diisopropylethylamine (21.20 mL, 121.72 mmol), 1-Hydroxybenzotriazole (4.93 g, 36.52 mmol), N-(3-Dimethylaminopropyl)-N'-ethylcarbodiimide hydrochloride (7 g, 36.52 mmol) followed by Intermediate 32 (5.53 g, 24.34 mmol). The reaction was stirred for 15 h then the reaction was concentrated and the residue taken into EtOAc and washed with a saturated solution of $NaHCO_3$. The aq. phase was extracted twice with EtOAc and the combined organics were washed with brine, dried over $MgSO_4$ filtered and concentrated. The resulting oil was purified by normal phase chromatography using a gradient of EtOAc/Heptane 20 to 100% on a 120 g Redisep column using an ISCO Companion instrument providing Intermediate 38 (8.50 g, 93%) as clear glass, which solidified slowly on standing. $^1$H-NMR (400 MHz, Methanol-$d_4$) δ ppm 1.27 (br. s., 3H) 1.38 (br. s., 1H) 1.48-1.58 (m, 1H) 1.64-1.77 (m, 3H) 1.77-1.87 (m, 1H) 1.87-1.99 (m, 2H) 1.98-2.09 (m, 2H) 2.14-2.22 (m, 1H) 2.34 (br. s., 1H) 2.63-2.76 (m, 2H) 2.85 (dddd, J=11.43, 3.61, 1.95, 1.76 Hz, 1H) 2.90-3.01 (m, 1H) 3.40 (br. s., 1H) 4.03 (d, J=11.33 Hz, 1H) 4.31 (d, J=11.72 Hz, 1H) 4.39 (br. s., 1H) 4.64 (br. s., 1H) 7.09 (d, J=8.20 Hz, 2H) 7.41 (d, J=8.59 Hz, 2H). The product was analyzed on analytical HPLC MS using the high pH gradient method (mobile phase: 5-95% B; A: $H_2O$ with 10 mM $NH_4CO_3$ and 0.375% $NH_4OH$ v/v, B: $CH_3CN$, 2.25 min run) on X-Bridge C18, 2.1×30 mm, 5 μm particle size. MS m/z 277.31 $[M+H]^+$ (ESI), $R_t$=2.10 min.

Intermediate 39

4-((1S,2S)-2-((R)-4-cyclobutyl-2-methylpiperazine-1-carbonyl)cyclopropyl)benzonitrile

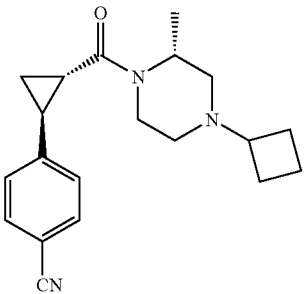 [SMILES: C[C@@H]1CN(C2CCC2)CCN1C(=O)[C@H]1C[C@@H]1c1ccc(C#N)cc1]

To a solution of Intermediate 38 (8.5 g, 22.53 mmol) in NMP (100 mL) while bubbling Ar was added Zinc (0.737 g, 11.26 mmol), Zinc cyanide (1.984 g, 16.90 mmol) and dichloro[1,1'-bis(di-t-butylphosphino)ferrocene]palladium (II) (0.335 g, 0.45 mmol). This was heated at 100° C. for 20 h. Some starting material was still present, therefore heating was continued for a further 24 h. The reaction was cooled and concentrated under high vac. The material was taken into EtOAc and filtered through celite. The filtrate was concentrated, divided into two portions of equal weight, wherein each portion was purified on a 120 g silica gel column eluting with a gradient of EtOAc/heptane 50-100% providing Intermediate 39 (6.10 g, 84%). The product was analyzed on analytical HPLC MS using the high pH gradient method (mobile phase: 5-95% B; A: $H_2O$ with 10 mM $NH_4CO_3$ and 0.375% $NH_4OH$ v/v, B: $CH_3CN$, 2.25 min run) on X-Bridge C18, 2.1×30 mm, 5 μm particle size. MS m/z 324.39 $[M+H]^+$ (ESI), $R_t$=1.76 min.

What is claimed is:

1. A compound or pharmaceutically acceptable salt thereof, wherein the compound is selected from the group consisting of:
    4-((trans)-2-((R)-4-cyclobutyl-2-methylpiperazine-1-carbonyl)cyclopropyl)benzamide, diastereomeric mixture;
    4-((trans)-2-((R)-4-cyclobutyl-2-methylpiperazine-1-carbonyl)cyclopropyl)benzamide, isomer 1; and
    4-((trans)-2-((R)-4-cyclobutyl-2-methylpiperazine-1-carbonyl)cyclopropyl)benzamide, isomer 2.

2. A pharmaceutical composition, wherein the composition comprises:
    a compound or pharmaceutically acceptable salt thereof according to claim 1, and
    a pharmaceutically acceptable carrier or diluent.

3. A compound or pharmaceutically acceptable salt thereof, wherein the compound is 4-{(1S, 2S)-2-[((R)-4-cyclobutyl-2-methylpiperazin-1-yl)carbonyl]cyclopropyl}-benzamide, which has the structure:

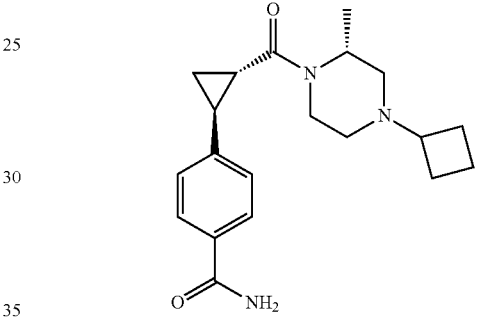

4. A pharmaceutical composition, wherein the composition comprises:
    a compound or pharmaceutically acceptable salt thereof according to claim 3, and a pharmaceutically acceptable carrier or diluent.

* * * * *